(12) United States Patent
Brinkmann et al.

(10) Patent No.: US 9,382,323 B2
(45) Date of Patent: Jul. 5, 2016

(54) MULTISPECIFIC ANTIBODIES COMPRISING FULL LENGTH ANTIBODIES AND SINGLE CHAIN FAB FRAGMENTS

(75) Inventors: Ulrich Brinkmann, Weilheim (DE); Peter Bruenker, Hittnau (CH); Rebecca Croasdale, Antdorf (DE); Christian Klein, Bonstetten (CH); Erhard Kopetzki, Penzberg (DE); Ekkehard Moessner, Kreuzlingen (CH); Joerg Thomas Regula, Munich (DE); Juergen Michael Schanzer, Traunstein (DE); Jan Olaf Stracke, Munich (DE); Pablo Umana, Zurich (CH)

(73) Assignee: Roche Glycart AG, Schlieren (CH)

( * ) Notice: Subject to any disclaimer, the term of this patent is extended or adjusted under 35 U.S.C. 154(b) by 479 days.

(21) Appl. No.: 12/750,748

(22) Filed: Mar. 31, 2010

(65) Prior Publication Data

US 2010/0256338 A1 Oct. 7, 2010

(30) Foreign Application Priority Data

Apr. 2, 2009 (EP) ..................... 09004909

(51) Int. Cl.
*C07K 16/00* (2006.01)
*C07K 16/28* (2006.01)
*C07K 16/46* (2006.01)
*A61K 39/00* (2006.01)

(52) U.S. Cl.
CPC ............. *C07K 16/2863* (2013.01); *C07K 16/00* (2013.01); *C07K 16/468* (2013.01); *A61K 2039/505* (2013.01); *C07K 2317/21* (2013.01); *C07K 2317/55* (2013.01); *C07K 2317/56* (2013.01); *C07K 2317/565* (2013.01); *C07K 2317/626* (2013.01); *C07K 2317/64* (2013.01); *C07K 2317/73* (2013.01); *C07K 2319/00* (2013.01)

(58) Field of Classification Search
CPC .. C07K 16/00; C07K 16/468; C07K 2319/00; C07K 2317/56; C07K 2317/565; C07K 2317/625; C07K 2317/64; C07K 2317/55; A61K 2039/505
USPC ..................... 424/133.1; 530/387.3
See application file for complete search history.

(56) References Cited

U.S. PATENT DOCUMENTS

| | | | |
|---|---|---|---|
| 3,773,919 A | 11/1973 | Boswell et al. |
| 3,896,111 A | 7/1975 | Kupchan et al. |
| 4,120,649 A | 10/1978 | Schechter |
| 4,137,230 A | 1/1979 | Hashimoto et al. |
| 4,151,042 A | 4/1979 | Higahide et al. |
| 4,248,870 A | 2/1981 | Miyashita et al. |
| 4,256,746 A | 3/1981 | Miyashita et al. |
| 4,260,608 A | 4/1981 | Miyashita et al. |
| 4,265,814 A | 5/1981 | Hashimoto et al. |
| 4,294,757 A | 10/1981 | Asai |
| 4,307,016 A | 12/1981 | Asai et al. |
| 4,308,268 A | 12/1981 | Miyashita et al. |
| 4,308,269 A | 12/1981 | Miyashita et al. |
| 4,309,428 A | 1/1982 | Miyashita et al. |
| 4,313,946 A | 2/1982 | Powell et al. |
| 4,315,929 A | 2/1982 | Freedman et al. |
| 4,317,821 A | 3/1982 | Miyashita et al. |
| 4,322,348 A | 3/1982 | Asai et al. |
| 4,331,598 A | 5/1982 | Hasegawa et al. |
| RE30,985 E | 6/1982 | Cartaya |
| 4,361,650 A | 11/1982 | Asai et al. |
| 4,362,663 A | 12/1982 | Kida et al. |
| 4,364,866 A | 12/1982 | Asai et al. |
| 4,371,533 A | 2/1983 | Akimoto et al. |
| 4,419,446 A | 12/1983 | Howely et al. |
| 4,424,219 A | 1/1984 | Hashimoto et al. |
| 4,450,254 A | 5/1984 | Isley et al. |
| 4,560,655 A | 12/1985 | Baker |
| 4,601,978 A | 7/1986 | Karin |
| 4,657,866 A | 4/1987 | Kumar |
| 4,665,077 A | 5/1987 | Stringfellow et al. |
| 4,767,704 A | 8/1988 | Cleveland |
| 4,816,567 A | 3/1989 | Cabilly et al. |
| 4,927,762 A | 5/1990 | Darfler |
| 4,965,199 A | 10/1990 | Capon |
| 4,975,278 A | 12/1990 | Senter et al. |
| 5,053,394 A | 10/1991 | Ellestad et al. |
| 5,114,721 A | 5/1992 | Cohen et al. |
| 5,122,469 A | 6/1992 | Mather et al. |
| 5,143,844 A | 9/1992 | Abrahmsen et al. |
| 5,202,238 A | 4/1993 | Fell, Jr. et al. |
| 5,204,244 A | 4/1993 | Fell et al. |

(Continued)

FOREIGN PATENT DOCUMENTS

| | | |
|---|---|---|
| CN | 1173878 A | 2/1998 |
| CN | 1176659 A | 3/1998 |

(Continued)

OTHER PUBLICATIONS

Ibragimova and Eade (Biophysical Journal, Oct. 1999, vol. 77, pp. 2191-2198).*
Burgess et al, Journal of Cell Biology vol. 111 Nov. 1990 2129-2138.*
Lazar et al Molecular and Cellular Biology Mar. 1988 vol. 8 No. 3 1247-1252.*
Schwartz et al, Proc Natl Acad Sci USA vol. 84:6408-6411 (1987)).*
Lin et al Biochemistry USA vol. 14:1559-1563 (1975)).*
Brummell et al. (Biochemistry 32:1180-1187 (1993)).*
Kobayashi et al. (Protein Engineering 12:879-844 (1999)).*
Burks et al. (PNAS 94:412-417 (1997)).*
Jang et al. (Molec. Immunol. 35:1207-1217 (1998)).*
Brorson et al. (J. Immunol. 163:6694-6701 (1999)).*
Coleman (Research in Immunol. 145:33-36 (1994)).*

(Continued)

*Primary Examiner* — Lynn Bristol
(74) *Attorney, Agent, or Firm* — Morrison & Foerster LLP

(57) ABSTRACT

The present invention relates to multispecific, especially bispecific antibodies comprising full length antibodies and single chain Fab fragments, methods for their production, pharmaceutical compositions containing the antibodies, and uses thereof.

22 Claims, 16 Drawing Sheets

(56) References Cited

U.S. PATENT DOCUMENTS

| | | |
|---|---|---|
| 5,208,020 A | 5/1993 | Chari et al. |
| 5,264,365 A | 11/1993 | Georgiou et al. |
| 5,362,852 A | 11/1994 | Geoghegan |
| 5,416,064 A | 5/1995 | Chari et al. |
| 5,500,362 A | 3/1996 | Robinson et al. |
| 5,508,192 A | 4/1996 | Georgiou et al. |
| 5,532,142 A | 7/1996 | Johnston et al. |
| 5,591,828 A | 1/1997 | Bosslet et al. |
| 5,635,483 A | 6/1997 | Pettit et al. |
| 5,639,635 A | 6/1997 | Joly et al. |
| 5,641,870 A | 6/1997 | Rinderknecht et al. |
| 5,648,237 A | 7/1997 | Carter et al. |
| 5,663,149 A | 9/1997 | Pettit et al. |
| 5,712,374 A | 1/1998 | Kuntsmann et al. |
| 5,714,586 A | 2/1998 | Kunstmann et al. |
| 5,731,168 A | 3/1998 | Carter et al. |
| 5,739,113 A | 4/1998 | Lee |
| 5,739,116 A | 4/1998 | Hamann et al. |
| 5,747,654 A | 5/1998 | Pastan et al. |
| 5,767,285 A | 6/1998 | Hamann et al. |
| 5,770,701 A | 6/1998 | McGahren et al. |
| 5,770,710 A | 6/1998 | McGahren et al. |
| 5,773,001 A | 6/1998 | Hamann et al. |
| 5,780,588 A | 7/1998 | Pettit et al. |
| 5,798,229 A | 8/1998 | Strittmatter et al. |
| 5,821,333 A | 10/1998 | Carter et al. |
| 5,821,337 A | 10/1998 | Carter et al. |
| 5,824,483 A | 10/1998 | Houston |
| 5,877,296 A | 3/1999 | Hamann et al. |
| 5,932,448 A | 8/1999 | Tso et al. |
| 5,959,083 A | 9/1999 | Bosslet et al. |
| 6,027,888 A | 2/2000 | Georgiou et al. |
| 6,083,715 A | 7/2000 | Georgiou et al. |
| 6,136,564 A | 10/2000 | Kopetzki |
| 6,166,185 A | 12/2000 | Davis et al. |
| 6,239,259 B1 | 5/2001 | Davis et al. |
| 6,350,860 B1 | 2/2002 | Buyse et al. |
| 6,511,663 B1 | 1/2003 | King et al. |
| 6,534,628 B1 | 3/2003 | Nilsson et al. |
| 6,558,672 B1 | 5/2003 | Pastan et al. |
| 6,602,684 B1 | 8/2003 | Umana et al. |
| 6,660,843 B1 | 12/2003 | Feige et al. |
| 6,833,441 B2 | 12/2004 | Wang et al. |
| 6,835,809 B1 | 12/2004 | Liu et al. |
| 6,897,044 B1 | 5/2005 | Braslawsky et al. |
| 6,919,426 B2 | 7/2005 | Boone et al. |
| 6,946,292 B2 | 9/2005 | Kanda et al. |
| 6,982,321 B2 | 1/2006 | Winter |
| 7,129,330 B1 | 10/2006 | Little et al. |
| 7,507,796 B2 | 3/2009 | Little et al. |
| 7,642,228 B2 | 1/2010 | Carter et al. |
| 7,651,688 B2 | 1/2010 | Hanai et al. |
| 7,666,622 B2 | 2/2010 | Sharma et al. |
| 7,695,936 B2 | 4/2010 | Carter et al. |
| 7,919,257 B2 | 4/2011 | Hoogenboom et al. |
| 7,942,042 B2 | 5/2011 | Kawakita et al. |
| 8,216,805 B2 | 7/2012 | Carter et al. |
| 8,227,577 B2 | 7/2012 | Klein et al. |
| 8,242,247 B2 | 8/2012 | Klein et al. |
| 8,268,314 B2 | 9/2012 | Baehner et al. |
| 8,304,713 B2 | 11/2012 | Pradel |
| 8,309,300 B2 | 11/2012 | Jununtual et al. |
| 8,796,424 B2* | 8/2014 | Croasdale et al. ......... 530/387.1 |
| 8,871,912 B2 | 10/2014 | Davis et al. |
| 2002/0155537 A1 | 10/2002 | Carter et al. |
| 2003/0027751 A1 | 2/2003 | Kovesdi et al. |
| 2003/0124129 A1 | 7/2003 | Oliner |
| 2003/0170230 A1 | 9/2003 | Caterer et al. |
| 2003/0176352 A1 | 9/2003 | Min et al. |
| 2003/0195156 A1 | 10/2003 | Min et al. |
| 2003/0219817 A1 | 11/2003 | Zhu et al. |
| 2003/0229023 A1 | 12/2003 | Oliner et al. |
| 2003/0236193 A1 | 12/2003 | Oliner et al. |
| 2004/0018557 A1 | 1/2004 | Qu et al. |
| 2004/0033561 A1 | 2/2004 | O'Keefe et al. |
| 2004/0038339 A1 | 2/2004 | Kufer et al. |
| 2004/0220388 A1 | 11/2004 | Metens et al. |
| 2005/0054048 A1 | 3/2005 | Grasso et al. |
| 2005/0064509 A1 | 3/2005 | Bradbury et al. |
| 2005/0079170 A1 | 4/2005 | Le Gall et al. |
| 2005/0100543 A1 | 5/2005 | Hansen et al. |
| 2005/0152894 A1 | 7/2005 | Krummen et al. |
| 2005/0163782 A1 | 7/2005 | Glaser et al. |
| 2005/0169933 A1 | 8/2005 | Steeves et al. |
| 2005/0186208 A1 | 8/2005 | Fyfe et al. |
| 2005/0238649 A1 | 10/2005 | Doronina et al. |
| 2005/0249722 A1 | 11/2005 | Beliard et al. |
| 2006/0008845 A1 | 1/2006 | Kondejewski et al. |
| 2006/0063921 A1* | 3/2006 | Moulder et al. ........... 530/387.3 |
| 2006/0122370 A1 | 6/2006 | Oliner et al. |
| 2006/0134709 A1 | 6/2006 | Stavenhagen et al. |
| 2006/0160184 A1 | 7/2006 | Hoogenboom et al. |
| 2006/0280747 A1 | 12/2006 | Fuh et al. |
| 2007/0014794 A1 | 1/2007 | Carter et al. |
| 2007/0071675 A1 | 3/2007 | Wu et al. |
| 2007/0071742 A1 | 3/2007 | Fang et al. |
| 2007/0141065 A1 | 6/2007 | Fuh et al. |
| 2007/0178552 A1 | 8/2007 | Arathoon et al. |
| 2007/0269369 A1 | 11/2007 | Gegg et al. |
| 2007/0274985 A1 | 11/2007 | Dubel et al. |
| 2007/0274998 A1 | 11/2007 | Utku |
| 2007/0287170 A1 | 12/2007 | Davis et al. |
| 2008/0063641 A1 | 3/2008 | Huang et al. |
| 2008/0187954 A1 | 8/2008 | Kallmeier et al. |
| 2009/0023811 A1 | 1/2009 | Biadatti et al. |
| 2009/0117105 A1 | 5/2009 | Hu et al. |
| 2009/0155275 A1 | 6/2009 | Wu et al. |
| 2009/0162359 A1 | 6/2009 | Klein et al. |
| 2009/0162360 A1 | 6/2009 | Klein et al. |
| 2009/0175851 A1 | 7/2009 | Klein et al. |
| 2009/0194692 A1 | 8/2009 | Kobaru |
| 2009/0232811 A1 | 9/2009 | Klein et al. |
| 2010/0081796 A1* | 4/2010 | Brinkmann et al. ....... 530/387.3 |
| 2010/0111967 A1* | 5/2010 | Baehner et al. ............ 424/158.1 |
| 2010/0254989 A1 | 10/2010 | Bossenmaier et al. |
| 2010/0256339 A1 | 10/2010 | Bossenmaier et al. |
| 2010/0256340 A1 | 10/2010 | Brinkmann et al. |
| 2010/0316645 A1 | 12/2010 | Imhof-Jung et al. |
| 2010/0322934 A1 | 12/2010 | Imhof-Jung et al. |
| 2010/0322935 A1 | 12/2010 | Croasdale et al. |
| 2011/0054151 A1 | 3/2011 | Lazar et al. |
| 2012/0149879 A1* | 6/2012 | Brinkmann et al. ....... 530/387.3 |
| 2012/0164726 A1 | 6/2012 | Klein et al. |
| 2012/0184718 A1* | 7/2012 | Bruenker et al. ........... 530/387.3 |
| 2012/0225071 A1 | 9/2012 | Klein et al. |
| 2012/0237506 A1 | 9/2012 | Bossenmaier et al. |
| 2012/0237507 A1 | 9/2012 | Bossenmaier et al. |
| 2012/0302737 A1 | 11/2012 | Christensen et al. |
| 2012/0321627 A1 | 12/2012 | Baehner et al. |
| 2013/0022601 A1 | 1/2013 | Brinkmann et al. |
| 2013/0058937 A1 | 3/2013 | Auer et al. |
| 2013/0060011 A1 | 3/2013 | Bruenker et al. |
| 2013/0078249 A1 | 3/2013 | Ast et al. |
| 2013/0156772 A1* | 6/2013 | Bossenmaier et al. ..... 424/136.1 |
| 2013/0266568 A1 | 10/2013 | Brinkmann et al. |
| 2013/0267686 A1 | 10/2013 | Brinkmann et al. |
| 2013/0273054 A1* | 10/2013 | Bossenmaier et al. ..... 424/136.1 |
| 2015/0004166 A1 | 1/2015 | Baehner et al. |
| 2015/0030598 A1 | 1/2015 | Croasdale et al. |
| 2015/0133638 A1 | 5/2015 | Wranik et al. |

FOREIGN PATENT DOCUMENTS

| | | |
|---|---|---|
| CN | 1230239 A | 10/1999 |
| CN | 1603345 A | 4/2005 |
| CN | 101037671 A | 9/2007 |
| CN | 101065151 A | 10/2007 |
| CN | 101205255 A | 6/2008 |
| CN | 101218251 A | 7/2008 |
| CN | 101355966 A | 1/2009 |
| EP | 0 307 434 B1 | 3/1989 |
| EP | 0 307 434 B2 | 3/1989 |
| EP | 0 339 217 B1 | 11/1989 |
| EP | 0 340 109 A2 | 11/1989 |

(56) References Cited

FOREIGN PATENT DOCUMENTS

| | | |
|---|---|---|
| EP | 0 404 097 B1 | 12/1990 |
| EP | 0 425 235 B1 | 5/1991 |
| EP | 0 637 593 A1 | 2/1995 |
| EP | 1 391 213 A1 | 2/2004 |
| EP | 1 870 459 A1 | 12/2007 |
| EP | 2 050 764 B2 | 4/2009 |
| EP | 2 443 154 B1 | 4/2012 |
| JP | 2008-531049 A | 8/2000 |
| RU | 2005/124281 A | 1/2006 |
| WO | WO-87/00195 A1 | 1/1987 |
| WO | WO-90/03430 A1 | 4/1990 |
| WO | WO-90/08187 A1 | 7/1990 |
| WO | WO-90/11294 A1 | 10/1990 |
| WO | WO-91/01133 A1 | 2/1991 |
| WO | WO-91/06305 A1 | 5/1991 |
| WO | WO-92/04053 A1 | 3/1992 |
| WO | WO-93/06217 A1 | 4/1993 |
| WO | WO-93/11161 A1 | 6/1993 |
| WO | WO-93/21232 A1 | 10/1993 |
| WO | WO-94/09131 A1 | 4/1994 |
| WO | WO-94/10202 A1 | 5/1994 |
| WO | WO-94/11026 A2 | 5/1994 |
| WO | WO-94/29350 A2 | 12/1994 |
| WO | WO-94/29350 A3 | 12/1994 |
| WO | 95/09917 | 4/1995 |
| WO | WO-96/27011 A1 | 9/1996 |
| WO | WO-96/27612 A1 | 9/1996 |
| WO | WO-97/01580 A1 | 1/1997 |
| WO | WO-97/14719 A1 | 4/1997 |
| WO | WO-97/028267 A1 | 8/1997 |
| WO | WO-97/028267 C1 | 8/1997 |
| WO | WO-98/45331 A2 | 10/1998 |
| WO | WO-98/45331 A3 | 10/1998 |
| WO | WO-98/45332 A2 | 10/1998 |
| WO | WO-98/45332 A3 | 10/1998 |
| WO | WO-98/050431 A2 | 11/1998 |
| WO | WO-99/37791 A1 | 7/1999 |
| WO | WO-99/54342 A1 | 10/1999 |
| WO | WO-99/66951 A2 | 12/1999 |
| WO | WO-99/66951 A3 | 12/1999 |
| WO | WO-00/24770 A2 | 5/2000 |
| WO | WO-00/24770 A3 | 5/2000 |
| WO | WO-00/29004 A1 | 5/2000 |
| WO | WO-00/35956 A1 | 6/2000 |
| WO | WO-00/61739 A1 | 10/2000 |
| WO | WO-01/77342 A1 | 10/2001 |
| WO | WO-01/90192 A2 | 11/2001 |
| WO | WO-02/02781 A1 | 1/2002 |
| WO | WO-02/051870 A2 | 7/2002 |
| WO | WO-02/088172 A2 | 11/2002 |
| WO | WO-02/092620 A2 | 11/2002 |
| WO | WO-02/092620 A3 | 11/2002 |
| WO | WO-03/012069 A2 | 2/2003 |
| WO | WO-03/030833 A2 | 4/2003 |
| WO | WO-03/030833 A3 | 4/2003 |
| WO | WO-03/035694 A2 | 5/2003 |
| WO | WO-03/035835 A2 | 5/2003 |
| WO | WO-03/035835 A3 | 5/2003 |
| WO | WO-03/055993 A1 | 7/2003 |
| WO | WO-03/057134 A2 | 7/2003 |
| WO | WO-03/057134 A3 | 7/2003 |
| WO | WO-03/066660 A2 | 8/2003 |
| WO | WO-03/097105 A1 | 11/2003 |
| WO | WO-03/106501 A1 | 12/2003 |
| WO | WO-2004/032961 A1 | 4/2004 |
| WO | WO-2004/058298 A1 | 7/2004 |
| WO | WO-2004/065417 A2 | 8/2004 |
| WO | WO-2004/065540 A2 | 8/2004 |
| WO | WO-2004/065540 A3 | 8/2004 |
| WO | WO-2004/072117 A2 | 8/2004 |
| WO | WO-2004/072117 A3 | 8/2004 |
| WO | WO-2004/092215 A2 | 10/2004 |
| WO | WO-2004/092215 A3 | 10/2004 |
| WO | WO-2005/000900 A1 | 1/2005 |
| WO | WO-2005/001025 A2 | 1/2005 |
| WO | WO-2005/004809 A2 | 1/2005 |
| WO | WO-2005/004809 A3 | 1/2005 |
| WO | WO-2005/005635 A2 | 1/2005 |
| WO | WO-2005/005635 A3 | 1/2005 |
| WO | WO-2005/011735 A1 | 2/2005 |
| WO | WO-2005/018572 A2 | 3/2005 |
| WO | WO-2005/018572 A3 | 3/2005 |
| WO | WO-2005/027966 A2 | 3/2005 |
| WO | WO-2005/027966 A3 | 3/2005 |
| WO | WO-2005/035572 A2 | 4/2005 |
| WO | WO-2005-035572 A3 | 4/2005 |
| WO | WO-2005/044853 A2 | 5/2005 |
| WO | WO-2005/044853 A3 | 5/2005 |
| WO | WO-2005/044859 A2 | 5/2005 |
| WO | WO-2005/044859 A3 | 5/2005 |
| WO | WO-2005/063816 A2 | 7/2005 |
| WO | WO-2005/063816 A3 | 7/2005 |
| WO | WO-2005/075514 A2 | 8/2005 |
| WO | WO-2006/020258 A1 | 2/2006 |
| WO | WO-2006/031370 A2 | 3/2006 |
| WO | WO-2006/031370 A3 | 3/2006 |
| WO | WO-2006/034488 A2 | 3/2006 |
| WO | WO-2006/034488 A3 | 3/2006 |
| WO | WO-2006/044908 A2 | 4/2006 |
| WO | WO-2006/044908 A3 | 4/2006 |
| WO | WO-2006/045049 A1 | 4/2006 |
| WO | WO-2006/068953 A2 | 6/2006 |
| WO | WO-2006/068953 A3 | 6/2006 |
| WO | WO-2006/082515 A2 | 8/2006 |
| WO | WO-2006/082515 A3 | 8/2006 |
| WO | WO-2006/089364 A1 | 8/2006 |
| WO | WO-2006/091209 A2 | 8/2006 |
| WO | WO-2006/091209 A3 | 8/2006 |
| WO | WO-2006/093794 A1 | 9/2006 |
| WO | WO-2006/103100 A2 | 10/2006 |
| WO | WO-2006/103100 A3 | 10/2006 |
| WO | WO-2006/113665 A2 | 10/2006 |
| WO | WO-2006/114700 A2 | 11/2006 |
| WO | WO-2006/114700 A3 | 11/2006 |
| WO | WO-2006/116260 A2 | 11/2006 |
| WO | WO-2006/116260 A3 | 11/2006 |
| WO | WO-2007/024715 A2 | 3/2007 |
| WO | WO-2007/031875 A2 | 3/2007 |
| WO | WO-2007/031875 A3 | 3/2007 |
| WO | WO-2007/044887 A2 | 4/2007 |
| WO | WO-2007/044887 A3 | 4/2007 |
| WO | WO-2007/048037 A2 | 4/2007 |
| WO | WO-2007/048037 A3 | 4/2007 |
| WO | WO-2007/068895 A1 | 6/2007 |
| WO | WO-2007/084181 A2 | 7/2007 |
| WO | WO-2007/084181 A3 | 7/2007 |
| WO | WO-2007/095338 A2 | 8/2007 |
| WO | 2007/109254 | 9/2007 |
| WO | WO-2007/089445 A2 | 9/2007 |
| WO | WO-2007/089445 A3 | 9/2007 |
| WO | 2007/110205 | 10/2007 |
| WO | WO-2008/005828 A2 | 1/2008 |
| WO | WO-2008/005828 A3 | 1/2008 |
| WO | 2008/017963 | 2/2008 |
| WO | WO-2008/077077 A2 | 6/2008 |
| WO | WO-2008/077077 A3 | 6/2008 |
| WO | 2008/077546 | 7/2008 |
| WO | WO-2008/100624 A2 | 8/2008 |
| WO | WO-2008/100624 A3 | 8/2008 |
| WO | WO-2008/132568 A2 | 11/2008 |
| WO | WO-2008/132568 A3 | 11/2008 |
| WO | WO-2009/018386 A1 | 2/2009 |
| WO | WO-2009/021745 A1 | 2/2009 |
| WO | WO-2009/021754 A2 | 2/2009 |
| WO | WO-2009/021754 A3 | 2/2009 |
| WO | WO-2009/023843 A1 | 2/2009 |
| WO | WO-2009/030780 A2 | 3/2009 |
| WO | WO-2009-030780 A3 | 3/2009 |
| WO | WO-2009/032782 A2 | 3/2009 |
| WO | WO-2009/032782 A3 | 3/2009 |
| WO | WO-2009/080251 A1 | 7/2009 |
| WO | WO-2009/080252 A1 | 7/2009 |
| WO | WO-2009/080253 A1 | 7/2009 |
| WO | WO-2009/080254 A1 | 7/2009 |

(56) References Cited

FOREIGN PATENT DOCUMENTS

| WO | WO-2009/126944 A1 | 10/2009 |
|---|---|---|
| WO | 2010/034441 | 4/2010 |
| WO | 2010/040508 | 4/2010 |
| WO | WO-2010/065882 A1 | 6/2010 |
| WO | WO-2010/112193 A1 | 10/2010 |
| WO | WO-2010/112194 A1 | 10/2010 |
| WO | WO-2010/115552 A1 | 10/2010 |
| WO | WO-2010/115589 A1 | 10/2010 |
| WO | WO-2010/115589 A8 | 10/2010 |
| WO | WO-2010/136172 A1 | 12/2010 |
| WO | WO-2010/145792 A1 | 12/2010 |
| WO | WO-2010/145793 A1 | 12/2010 |
| WO | WO-2011/028952 A1 | 3/2011 |
| WO | WO-2011/034605 A2 | 3/2011 |
| WO | WO-2011/034605 A3 | 3/2011 |
| WO | WO-2011/133886 A2 | 10/2011 |
| WO | WO-2012/025525 A1 | 3/2012 |
| WO | WO-2012/025530 A1 | 3/2012 |
| WO | WO-2012/116927 A1 | 9/2012 |
| WO | WO-2013/026833 A1 | 2/2013 |
| WO | WO-2010/069532 A1 | 6/2013 |
| WO | WO-2013/119966 A2 | 8/2013 |
| WO | WO-2013/174873 A1 | 11/2013 |

OTHER PUBLICATIONS

Dufner (Trends Biotechnol. 24(11):523-29 (2006)).*
Hust, et al., "Single Chain Fab (scFab) Fragment", BMC Biotechnology (2007) vol. 7, No. 1, pp. 14, Biomed Central Ltd. London, GB, XP021023594.
Mueller, et al., "Bispecific Antibodies", Handbook of Therapeutic Antibodies; Part III, Chapter 2, Feb. 1, 2008, Stefan Duebel, Weinheim, pp. 345-378, XP007909504.
Lu, et al., "A Fully Human Recombinant IgG-like Bispecific Antibody to Both the Epidermal Growth Factor Receptor and the Insulin-like Growth Factor Receptor for Enhanced Antitumor Activity" Journal of Biological Chemistry, American Society for Biochemistry and Molecular Biology Inc., Birmingham, US, vol. 280, No. 20, May 20, 2005, pp. 19665-19672, XP002516978.
Hartog et al., "The insulin-like growth factor 1 receptor in cancer: Old focus, new future" European Journal of Cancer, Pergamon Press, Oxford, GB, vol. 43, No. 13, Aug. 23, 2007, pp. 1895-1904, XP022208925.
Merchant et al., "An efficient route to human bispecific IgB" Nature Biotechnology, Nature Publishing Group, New York, NY, US, vol. 16, No. 7, Jul. 1, 1998, pp. 677-681, XP002141015.
Liu, et al., "Clinical and imaging diagnosis of primary hepatic lymphoma" J First Mil Med Univ., 2005:25(10), pp. 1290-1297.
Hust, M. et al., *BMC Biotechnology* 7:1-15 (Mar. 8, 2007).
(Taiwanese Search Report in Corres App 099110151 Sep 19, 2012).
Aggarwal et al. (Jan. 22, 2008). "Fibroblast Activation Protein Peptide Substrates Identified from Human Collagen I Derived Gelatin Cleavage Sites," Biochemistry 47(3):1076-1086.
Anonymous. (1997). "Production in yeasts of stable antibody fragments," Expert Opinion on Therapeutic Patents 7(2):179-183.
Atwell et al., "Stable heterodimers from remodeling the domain interface of a homodimer using a phage display library" J. Mol. Biol. 270 (1): 26-35 (1997).
Avgeris et al. (May 2010). "Kallikrein-related peptidase genes as promising biomarkers for prognosis and monitoring of human malignancies," Biol. Chem 391(5):505-511.
Bao et al. (Jul. 2010). "HER2-mediated upregulation of MMP-1 is involved in gastric cancer cell invasion," Arch Biochem Biophys 499(1-2):49-55.
Barnes et al., "Advanced in animal cell recombinant protein production: GS-NSO expression system" Cytotechnology 32 (2): 109-23 (Feb. 2000).
Barnes et al., "Characterization of the stability of recombinant protein production in the GS-NSO expression system" Biotechnol Bioeng. 73(4): 261-70 (May 2001).

Bera, T.K. et al. (Aug. 21, 1998). "A bivalent disulfide-stabilized Fv with improved antigen binding to erbB2," J. Mol. Biol. 281(3):475-483.
Boado, R.J. et al. (Feb. 15, 2010). "IgG-single chain Fv fusion protein therapeutic for Alzheimer's disease: Expression in CHO cells and pharmacokinetics and brain delivery in the rhesus monkey," Biotechnology and Bioengineering 105(3):627-635.
Boerner et al., "Production of Antigen—Specific Human Monoclonal Antibodies From In Vitro-Primed Human Splenocytes" J Immunol. 147(1): 86-95 (Jul. 1991).
Borgstrom, P., et al., Complete Inhibition of Angiogenesis and Growth of Microtumors by Anti-Vascular Endothelial Growth Factor Neutralizing Antibody: Novel Concepts of Angiostatic Therapy from Intravital Videomicroscopy; Cancer Research (1996) 56, 4032-4039.
Briggs et al. (Jan. 2010). "Cystatin E/M suppresses legumain activity and invasion of human melanoma" BMC Cancer 10:17.
Brinkmann et al. "Disulfide-stabilized Fv fragments," Chapter 14 in 2 in Antibody Engineering, Kontermaan et al. eds., vol. 2, Springer-Verlag, Berlin Heidelberg, Germany, pp. 181-189, (Apr. 30, 2010).
Brinkmann, U. et al. (1993). "A recombinant immunotoxin containing a disulfide-stabilized Fv fragment," PNAS 90(16):7538-7542.
Brüggemann et al., "Comparison of the effector functions of human immunoglobulins using a matched set of chimeric antibodies" J Exp Med. 166(5):1351-61 (Nov. 1987).
Brüggmann et al., "Designer Mice: The Production of Human Antibody Repertoires in Transgenic Animals" *Year in Immuno.* 7:33-40 (1993).
Brunhouse et al., "Isotypes of IgG: comparison of the primary structures of three pairs of isotypes which differ in their ability to activate complement" Mol Immunol. 16(11): 907-917 (Nov. 1979).
Burton et al., "The Clq Receptor Site on Immunoglobulin G." Nature 288(5789): 338-344 (Nov. 27, 1980).
Caron et al. "Engineered humanized dimeric forms of IgG are more effective antibodies," J. Exp. Med. 176(4):1191-1195, (Oct. 1, 1992).
Carro, E. et al. "Serum insulin-like growth factor I regulates brain amyloid-beta levels," Nature Medicine 8(12):1390-1397, (2002, e-pub. Nov. 4, 2002).
Carter et al., "Humanization of an Anti-pI85her2 Antibody for Human Cancer Therapy" Proc Natl Acad Sci USA. 89(10): 4285-4289 (May 1992).
Carter. "Bispecific human IgG by design," Immunol. Methods 248:7-15. 2001.
Chan, L.A. et al. "Variable Region Domain Exchange in Human IgGs Promotes Antibody Complex Formulation with Accompanying Structural Changes and Altered Effector Functions," Molecular Immunology 41:5 (2004) pp. 527-538.
Chitnis et al. "The type 1 insulin-like growth factor receptor pathway," Clin. Cancer Res. 14(20):6364-6370, (Oct. 15, 2008).
Chung, D.E. et al. "Development of a novel albumin-binding prodrug that is cleaved by urokinase-type-plasminogen activator (uPA)," Bioorg Med Chem Lett. 16(19):5157-5163 (Oct. 1, 2006).
Cohen et al., "Nonchromosomal Antibiotic Resistance in Bacteria: Genetic Transformation of *Escherichia coli* by R-Factor DNA" Proc. Natl. Acad. Sci. USA 69(8):2110-2114 (Aug. 1972).
Cole et al., "The EBV-Hybridoma Technique and Its Application to Human Lung Cancer" Monoclonal Antibodies and Cancer Therapy. New York: Alan R. Liss, Inc. pp. 77-96 (1985).
Coloma and Morrison, "Design and production of novel tetravalent bispecific antibodies" Nature Biotechnology 15(2) :159-163 (Feb. 1997).
Cordingley et al. (1990). "Substrate requirements of human rhinovirus 3C protease for peptide cleavage in vitro," J. Biol. Chem. 265(16):9062-9065.
Cortesio et al. (Mar. 10, 2008). "Calpain 2 and PTP1 B function in a novel pathway with Src to regulate invadopodia dynamics and breast cancer cell invasion," J. Cell Biol. 180(5):957-971.
Coxon, A., et al., Combined Treatment of Angiopoietin and VEGF Pathway Antagonists Enhances Antitumor Activity in Preclinical Models of Colon Carcinoma; 9th AACR Annual Meeting, Apr. 2008, Abstract #1113.
Crawford et al. (Jun. 2002). "Matrix metalloproteinase-7 is expressed by pancreatic cancer precursors and regulates acinar-to-ductal metaplasia in exocrine pancreas," J. Clin. Invest. 109(11):1437-1444.

(56) References Cited

OTHER PUBLICATIONS

Cudic et al. (Aug. 2009). "Extracellular proteases as targets for drug development," Curr. Protein Pept Sci 10(4):297-307.
Cullen et al. (Apr. 2010). "Granzymes in cancer and immunity," Cell Death Differ 17(4):616-623.
Davies et al., "Expression of GnTIII in a Recombinant Antl•CD20 CHO Production Cell L1ne: Expression of Antibodies with Altered Glycoforms Leads to an Increase in ADCC Through Higher Affinity for FcγRIII," Biotechnol. Bioeng. 74:288-294 (2001).
Deyev. (2008). "Multivalency: the hallmark of antibodies used for optimization of tumor targeting by design," Bioessays 30(9):904-918.
Donaldson et al. "Design and development of masked therapeutic antibodies to limit off-target effects: Application to anti-EGFR antibodies," Cancer Biology & Therapy (2009). 8:2147-2150.
Durocher et al., "High-level and high-throughput recombinant protein production by transient transfection of suspension-growing human 293-EBNA1 cells" Nucleic Acids Research•30(2 e9):nine pages. (2002).
Edelman et al., "The covalent structure of an entire yG immunoglobulin molecule" Proc. Natl. Acad. Sci. USA 63:78-85 (1969).
Fischer et al., "Bispecific Antibodies: Molecules that Enable Novel Therapeutic Strategies" Pathobiology 74:3-14 (2007).
Flatman et al. "Process analytics for purification of monoclonal antibodies," J. Chromatogr B 848:79-87, (2007).
Galamb et al. (2008). "Inflammation, adenoma and cancer: objective classification of colon biopsy specimens with gene expression signature," Dis Markers 25(1):1-16.
Geisse et al., "Eukaryotic Expression Systems: A comparison" Protein Expression and Purification 8:271-282 (1996).
Gerspach et al. "Target-selective activation of a TNF prodrug by urokinase-type plasminogen activator (uPA) mediated proteolytic processing at the cell surface," Cancer Immunol. Immunother 55:1590-1600 (2006).
Gold, D., et al.; A Novel Bispecific, Trivalent Antibody Construct for Targeting Pancreatic Carcinoma; Cancer Res [g] (2008) 68:12; 4819; XP-002541923.
Goldberg et al., "Bi-Specific Antibodies that Bind Specific Target Tissue and Targeted Conjugates," Derwent Information Ltd., 12 pages (2012).
Graham et al., "A new technique for the assay of infectivity of human adenovirus 5 DNA" Virology 52 (2) :456-467 (1973).
Grote, M et al., "Blspeciific Antibody Derivatives Based on Full-Length IgG Formats," Chapter 16 in *Methods Molecular Biology* 901:247-263 (2012).
Henry et al. (Mar. 15, 2007). "Clinical implications of fibroblast activation protein in patients with colon cancer," Clin Cancer Res. 13(6):1736-1741.
Hezareh et al., "Effector Function Activities of a Panel of Mutants of a Broadly Neutralizing Antibody against Human Immunodeficiency Virus Type 1" Journal of Virology 75(24) :12161-12168 (Dec. 2001).
Hollander, N. (Mar. 2009). "Bispecific antibodies for cancer therapy," Immunotherapy 1(2):211-222.
Holliger et al., "Engineered antibody fragments and the rise of single domains" Nat Biotechnol. 23 (9): 1126-1136 (Sep. 2005).
Hoogenboom and Winter, "By-passing immunisation. Human antibodies from synthetic repertoires of germline $V_H$ gene segments rearranged in Vitro" J Mol Biol. 227 (2) :381-388 (Sep. 20, 1992).
Idusogie et al., "Mapping of the Clq Binding Site on Rituxan, a Chimeric Antibody with a Human IgG1 Fc" The Journal of Immunology 164:4178-4184 (2000).
International Search Report mailed on Dec. 6, 2011, for PCT Patent Application No. PCT/EP2011/064476 filed on Aug. 23, 2011, seven pages.
International Search Report mailed on Dec. 6, 2011, for PCT Patent Application No. PCT/EP2011/064468 filed on Aug. 23, 2011, seven pages.
Jakobovits et al., "Analys1s of Homozygous Mutant Chimeric Mice: Deletion of the Immunoglobulin Heavy-Chain Joining Region Blocks B-cell Development and Antibody Production" Proc. Natl. Acad. Sci. USA 90(6) :2551-2555 (Mar. 15, 1993).
Jakobovits et al., "Germ-.line Transmission and Expression of a Human-derived Yeast Artificial Chromosome" Nature 362:255-258 (Mar. 1993).
Jefferis et al., "IgG-Fc-mediated effector functions: molecular definition of interaction sites for effector ligands and the role of glycosylation" Immunol Rev. 163:59-76 (1998).
Jendryko, N., et al., Simultaneous, Phenotypic Knockout of VEGF-R2 and Tie-2 With an Intradiabody Enhances Antiangiogenic Effects In Vivo; Therapieoptimierung and Risikostratifizierung, Scripps Research Institute, (2006) 218: 143-151.
Jia, L. et al. (Jun. 29, 2010). "A novel trifunctional IgG-like bispecific antibody to inhibit HIV-1 infection and enhance lysis of HIV by targeting activation of complement," Virology Journal 7(142):1-4.
Johnson et al., "Kabat Database and its applications: 30 years after the first variability plot" Nucleic Acids Research 28(1) :214-218 (2000).
Kabat et al., "Evolutionary and structural influences on light chain constant ($C_L$) region of human and mouse immunoglobulins" Proc. Natl. Acad. Sci. USA 72(7) :2785-2788 (Jul. 1975).
Kabat et al., Sequences of Proteins of Immunological Interest (Table•of Contents and Introduction), 5th edition, Bethesda, MD:Public Health Service, NIH vol. 1 (1991).
Karadag et al. (Apr. 2006). "ADAM-9 (MDC-9/meltrin-γ), a member of the a disintegrin and metalloproteinase family, regulates myeloma-cell-induced interleukin-6 production in osteoblasts by direct interaction with the $α_vβ_5$ integrin," Blood 107(8):3271-3278.
Kaufman, R.J., "Overview of Vector Design for Mammalian Gene Expression" Molecular Biotechnology 16:151-161 (2000).
Kazam et al. (19950. "Hepsin, a putative membrane-associated serine protease, activates human factor VII and initiates a pathway of blood coagulation on the cell surface leading to thrombin formation," JBC 270:66-72.
Kim, K.J. et al., Inhibition of Vascular Endothelial Growth Factor-Induced Angiogenesis Suppresses Tumour Growth In vivo, Nature, vol. 362 (1993) 841-844.
Kleinschmidt, M. et al. (Mar. 21, 2003). "Design of a modular immunotoxin connected by polyionic adapter peptides," J. Mol. Biol. 327(2):445-452.
Kobayshi et al., "Similarities in the Biodistribution of Iodine-Labeled Anti-Tac Single-Chain Disulfide-Stabilized Fv Fragment and Anti-Tac Disulfide-Stabilized Fv Fragment" Nuclear Medicine & Biology 25:387-393 (1998).
Kodukula, K. et al. "Biosynthesis of phosphatidylinositol glycan-anchored membrane proteins. Design of a simple protein substrate to characterize the enzyme that cleaves the COOH-terminal signal peptide," *The Journal of Biological Chemistry* 266(7):4464-4470 (Mar. 5, 1991).
Kontermann, R. et al. (Apr. 30, 2010). "Chapter 14: Disulfide-stabilized Fv fragments," Antibody Engineering 2:181-189.
Lamkanfi et al.. (Jan. 2009). "Inflammasomes: guardians of cytosolic sanctity," Immunol. Rev. 227(1):95-105.
Lee et al. (Jun. 16, 2009). "Using substrate specificity of antiplasmin-cleaving enzyme for fibroblast activation protein inhibitor design," Biochemistry 48(23):5149-5158.
Leeman et al. "The Structure, Regulation, and Function of Human Matrix Metalloproteinase-13," Crit. Rev Biochem Mol. Biol. (2002), 37(3):149-166.
Lifely et al., "Glycosylation and Biological Activity of CAMPATH-1H Expressed in Different Cell Lines and Grown Under Different Culture Conditions." Glycobiology 5(8) :813-822 (Dec. 1995).
Liang, W.C., et al., Cross-species Vascular Endothelial Growth Factor (VEGF)-blocking Antibodies Completely Inhibit the Growth of Human Tumor Xenografts and Measure the Contribution of Stromal VEGF; Journal of Biological Chemistry, 281:2 (2006) 951-961.
Liotta et al. "Metastatic Potential Correlates with Enzymatic Degradation of Basement Membrane Collagen," Nature 284(5751) 67-68, (Mar. 6, 1980).
Lopez-Otin et al. (Apr. 2010). "The regulatory crosstalk between kinases and proteases in cancer," Nat. Rev. Cancer 10(4):278-292.
Love et al, "Recombinant antibodies possessing novel effector functions" Methods in Enzymology 178:515-527 (1989).

(56) References Cited

OTHER PUBLICATIONS

Lu et al. (Aug. 2009). "ADAMTS1 and MMP1 proteolytically engage EGF-like ligands in an osteolytic signaling cascade for bone metastasis," Genes Dev. 23(16):1882-1894.
Lukas et al., "Inhibition of C1-Mediatea Immune Hemolysls by Monomeric arid Dimeric Peptides from the Second Constant Domain of Human Immunoglobulin G1" The Journal of Immunology 127 (6) :2555-2560 (Dec. 1981).
Lund et al., "Oligosaccharide-protein interactions in IgG can modulate recognition by Fcy receptors" FASEB Journal 9:115-119 (1995).
Makrides, S.C., "Components of Vectors for Gene Transfer and Expression in Mammalian Cells" Protein Expression and Purification 17:183-202 (1999).
Mamoune et al. (Aug. 2003). "Calpain-2 as a target for limiting prostate cancer invasion," Cancer Res. 63(15):4632-4640.
Marks et al., "By-Passing Immunization: Human Antibodies From V-gene Librarles Displayed on Phage" J Mol Biol. 222(3) :581-597 (Dec. 5, 1991).
Marvin et al. "Recombinant approaches to IgG-like bispecific antibodies," Acta Pharmacol. Sin 26:649-658. (2005).
Marvin et al. "Bispecific antibodies for dual-modality cancer therapy: killing two signaling cascades with one stone," Curr. Opin. Drug Discov. Dev. 9:184-193, (2006).
Matrisian et al. (Oct. 1999). "Cancer biology: extracellular proteinases in malignancy," Curr. Biol. 9(20):R776-R778.
Meissner et al., "Transient Gene Expression: Recombinant Protein Production with Suspension-Adapted HEK293-EBNA Cells" Biotechnology and Bioengineering 75:197-203 (2001).
Melnyk, 0., et al., Vascular Endothelial Growth Factor Promotes Tumor Dissemination by a Mechanism Distinct from Its Effect on Primary Tumor Growth; Cancer Research, 56 (1996) 921-924.
Michaelson, J.S. et al. (Mar. 2009, e-pub. Mar. 11, 2009). "Antitumor activity of stability-engineered IgG-like bispecific antibodies targeting TRAIL-R2 and LTβR," MAbs 1(2):128-141.
Milstein and Cuello, "Hybrid Hybridomas and Their Use in Immunohistochemistry" Nature 305: 537-540 (Oct. 6,1983).
Miller et al. "Design, Construction, and In Vitro Analyses of Multivalent Antibodies," *J. Immunol.* 170:4854-4861 (2003).
Mimura et al., "Role of Oligosaccharide Residues of IgG1-Fc in FcγRIIb Binding" The Journal of Biological Chemistry 276(49): 45539-45547 (Dec. 7, 2001).
Minn et al. (Jul. 2005). "Genes that Mediate Breast Cancer Metastasis to Lung," Nature 436(7050):518-524.
Morgan et al., "The N-terminal End of the $C_H2$ Domain of Chimeric Human IgG1 anti-HLA-DR is Necessary for Clq, FcyRIII Binding" Immunology 86:319-324 (1995).
Morrison et al., "Chimeric Human Antibody Molecules: Mouse Antigen-Binding Domains with Human Constant Region Domains" Proc. Natl. Acad. Sci. USA 81(21) :6851-6855 (Nov. 1984).
Morrison, S. et al. "Variable region domain exchange influences the functional properties of IgG" Journal of Immunology, American Association of Immunologiest 160:2802-2808 (Jan. 1, 1998).
Morrison et al. "Two Heads are Better than One" Nature Biotechnology 25(11) :1233-1234 (Nov. 2007).
Morrison. "Success in Specification" Nature 368:812-813 (Apr. 1994).
Mukhopadhyay et al. (2010). "Matrix metalloproteinase-12 is a therapeutic target for asthma in children and young adults," J Allergy Clin Immunol. 126:70-76.
Muller, K.M. et al. "The first constant domain (CH1 and C1) of an antibody used as heterodimerization domain for bispecific miniantibodies," FEBS Letters 422:259-264 (1998).
Mueller et al. "Recombinant Bispecific Antibodies for Cellular Cancer Immunotherapy," Current Opinion in Molecular Therapeutics 9:319-326 (2007).
Netzel-Arnett et al. (Apr. 15, 1991). Sequence Specificities of Human Fibroblast and Neutrophil Collagenases, J. Biol. Chem. (Apr. 15, 1991) 266(11):6747-6755.

Netzel-Arnett et al. (1993)."Comparative sequence specificities of human 72- and 92-kDa gelatinases (type IV collagenases) and PUMP (matrilysin)," Biochemistry (Jun. 29, 1993) 32(25):6427-6432.
Neuberger et al., "A hapten-specific chimaeric IgE antibody with human physiological effector function," Nature 314:268-270 (Mar. 21, 1985).
Niwa et al. "IgG subclass-independent improvement of antibody-dependent cellular cytotoxicity by fucose removal from Asn297-linked oligosaccharides," J. Immunol. Methods 306:151-160, (2005).
Norderhaug et al., "Versatile Vectors for Transient and Stable Expression of Recombinant Antibody Molecules in Mammalian Cells" Journal of Immunological Methods 204:77-87 (1997).
Ohno, S. et al. (May 1985). "Antigen-binding specificities of antibodies are primarily determined by seven residues of VH," *PNAS* 82(9):2945-2949.
Oliner, J., et al., Suppression of Angiogenesis and Tumor Growth by Selective Inhibition of Angiopoietin-2; Cancer Cell (2004) vol. 6, 507-516.
Orcutt, K.D. et al. (Apr. 2010, e-pub. Dec. 17, 2009). "A modular IgG-scFv bispecific antibody topology," Protein Engineering, Design & Selection 23(4):221-228.
Orlandi et al., "Cloning Immunoglobulin Variable Domains for Expression by the Polymerase Chain Reaction" Proc. Natl. Acad. Sci. USA 86:3833-3837 (May 1989).
Pace et al., "How to Measure and Predict the Molar Absorption Coefficient of a Protein" Protein Science 4(11): 2411-2423 (Nov. 1995).
Pakula, A.A. et al. (1989). "Genetic analysis of protein stability and function," *Annu. Rev. Genet.* 23:289-310.
Plückthun, A. et al. (1997). "New Protein Engineering Approaches to Multivalent and Bispecific Antibody Fragments," *Immunotechnology* 3:83-105.
PreScission Protease, GE Healthcare Catalogue No. 27/0843-01, located at http://www.gelifesciences.com/webapp/wcs/stores/servlet/productByld/en/GELifeScience, last visited on Jul. 10, 2013, one page.
Radaev et al., "Recognition of IgG by Fcy Receptor" *The Journal of Biological Chemistry* 276(19): 16478-16483 (May 11, 2001).
Rajgopal et al., "A Form of Anti-Tac(Fv) Which is Both Single-chain and Disulfide Stabilized: Comparison with its single chain and Disulfide-stabilized Homologs" Protein Engineering 10(12): 1453-1459 (1997).
Raju, T.S., "Glycosylation Variations with Expression Systems and Their Impact on Biological Activity of Therapeutic Immunoglobulins" BioProcess International 1(4): 44-53 (Apr. 2003).
Rawlings. (2009, e-pub. Nov. 2, 2009). "A large and accurate collection of peptidase cleavages in the *MEROPS* database," Database (Oxford), pp. 1-14.
Reiter et al. (1994). "Improved binding and antitumor activity of a recombinant anti-erbB2 immunotoxin by disulfide stabilization of the Fv fragment," JBC 269:18327-18331.
Reiter et al. "Cytotoxic and antitumor activity of a recombinant immunotoxin composed of disulfide-stabilized anti-Tac Fv fragment and truncated *Pseudomonas* exotoxin," International Journal of Cancer 58:142-149, (1994).
Reiter et al. (1994). "Antitumor activity and pharmacokinetics in mice of a recombinant immunotoxin containing a disulfide-stabilized Fv fragment," Cancer Research 54:2714-2718.
Reiter, Y. et al. (Feb. 1, 1996). "Antibody engineering of recombinant Fv immunotoxins for improved targeting of cancer: disulfide-stabilized Fv immunotoxins," Clin. Cancer Res. 2(2):245-252.
Reiter et al. (1995). "Disulfide stabilization of antibody Fv: computer predictions and experimental evaluation," Protein Engineering 8:1323-1331.
Reiter et al. "Construction of a functional disulfide-stabilized TCR Fv indicates that antibody and TCR Fv frameworks are very similar in structure," Immunity 2:281-287, (1995).
Reiter, Y. et al. "Engineering antibody Fv fragments for cancer detection and therapy: disulfide-stabilized Fv fragments," Nature Biotechnology 14:1239-1245 (1996).

(56) References Cited

OTHER PUBLICATIONS

Ridgway et al., "'Knobs-into-holes' Engineering of Antibody $C_H3$ Domains for Heavy Chain Heterodimerization" Protein Engineering 9(7):617-621 (1996).
Riechmann et al., "Reshaping Human Antibodies for Therapy" Nature 332:323-327 (Mar. 24, 1988).
Rossi, E.A. et al. "Multivalent Anti-CD20/Anti-CD22 Bispecific Antibody Fusion Proteins Made by the DNL Method Show Potent Lymphoma Cytotoxicity," Blood, American Society of Hematology 8:11 (2006) pp. 707A.
Roitt et al., "Immunology" English Translation by McElroy Translation Company, Moscow "Mir" (2000), p. 110, two pages.
Routier et al., "The Glycosylation Pattern of a Humanized IgGI Antibody (D1.3) Expressed in CHO Cells" Glycoconjugate Journal 14:201-207 (1997).
Ruppert et al. "Protease levels in breast, ovary and other gynecological tumor tissues: prognostic importance in breast cancer," Cancer Detect. Prev. (1997) 21)5):452-459.
Sambrook et al. Molecular Cloning: A Laboratory Manual "The Table of Contents" Cold Spring Harbor, New York: Cold Spring Harbor Laboratory Press (1989).
Schaefer, W. et al. "Immunoglobulin domain crossover as a generic approach for the production of bispecific IgG antibodies," *Proc. Natl. Acad. ScL U.S.A.* 108(27):11187-11192, (Jul. 5, 2011, e-pub. Jun. 20, 2011).
Schlaeger, E., "The Protein Hydrolysate, Primatone RL, is a Cost Effective Multiple Growth Promoter of Mammalian Cell Culture in Serum-containing and Serum-free Media and Displays Anti apoptosis Properties" Journal of Immunological Methods194:191-199 (1996).
Schlaeger et al., "Transient Gene Expression in Mammalian Cells Grown in Serum-free Suspension Culture" Cytotechnology 30:71-83 (1999).
Schmidt et al., "Suppression of Metastasis Formation by a Recombinant Single Chain Antibody-Toxin Targeted to Full-length and Oncogenic Variant EGF Receptors" Oncogene 18:1711-1721, (1999).
Schmiedl, A. et al. (Oct. 2000). "Expression of a bispecific dsFv-dsFv' antibody fragment in *Escherichia coli*," Protein Engineering 13(10):725-734.
Schoonjans, et al., Fab Chains as an Efficient Heterodimerization Scaffold for the Production of Recombinant Bispecific and Trispecific Antibody Derivatives. Journal of Immunology, 2000. vol. 165, pp. 7050-7057.
Scott et al. (Nov. 2010). "Biologic protease inhibitors as novel therapeutic agents," 92(11):1681-1688.
Shen, J. et al. (Apr. 21, 2006, e-pub. Feb. 15, 2006). "Single variable domain-IgG fusion: a novel recombinant approach to Fc domain-containing bispecific antibodies," J. of Biological Chemistry 281(16):10706-10714.
Shen et al., "Single Variable Domain Antibody as a Versatile Building Block for the construction of IgG-like Bispecific Antibodies" Journal of Immunological Methods 318:65-74 (2007).
Shields et al., "High Resolution Mapping of the Binding Site on Human IgG1 for FcγRI, FcγRII, FcγRIII and FcRn and Design of IgG1 Variants with Improved Binding to the FcγR" Journal of Biological Chemistry 276 (9) :6591-6604 (2001).
Shields et al., "Lack of Fucose on Human IgG1 N-Linked Oligosaccharide Improves Binding to Human FcγRIII and Antibody-dependent Cellular Toxicity" J Biol Chem. 277(30):26733- 26740 (Jul. 26, 2002).
Shinkawa et al. "The Absence of Fucose but Not the Presence of galactose or Bisecting N-Acetylglucosamine of Human IgG1 Complex-Type Oligosaccharides Shows the Critical Role of Enhancing Antibody-Dependent Cellular cytotoxicity," J. Biol. Chem. 278 (5) 3466-3473, (2003).
Simmons, L. et al., "Expression of full- length immunoglobulins in *Escherichia coli*: Rapid and Efficient production of aglycosylated antibodies" Journal of Immunological Methods 263:133-147 (2002).
Simon et al., "Antibody Domain Mutants Demonstrate Autonomy of the Antigen Binding Site" The EMBO Journal 9(4):1051-1056 (1990).
Singer, M. and Berg, P. "Genes and genomes," Moscoer, MIR 1(1998) 63-64 (With English Translation.).
Stetler-Stevenson et al. (1994-1995). "Progelatinase A activation during tumor cell invasion," Invasion Metastasis 14(1-6):259-268.
Stevenson et al. "A chimeric antibody with dual Fc regions (*bis*FabFc) prepared by manipulations at the IgG hinge," Anticancer Drug Des. 3(4):219-230, (Mar. 1989).
Thommesen et al., "Lysine 322 in the Human IgG3 $C_H2$ Domain is Crucial for Antibody Dependent Complement Activation" Molecular Immunology 37:995-1004 (2000).
Tripathi et al. (2008). Laminin-332 is a substrate for hepsin, a protease associated with prostate cancer progression, JBC 283:30576-30584.
Umana et al., "Engineered Glycoforms of an Antineuroblastoma IgG1 with Optimized Antibody-Dependent Cellular Cytotoxic Activity" Nature Biotechnology 17(2): 176-180 (Feb. 1999).
Van Dijk and Van De Winkelm, "Human antibodies as next generation therapeutics" Curr Opin Chem Biol. 5(4): 368-74 (Aug. 2001).
Van Spriel et al. "Immunotherapeutic Perspective for Bispecific Antibodies," *Immunology Today* 21(8):391-397, (Aug. 2000).
Van't Veer et al. (Jan. 2002). "Gene expression profiling predicts clinical outcome of breast cancer," Nature 415(6871):530-536.
Vazquez-Oritz et al. (Jun. 30, 2005). "Overexpression of cathepsin F, matrix metalloproteinases 11 and 12 in cervical cancer," BMC Cancer 5:68.
Velasco et al. (Oct. 28, 1994). "Human cathepsin O. Molecular cloning from a breast carcinoma, production of the active enzyme in *Escherichia coli*, and expression analysis in human tissues," J. Biol Chem 269(43):27136-27142.
Veveris-Lowe et al. (2007). Seminal Fluid Characterization for Male Fertility and Prostate Cancer: Kallikrein-Related Serine Proteases and whole Proteome Approaches, Semin Thromb Hemost. 33(1):87-99.
Vijayalakshmi, M., "Antibody Purification Methods" Applied Biochemistry and Biotechnology 75:93-102 (1998).
Walker et al. (1994). "Efficient and Rapid Affinity Purification of Proteins Using Recombinant Fusion Proteases," Bio/Technology 12:601-605.
Warren, R.S., et al., Regulation of Vascular Endothelial Growth Factor of Human Colon Cancer Tumorigenesis in a Mouse Model of Experimental Liver Metastasis; J. Clin. Invest., vol. 95 (1995) 1789-1797.
Webber et al. "Preparation and characterization of a disulfide-stabilized Fv fragment of the anti-Tac antibody: comparison with its single-chain analog," Molecular Immunology 32:249-258.
Werner et al., "Appropriate Mammalian Expression Systems for Biopharmaceuticals" Drug Research 48(8):870-880 (1998).
Wielockx et al. (Apr.-Jun. 2004). "Matrilysin (matrix metalloproteinase-7): a new promising drug target in cancer and inflammation?" Cytokine Growth Factor Rev. 15(2-3):111-115.
Willems et al., "Optimizing Expression and Purification from Cell Culture Medium of Trispecific Recombinant Antibody Derivatives" Journal of Chromatography B 786:161-176 (2003).
Woof et al., "Human Antibody-FC Receptor Interactions Illuminated by Crystal structures" Nat. Rev. Immunol. 4:89-99 (2004).
Wright and Morrison, "Effect of Glycosylation on Antibody Function: Implications for Genetic Engineering" Trends in Biotechnology 15:26-32 (1997).
Wright et al. (Aug. 2010). "ADAM28: a potential oncogene involved in asbestos-related lung adenocarcinomas," Genes Chromosomes Cancer 49(8):688-698.
Written Opinion of the International Searching Authority mailed on Dec. 6, 2011, for PCT Patent Application No. PCT/EP2011/064476 filed on Aug. 23, 2011, four pages. (149.40).
Written Opinion of the International Searching Authority mailed on Dec. 6, 2011, for PCT Patent Application No. PCT/EP2011/064468 filed on Aug. 23, 2011, four pages. (150.40).
Wu et al., "Simultaneous Targeting of Multiple Disease Mediators by a Dual Variable-Domain Immunoglobulin" Nature Biotechnology 25(11): 1290-1297 (Nov. 2007).

(56) References Cited

OTHER PUBLICATIONS

Xie, Z., et al., A New Format of Bispecific Antibody: Highly Efficient Heterodimerization, Expression and Tumor Cell Lysis, J. of Immunol. Methods, 296 (2005) 95-101.
Zeidler et al., "Simultaneous activation of T cells and accessory cells by a new class of intact bispecific antibody results in efficient tumor cell killing," *Journal of Immunology* 163:1246-1252, 1999.
Zuo et al. "An efficient route to the production of an IgG-like bispecific antibody," Protein Engineering 13(5):361-367 (2000).
Chilean Office Action dated Jan. 11, 2012, for Chilean Application No. 3781-2008, 19 pages.
Chilean Office Action dated Aug. 1, 2012, for Chilean Application No. 2008003779, 22 pages.
Chinese Office Action dated Mar. 28, 2012, for Chinese Application No. 20088010258.8, 10 pages.
Korean Office Action dated Feb. 24, 2012, for Korean Patent Application No. 20107013773, 6 pages.
Citations from Israeli Office Action, dated Feb. 29, 2012, in Israeli Patent Application No. 205285, 2 pages.
Japanese Office Action dated Aug. 14, 2012, for Japanese Patent Application No. 2010538440, 12 pages.
Japanese Office Action dated Aug. 14, 2012, for Japanese Patent Application No. 2010-538441, 11 pages.
Korean Office Action dated Jan. 31, 2012, for Korean Patent Application No. 2010-7013760, 11 pages.
European Search Report dated Mar. 14, 2006, for European Patent Application No. 07024864.6, 8 pages.
European Search Report dated Aug. 31, 2009, for European Patent Application No. 09005108.7, 6 pages.
International Search Report mailed on Aug. 5, 2010, for PCT Application No. PCT/EP2010/003559, filed on Jun. 14, 2010, 10 pages.
Dall'Acqua, W. et al. (1998). "Contribution of Domain Interface Residues to the Stability of Antibody CH3 Domain Homodimers", *Biochemistry*, 37:9266-9273.
Dimmock, N.J. et al. (2004). "Valency of antibody binding to virions and its determination by surface plasmon resonance", *Rev. Med. Virol.*, 14:123-135.
Gunasekaran et al., "Enhancing antibody Fc heterodimer formation through electrostatic steering effects: Applications to bispecific molecules and monovalent IgG," *The Journal of Biological Chemistry* 285(25):19637-19646, (Jun. 18, 2010).
Huston, J.S. et al. (1993). "Medical Applications of Single-Chain Antibodies," *Intern. Rev. Immunol.* 10(2-3):195-217.
McLean, G.R. et al. (2005). "A point mutation in the CH3 domain of human IgG3 inhibits antibody secretion without affecting antigen specificity", *Molecular Immunology*, 42:1111-1119.
Mirny, L. et al. (2001). "Protein Folding Theory: From Lattice to All-Atom Models", *Annu. Rev. Biophys. Biomol. Struct.*, 30-361-96.
Novotný, J. et al. (1985). "Structural invariants of antigen binding: Comparison of immunoglobulin $V_L$-$V_H$ and $V_L$-$V_L$ domain dimmers", *Proc. Natl. Acad. Sci. USA*, 82:4592-4596.
Roitt A. et al., (2000), "Multispecific Antibodies Comprising Full Length Antibodies and Single Chain Fab Fragments," *Immunology*, English Translation, Moscow:Mir, pp. 388-389.
Torres, M. et al. (2005). "Variable-Region-Identical Antibodies Differing in Isotype Demonstrate Differences in Fine Specificity and Idiotype", *The Journal of Immunology*, 174:2132.
U.S. Appl. No. 14/551,957, filed Nov. 24, 1014 for Castoldi et al.
Budtschanow et al. "System of Humoral Immunity Antibodies (Theme 2)," Guidance Manual for General Immunology, Twer (2008) p. 3, English Translation, 3 pages.
Arié et al. (2001). "Chaperone Function of FkpA, a Heat Shock Prolyl Isomerase, in the Periplasm of *Escherichia coli*," *Mol. Microbiol.* 39(1):199-210.
Arndt, K.M. et al. (Sep. 7, 2001). "Helix-stabilized Fv (hsFv) antibody fragments: substituting the constant domains of a Fab fragment for a heterodimeric coiled-coil domain," *J. Mol. Biology* 312(1):221-228.

Arndt et al. (1998) "Factors influencing the dimer to monomer transition of an antibody single-chain Fv fragment," Biochemistry, 15;37(37):12918-26.
Bachman. (1987). "Derivations and Genotypes of Some Mutant Derivatives of *Esherichia coli* K-12," Chapter 72 in *Escherichia Coli and Samonella Typimurium* Cellular and Molecular Biology, vol. 2, American Society for Microbiology, Washington D.C., pp. 1190-1219.
Baldwin et al. (1986). "Monoclonal Antibodies in Cancer Treatment," *Lancet* 60:603-606.
Barnes et al. (Mar. 1, 1980). "Methods for Growth of Cultured Cells in Serum-free Medium," *Anal. Biochem.* 102:255-270.
Bass et al. (1990). "Hormone Phage: An Enrichment Method for Variant Proteins With Altered Binding Properties," *Proteins* 8:309-314.
Bird et al. (Oct. 21, 1988). "Single-Chain Antigen-Binding Proteins," *Science* 242(4877):423-6.
Bird et al. (Apr. 28, 1989). "Single-Chain Antigen-Binding Proteins," *Science* 244(4903):409, Erratum.
Booy et al. (Mar.-Apr. 2006, e-pub. Mar. 24, 2006). "Monoclonal and Bispecific Antibodies as Novel Therapeutics," *Arch. Immunol. Ther. Exp.* 54:85-101.
Bothmann et al. (Jun. 2, 2000). "The Periplasmic *Escherichia coli* Peptidylprolyl cis,trans-Isomerase FkpA. I. Increased Functional Expression of Antibody Fragments With and Without cis-Prolines," *J. Biol. Chem.* 275(22):17100-17105.
Burton. (1985). "Immunoglobulin G: Functional Sites," *Molec. Immunol.* 22(3):161-206.
Cao et al. (2003). "Bispecific Antibody Conjugates in Therapeutics," *Advanced Drug Delivery Reviews* 55:171-197.
Capel et al. (1994). "Heterogenity of Human IgG Fc Receptors," *Immunomethods* 4:25-34.
Carlsson et al. (Sep. 1, 1978). "Protein Thiolation and Reversible Protein-Protein Conjugation. N-Succinimidyl 3-(2-pyridyldithio)Propionate, a New Heterobifunctional Reagent," *Biochem. J.* 173:723-737.
Chari et al. (Jan. 1, 1992). "Immunoconjugates Containing Novel Maytansinoids: Promising Anticancer Drugs," *Cancer Research* 52:127-131.
Chen et al. (Nov. 5, 1999). "Selection and Analysis of an Optimized Anti-VEGF Antibody: Crystal Structure of an Affinity-Matured Fab in Complex With Antigen," *J. Mol. Biol.* 293(4):865-681.
Chen et al. (Jul. 9, 1999). "Chaperone Activity of DsbC," *J. Biol. Chem* 274(28):19601-19605.
Chothia et al. (1987). "Canonical Structures for the Hypervariable Regions of Immunoglobulins," *J. Mol. Biol.* 196:901-917.
Chow et al. (Jun. 30, 2000). "Studies on the Subsite Specificity of Rat Nardilysin (N-Arginine Dibasic Convertase)," *J. Biol. Chem.* 275(26):19545-19551.
Clynes et al. (Jan. 1998)."Fc Receptors are Required in Passive and Active Immunity to Melanoma," *Proc. Natl. Acad. Sci. USA* 95:652-656.
Daëron. (1997). "Fc Receptor Biology," *Annu. Rev. Immunol.* 15:203-234.
Davies et al. (1994). "'Camelising' Human Antibody Fragments: NMR Studies on VH Domains," *Febs Letter* 339:285-290.
Davis et al. "SEEDbodies: Fusion Proteins Based on Strand-Exchange Engineered Domain (SEED) $C_H3$ Heterodimers in an Fc Analogue Platform for Asymmetric Binders or Immunofusions and Bispecific Antibodies," *Protein Engineering Design & Selection* 23(4):195-202, (2010, e-pub. Feb. 4, 2010).
De Haas et al. (Oct. 1995). "Fcγ Receptors of Phagocytes," *J. Lab. Clin. Med.* 126(4):330-341.
Deyev et al. (2009). "Modern Technologies for Creating synthetic Antibodies for Clinical Application," *Acta Naturae* 1:32-50.
Dooley et al. (2006). "Antibody Repertoire Development in Cartilaginous Fish," *Dev. Comp. Immunol.* 30 (1-2):43-56.
Doronina et al. (Jul. 2, 2003, e-pub. Jun. 1, 2003). "Development of Potent Monoclonal Antibody Auristatin Conjugates for Cancer Therapy," *Nat. Biotechnol.* 21(7):778-784.
Eaton et al. (Dec. 30, 1986). "Construction and Characterization of an Active Factor VIII Variant Lacking the Central One-Third of the Molecule," *Biochemistry* 25(26):8343-8347.

(56) References Cited

OTHER PUBLICATIONS

Els Conrath et al. (Mar. 9, 2001). "Camel Single-Domain Antibodies as Modular Building Units in Bispecific and Bivalent Antibody Constructs," *Journal of Biological Chemistry* 276(19):7346-7350.

Fraker et al. (Feb. 28, 1978). "Protein and Cell Membrane Iodinations With a Sparingly Soluble Chloroamide, 1,3,4,6-Tetrachloro-3a,6a-Diphenylglycoluril," *Biochem. Biophys. Res. Commun.* 80(4):49-57.

Gadgil et al. (2006). "Identification of cysteinylation of a free cysteine in the Fab region of a recombinant monoclonal IgG1 antibody using lys-C limited proteolysis coupled with LC/MS analysis," *Analytical biochem*. 2006: 355:185-174.

Gazzano-Santoro et al. (1996). "A Non-Radiative Complement-Dependent Cytotoxicity Assay for Anti-CD20 Monoclonal Antibody," *J. Immunol. Methods* 202:163.

Geoghegan et al. (1992). "Site-Directed Conjugation of Nonpeptide Groups to Peptides and Proteins via Periodate Oxidation of a 2-Amino Alcohol. Application Modification at N Terminator Serine," *Bioconjugate Chem*. 3(2):138-146.

Graham et al. (1977). "Characteristics of a Human Cell Line Transformed by DNA From Human Adenovirus Type 5," *J. Gen Virol.* 36:59-72.

Greenwood et al. "Structural Motifs Involved in Human IgG Antibody Effector Functions,". *Eur. J. Immunology* 23(5):1098-1104, (May 1993).

Grönwall C. et al. (Jun. 2008). "Generation of Affibody ligands binding interleukin-2 receptor alpha/CD25," *Biotechnol. Appl. Biochem.* 50(Pt. 2):97-112.

Guss et al. (1986). "Structure of the IgG-Binding Regions of Streptococcal Protein G," *EMBO J.* 5(7):1567-1575.

Guyer et al. (Aug. 1976). "Immunoglobulin Binding by Mouse Intestinal Epithelial Cell Receptors," *J. Immunol*. 117(2):587-593.

Ham et al. (1979). "Media and Growth Requirements," *Meth. Enz.* 58:44-93.

Hamers-Casterman et al. (1993). "Naturally occurring antibodies devoid of light chains," *Nature* 363:446-448.

Hara et al. (1996). "Overproduction of Penicillin-Binding Protein 7 Suppresses Thermosensitive Growth Defect at Low Osmolarity Due to an spr Mutation of *Escherichia coli*," *Microbial Drug Resistance* 2:63-72.

Hinman et al. (Jul. 15, 1993). "Preparation and Characterization of Monoclonal Antibody Conjugates of the Calicheamicins: A Novel and Potent Family of Antitumor Antibiotics," *Cancer Res*. 53:3336-3342.

Holliger et al. (Jul. 1993). "Diabodies': Small Bivalent and Bispecific Antibody Fragments," *Proc. Natl. Acad. Sci. USA* 90-6444-6448.

Holt et al. (Nov. 2003). "Domain Antibodies: Proteins for Therapy," *Trends Biotechnol*. 21(11):484-490.

Huston et al. (Aug. 1988). "Protein Engineering Of Antibody Binding Sites: Recovery Of Specific Activity in an Anti-Digoxin Single-Chain Fv Analogue Produced In *Escherichia coli*," *Proc. Natl. Acad. Sci. U.S.A.* 85(16):5879-5883.

Janeway. (Oct. 12, 1989). "Immunotherapy by Peptdes?," *Nature* 341:482-483.

Johnson et al. (1991). "Construction of Single-Chain Fv Derivatives Monoclonal Antibodies and Their Production in *Escherichia coli*," *Methods Enzymol*. 203:88-98.

Johnson et al. (2003). Methods in Molecular Biology 248:11-25. (Lo, ed., Human Press, Totowa, NJ).

Joly et al. (Mar. 1998). "Overexpression of *Escherichia coli* Oxidoreductases Increases Recombinant Insulin-like Growth Factor-I Accumulation," *Proc. Natl. Acad. Sci. USA* 95-2773-2777.

Jones et al. (May 29, 1986). "Replacing the Complementarity-Determining Regions in a Human Antibody With Those From a Mouse," *Nature* 321:522-525.

Kim et al. (1994). "Localization of the Site of the Murine IgG1 Molecule that is Involved in Binding to the Murine Intestinal Fc Receptor," *Eur J Immunol*. 24:2429-2434.

Krugmann et al. (1997). "Structural Requirements for Assembly of Dimeric IgA Probed by Site-Directed Mutagenesis of J Chain and a Cysteine Residue of the α-Chain CH2 Domain," *The Journal of Immunology* 159:244-249.

Kumar et al. (Nov. 10, 2000). "Molecular Cloning and Expression of the Fabs of Human Autoantibodies in *Escherichia coli*,"*J. Biol. Chem*. 275(45):35129-35136.

Lee et al. (1999). "Generation And Characterization of A Novel Single-Gene-Encoded Single-Chain Immunoglobulin Molecule With Antigen Binding Activity and Effector Functions" *Mol Immunol.* 36(1):61-71.

Lindmark et al. (1983). "Binding of Immunoglobulins to Protein A and Immunoglobulin Levels in Mammalian Sera," *J. Immunol. Meth*. 62:1-13.

Liu et al. (Aug. 6, 1996) "Eradication of Large Colon Tumor Xenografts by Targeted Delivery of Maytansinoids," *Proc. Natl. Acad. Sci. USA* 93:8618-8623.

Lode et al. (Jul. 15, 1998). "Targeted Therapy With a Novel Enediyene Antibiotic Calicheamicin $\theta^I$ Effectively Suppresses Growth and Dissemination of Liver Metastases in a Syngeneic Model of Murine Neuroblastoma," *Cancer Res.* 58:2925-2928.

Lu et al. (2002). "Fab-scFv Fusion Protein: an Efficient Approach to Production of Bispecific Antibody Fragments" *J. Immunol Methods* 267(2):213-26.

Lu et al. (Jan. 23, 2004). "Simultaneous Blockage of Both the Epidermal Growth Factor Receptor and the Insulin-Like Growth Factor Receptor Signaling Pathways in Cancer Cells With a Fully Human Recombinant Bispecific Antibody" *J. Biol. Chem.* 279(4):2856-2865.

Lu et al. (2004. E-pub. Apr. 22, 2004). "The Effect Of Variable Domain Orientation And Arrangement on the Antigen-Binding Activity of a Recombinant Human Bispecific Diabody" *Biochem. Biophys. Res. Commun*. 318(2):507-513.

MacCallum et al. (1996)."Antibody-antigen Interactions: Contact Analysis and Binding Site Topography," *J. Mol. Biol.* 262:732-745.

Malmborg et al. (1995). "BIAcore as a Tool in Antibody Engineering," *J. Immunol. Methods* 183:7-13.

Mandler et al (Oct. 4, 2000). "Immunoconjugates of Geldanamycin and Anti-HER2 Monoclonal Antibodies: Antiproliferative Activity on Human Breast Carcinoma Cell Lines," *J. of the Nat. Cancer Inst*. 92(19):1573-1581.

Mandler et al. (May 15, 2000). "Synthesis and Evaluation of Antiproliferative Activity of a Geldanamycin-Herceptin Immunoconjugate," *Biorganic & Med. Chem. Letters* 10:1025-1028.

Mandler et al. (Jul.-Aug. 2002, e-pub. Jun. 19, 2002). "Modifications in Synthesis Strategy Improve the Yield and Efficacy of Geldanamycin-herceptin Immunoconjugates,"*Bioconjugate Chem.* 13(4):786-791.

Marvin et al. (2006). "Bispecific antibodies for dual-modality cancer therapy: killing two signaling cascades with one stone," *Current Opin. Drug Discovery & Dev*. 9(2):184-193.

Mason et al. (2004). "Coiled Coil Domains: Stability, Specificity, and Biological Implications," *ChemBioChem* 5:170-176.

Mather (1980). "Establishment and Characterization of Two Distinct Mouse Testicular Epithelial Cell Lines," *Biol. Reprod*. 23:243-251.

Mather et al. (1982). "Culture of Testicular Cells in Hormone-supplemented Serum-Free Medium," *Annals N.Y. Aca. Sci*. 383:44-68.

Muller et al (Dec. 15, 2000). "Processing and Sorting of the Prohormone Convertase 2 Propeptide," *J. Biol. Chem*. 275(50):39213-39222.

Murakami et al. (1995). "Cell Cycle Regulation, Oncogenes, and Antineoplastic Drugs" Chapter 1 in The Molecular Basis of Cancer, Mendelsohn and Israel, Philadelphia, W.B. Saunders, Philadelphia pp. 3-17.

Muyldermas et al. (Apr. 2001). "Recognition of Antigens by Single-domain Antibody Fragments: the Superfluous Luxury of Paired Domains," *Trend Biochem. Sci*. 26(4):230-235.

Natsume et al. (Sep. 1, 2006). "Fucose Removal From Complex-type Oligosaccharide Enhances the Antibody-dependent Cellular Cytotoxicity of Single-gene-encoded Bispecific Antibody Comprising of Two Single-Chain Antibodies Linked to the Antibody Constant Region," *Journal of Biochemistry* 140(3):359-368.

(56) References Cited

OTHER PUBLICATIONS

Nicolaou et al. (1994). Calicheamicin $\theta I_1$: A Rationally Designed Molecule with Extremely Potent and Selective DNA Cleaving Properties and Apoptosis Inducing Activity, *Agnew Chem. Intl. Ed. Engl.* 33(2):183-186.
Niculescu-Duvaz et al. (1997). "Antibody-Directed Enzyme Prodrug Therapy (ADEPT): A Review," *Adv. Drg. Del. Rev.* 26:151-172.
Nieri et al. (Feb. 1, 2009). "Antibodies for Therapeutic Uses and the Evolution of Biotechniques," *Current Med. Chem.* 16(6):753-779.
Nilsson et al. (1987). "A synthetic IgG-binding domain based on staphylococcal protein A," *Prot. Eng.* 1:107-133.
Nord et al. (1995). "A combinatorial library of an α-helical bacterial receptor domain," *Prot. Eng.* 8:601-608.
Nord et al. (1997). "Binding proteins selected from combinatorial libraries of an α-helical bacterial receptor domain," *Nat. Biotech.* 15:772-777.
Offner et al. (Jan. 25, 1991). "T Cell Receptor Peptide Therapy Triggers Autoregulation of Experimental Encephalomyelitis," *Science* 251:430-432.
O'Shea et al. "Peptide 'Velcro': design of a heterodimeric coiled coil," *Current Biology* 3(10):658-667, (1993).
Pan et al. (Jan. 2007). "Blocking Neuropilin-1 Function Has an Additive Effect with nti-VEGF to Ihibit Tumor Growth," *Cancer Cell* 11:53-67.
Pettit et al. (Jul.-Aug. 1981). "Marine Animal Biosynthetic Constituents for Cancer Chemotherapy," *J. Nat. Prod.* 44:482-485.
Pettit et al. (1997). "The Dolastatins," *Fortschr. Chem. Org. Naturst.* 70:1-79.
Pettit et al. (1998). "Antineoplastic Agents 360. Synthesis and Cancer Cell Growth Inhibitory Studies of Dolastatin 15 Structural Modifications," *Anti-Cancer Drug Design* 13:47-66.
Pettit. et. al. (Nov. 1998). "Specific Activities of Dolastatin 10 and Peptide Derivatives Against *Cryptococcus neoformans*," *Antimirob. Agents Chemother.* 42(11):2961-2965.
Pleass et al. (Aug. 13, 1999). "Identification of Residues in the CH2/CH3 Domain Interface of IgA Essential for Interaction With the Human fcα Receptor (Fcα R) CD89," The Journal of Biology Chemistry 274(33):23508-23514.
Pluckthun. (1994). "Antibodies from *Escherichia coli*" Chapter 11 in The Pharmacology of Monoclonal Antibodies: Handbook of Phannacology, Rosenberg and Moore, eds., Berlin:Springer-Verlag, vol. 113, pp. 269-315.
Pluckthun, A. et al. (Jun. 1, 1997). "New protein engineering approaches to multivalent and bispecific antibody fragments," *Immunotechnology* 3(2):83-105.
Poncet (1999). "The Dolastatins, A Family of Promising Antineoplastic Agents," *Curr. Pharm. Des.* 5:139-162.
Presta (1992). "Antibody Engineering," *Curr. Op. Struct. Biol.* 2:593-596.
Presta et al. (Sep. 1, 1993). "Humanization of an Antibody Directed Against IgE," *J. Immunol.* 151(5):2623-2632.
Proba et al. (Jul. 4, 1995). "Functional Antibody Single-Chain Fragments From The Cytoplasm of *Escherichia coli*: Influence Of Thioredoxin Reductase (TrxB)," *Gene* 159:203-207.
Ramm et al. (Jun. 2, 2001). "The Peroplasmic *Escherichia coli* Peptidylproly cis,trans-Isomerase FkpA," *J. Biol. Chem.* 275(22):17106-17113.
Ravetch et al. (1991). "Fc Receptors," *Annu. Rev. Immunol.* 9:457-492.
Reiter et al. (1994). "Stabilization of the Fv Fragments in Recombinant Immunotoxins by Disulfide Bonds Engineered into Conserved Framework Regions," *Biochemistry* 33(18):5451-5449.
Reiter et al. (Jul. 15, 1994). "Improved Binding And Antitumor Activity Of A Recombinant Anti-erbB2 Immunotoxin by Disulfide Stabilization of the Fv Fragment," *J. Biol. Chem.* 269(28):18327-18331.
Reiter et al. (May 1994). "Engineering Interchain Disulfide Bonds Into Conserved Framework Regions Of Fv Fragments: Improved Biochemical Characteristics Of Recombinant Immunotoxins Containing Disulfide-Stabilized Fv," *Protein Eng.* 7(5):697-704.
Rowland et al (1986). "Drug Localisation and Growth Inhibition Studies of Vindesine-Monoclonal Anti-CEA Conjugates in a Human Tumour Xenograft," *Cancer Immunol. Immunother.* 21:183-187.
Ruppert et al. (Mar. 11, 1993). "Cloning and Expression of Human $TAF_{II}250$: a TBP-Associated Factor Implicated in Cell-Cycle Regulation," *Nature* 362:175-179.
Santos et al. (Oct. 1999) "Generation and Characterization of a Single Gene-Encoded Single-Chain-tetravalent Antitumor Antibody" *Clinical Cancer Research* 5(10 Suppl):3118s-3123s.
Schirrmann et al. (Jan./Feb. 2010). "Oligomeric Forms of Single Chain Immunoglobulin (sclgG)," *Landes Bioscience* 2(1):73-76.
Schoonjans et al. (2000). "Efficient Heterodimerization of Recombinant Bi- and Trispecific Antibodies" *Bioseparation* 9(3):179-183.
Schröder et al. (1965). "III. Formation of the Peptide Bond," The Peptides, vol. 1, Academic Press, New York, New York, pp. 76-136.
Shechter et al. (1976) "Selective Chemical Cleavage of Tryptophanyl Peptide Bonds by Oxidative Chlorination With N-Chlorosuccinimide," *Biochemistry* 15(23):5071-5075.
Sheriff et al. (1996). "Redefining the minimal antigen-binding fragment," *Nature Struct. Biol.* 3:733-736.
Siebenlist et al. (Jun. 1980). "*E. coli* RNA Polymerase Interacts Homologously with Two Different Promoters," *Cell* 20:269-281.
Sims et al. (Aug. 15, 1993). "A Humanized CD18 Antibody Can Block Function Without Cell Destruction," *J. Immunol.* 151(4):2296-2308.
Smith-Gill et al. (Dec. 15, 1987). "Contributions of Immunoglobulin Heavy and Light Chain to Antibody Specificity for Lysozyme and Two Haptens," *J. Immunol.* 139(12):4135-4144.
Song et al. (2000). "Light Chain of Natural Anibody Plays a Dominant Role in Protein Antigen Binding," Biochem. Biophys. Res. Comm. 268(2):390-394.
Steiner. (1991). "The Biosynthesis of Biologically Active Peptides: A Perspective," Chapter 1 in Peptide Biosynthesis and Processing, Fricker ed., CRC Press, Boca Raton, FL, pp. 1-16.
Stella et al. (1985). "Prodrugs: A Chemical Approach to Target Drug Delivery" Directed Drug Delivery, Borchardt et al (ed.), Human Press, pp. 247-267.
Stites et al. (1994). "Immunoglobulin Protiens," Chapter 6 in Basic Clinical Immunology, $8^{th}$ Edition, Appleton & Lange, Norwalk, CT, p. 71.
Stork et al. (Nov. 2007, e-pub. Nov. 3, 2007 ). "A Novel Tri-Functional Antibody Fusion Protein With Improved Pharmacokinetic Properties Generated By Fusing A Bispecific Single-Chain Diabody With An Albumin-Binding Domain From Streptococcal Protein G," *Protein Eng. Des. Sel.* 20(11):569-576.
Syrigos et al. (1999). "Antibody Directed Enzyme Prodrug Therapy (ADEPT): A Review of the Experimental and Clinical Considerations," *Anticancer Research* 19:605-614.
Tao et al. (Apr. 1991). "The Differential Ability of Human IgG1 and IgG4 to Activate Complement is Determined by the COOH-terminal Sequence of the CH2 Domain," J. Exp. Med 173:1025-1028.
Thie et al. (Jul. 22, 2009). "Multimerization Domains for Antibody Phage Display and Antibody Production," *New Biotech.* 26(6):314-321.
Thorpe. (1985) "Antibody Carriers of Cyotoxic Agents in Cancer Therapy: A Review," in A Monoclonal Antibodies 84: Biological and Clinical Applications, A. Pinchera et al (eds) pp. 475-506.
Urlaub et al. (Jul. 1980). "Isolation of Chinese Hamster Cell Mutants Deficient in Dihydrofolate Reductase Activity," *Proc. Natl. Acad Sci USA* 77(7):4216-4220.
Verhoeyen et al. (Mar. 25, 1988). "Reshaping Human Antibodies: Grafting an Antilysozyme Activity," *Science* 239:1534-1536.
Vitetta et al. (Nov. 20, 1987). "Redesigning Nature's Poisons to Create Anti-tumor Reagents," Science 238:1098-1104.
Walker et al. (Jun. 5, 2009, e-pub. Apr. 16, 2009). "Efficient Recovery of High-Affinity Antibodies From a Single-Chain Fab Yeast Display Library," *J. Mol. Biol.* 389(2):365-375.
Ward et al. (Oct. 12, 1989). "Binding Activities of a Repertoire of Single Immunoglobulin Variable Domains Secreted From *Escherichia coli*," *Nature* 341:544-546.
Wilman. (1986). "Prodrugs in Cancer Chemotherapy," *Biochemical Society Transactions* 14:37-382, $615^{th}$ Meeting Belfast, 8 pages.

(56) References Cited

OTHER PUBLICATIONS

Woyke et al. (Dec. 2001). "In Vitro Activities and Postantifungal Effects of the Potent Dolastatin10 Derivative Auristatin PHE," *Antimicrob. Agents and Chemother.* 45(12):3580-3584.

Wrank et al. (Dec. 21, 2012). "Luz-Y: A Novel Platform for the Mammalian Cell Production of Full-length IgG Bispeciic Antibodies," *Journal of Biological Chemistry* 287(52):43331-43339.

Xu et al. (2000). "Diversity in the CDR3 region of V(H) is sufficient for most antibody specificities," *Immunity* 13:37-45.

Yaniv. (May 6,1982). "Enhancing Elements for Activation of Eukaryotic Promoters," *Nature* 297:17-18.

Zapata et al. (1995). "Engineering Linear F(ab$^1$)$_2$ Fragments for Efficient Production in *Escherichia coli* and Enhanced Antiproliferative Activity," *Protein Eng.* 8(10):1057-1062.

Zhu et al. (1997). "Remodeling Domain Interfaces to Enhance Heterodimer Formation," *Protein Science* 6:781-788.

International Search Report mailed on Aug. 6, 2013, for PCT Application No. PCT/US2013/025365, filed Feb. 8, 2013, 6 pages.

Written Opinion mailed on Aug. 6, 2013, for PCT Application No. PCT/US2013/025365, filed Feb. 8, 2013, 9 pages.

Extended European Search Report mailed on Aug. 5, 2013, for European Patent Application No. 10817575.3, eleven pages.

International Preliminary Report on Patentability for PCT/EP2011/054505, mailed on Oct. 2, 2012, filed on Mar. 24, 2011, 8 pages.

International Preliminary Report on Patentability mailed on Aug. 21, 2014, for PCT Patent Application No. PCT/US2013/025365, filed on Feb. 8, 2013, 11 pages.

International Search Report mailed on Jun. 15, 2011 for PCT Patent Application No. PCT/US2010/002546 filed on Sep. 16, 2010, five pages.

International Search Report for PCT/EP2011/054505 mailed on Jun. 28, 2011, filed on Mar. 24, 2011, 7 pages.

Written Opinion of the International Searching Authority mailed on Jun. 15, 2011 for PCT Patent Application No. PCT/US2010/002546 filed on Sep. 16, 2010, seven pages.

Barbin et al. (Mar.-Apr. 2006). "Influence of Variable N-Glycosylation on the Cytolytic Potential of Chimeric CD19 Antibodies," *J. Immunother.* 29(2):122-133.

Ausubel et al., Short Protocols in Molecular Biology, Greene Publishing and Wiley Interscience, New York, New York, (Table of Contents), (1987).

U.S. Appl. No. 14/735,024, filed Jun. 9, 2015 for Christensen et al.

\* cited by examiner

Fig. 1
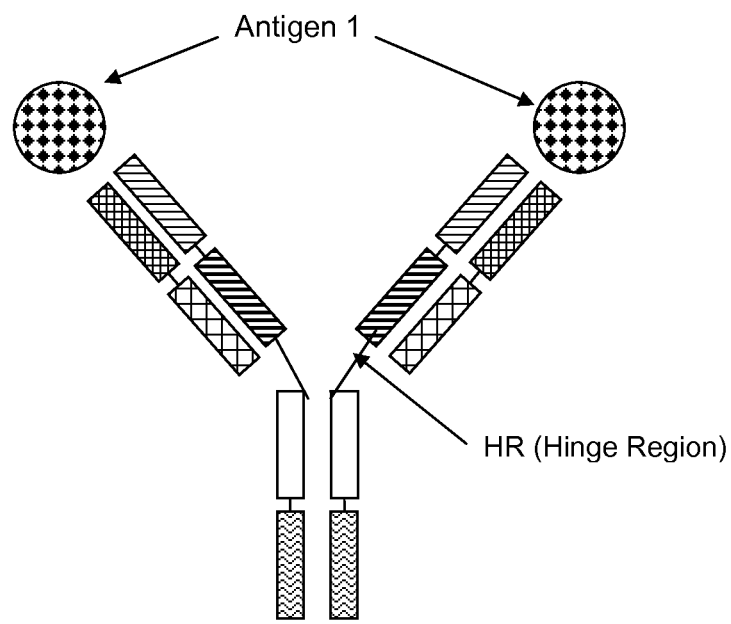
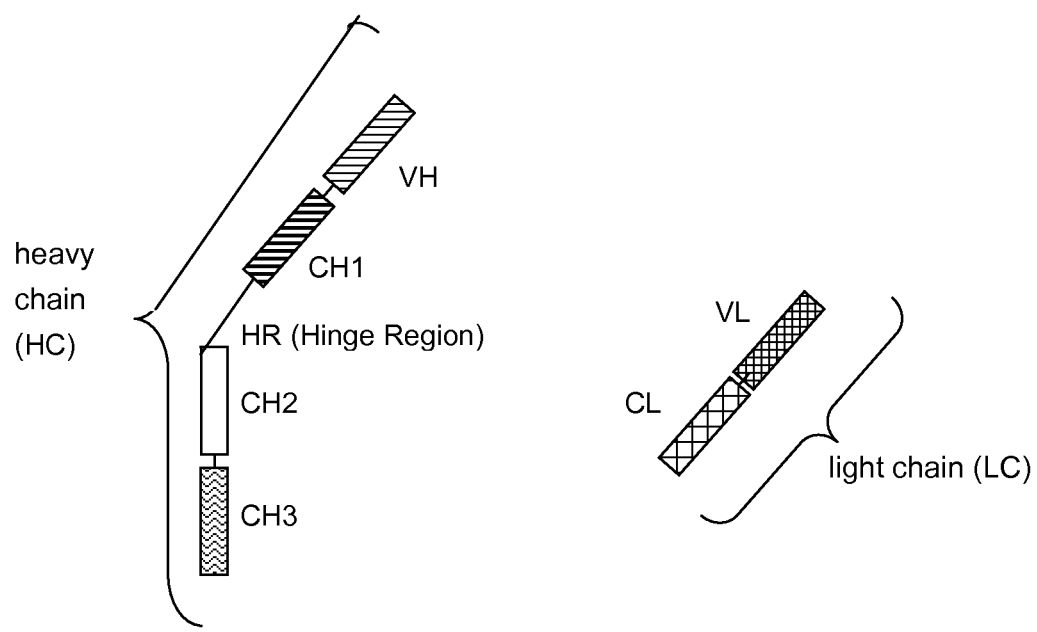

Fig. 7
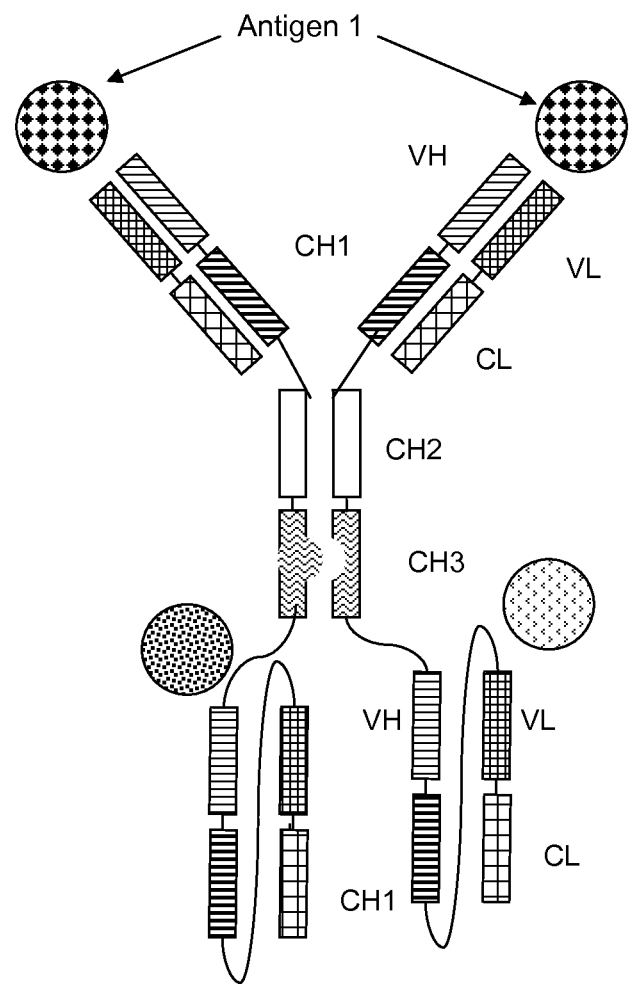
Antigen 1 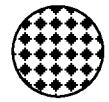  Antigen 2 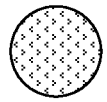  Antigen 3 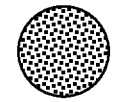

MULTISPECIFIC ANTIBODIES COMPRISING FULL LENGTH ANTIBODIES AND SINGLE CHAIN FAB FRAGMENTS

PRIORITY TO RELATED APPLICATION(S)

This application claims the benefit of European Patent Application No. 09004909.9, filed Apr. 2, 2009, which is hereby incorporated by reference in its entirety.

The present invention relates to multispecific, especially bispecific antibodies comprising full length antibodies and single chain Fab fragments, methods for their production, pharmaceutical compositions containing the antibodies, and uses thereof.

SEQUENCE LISTING

The instant application contains a Sequence Listing which has been submitted via EFS-Web and is hereby incorporated by reference in its entirety. Said ASCII copy, created on Mar. 18, 2010, is named 26056.txt, and is 19,695 bytes in size.

BACKGROUND OF THE INVENTION

A wide variety of multispecific recombinant antibody formats have been developed in the recent past, e.g. tetravalent bispecific antibodies by fusion of, e.g., an IgG antibody format and single chain domains (see e.g. Coloma, M. J., et al., Nature Biotech 15 (1997) 159-163; WO 2001/077342; and Morrison, S. L., Nature Biotech 25 (2007) 1233-1234).

Also several other new formats wherein the antibody core structure (IgA, IgD, IgE, IgG or IgM) is no longer retained such as dia-, tria- or tetrabodies, minibodies, several single chain formats (scFv, Bis-scFv), which are capable of binding two or more antigens, have been developed (Holliger, P., et al., Nature Biotech 23 (2005) 1126-1136; Fischer, N., Léger, O., Pathobiology 74 (2007) 3-14; Shen, J., et al., Journal of Immunological Methods 318 (2007) 65-74; Wu, C., et al., Nature Biotech. 25 (2007) 1290-1297).

All such formats use linkers either to fuse the antibody core (IgA, IgD, IgE, IgG or IgM) to a further binding protein (e.g. scFv) or to fuse e.g. two Fab fragments or scFvs (Fischer, N., Léger, O., Pathobiology 74 (2007) 3-14). It has to be kept in mind that one may want to retain effector functions, such as e.g. complement-dependent cytotoxicity (CDC) or antibody dependent cellular cytotoxicity (ADCC), which are mediated through the Fc receptor binding, by maintaining a high degree of similarity to naturally occurring antibodies.

In WO 2007/024715 are reported dual variable domain immunoglobulins as engineered multivalent and multispecific binding proteins. A process for the preparation of biologically active antibody dimers is reported in U.S. Pat. No. 6,897,044. Multivalent $F_v$ antibody construct having at least four variable domains which are linked with each over via peptide linkers are reported in U.S. Pat. No. 7,129,330. Dimeric and multimeric antigen binding structures are reported in US 2005/0079170. Tri- or tetra-valent monospecific antigen-binding protein comprising three or four Fab fragments bound to each other covalently by a connecting structure, which protein is not a natural immunoglobulin are reported in U.S. Pat. No. 6,511,663. In WO 2006/020258 tetravalent bispecific antibodies are reported that can be efficiently expressed in prokaryotic and eukaryotic cells, and are useful in therapeutic and diagnostic methods. A method of separating or preferentially synthesizing dimers which are linked via at least one interchain disulfide linkage from dimers which are not linked via at least one interchain disulfide linkage from a mixture comprising the two types of polypeptide dimers is reported in US 2005/0163782. Bispecific tetravalent receptors are reported in U.S. Pat. No. 5,959,083. Engineered antibodies with three or more functional antigen binding sites are reported in WO 2001/077342.

Multispecific and multivalent antigen-binding polypeptides are reported in WO 1997/001580. WO 1992/004053 reports homoconjugates, typically prepared from monoclonal antibodies of the IgG class which bind to the same antigenic determinant are covalently linked by synthetic cross-linking Oligomeric monoclonal antibodies with high avidity for antigen are reported in WO 1991/06305 whereby the oligomers, typically of the IgG class, are secreted having two or more immunoglobulin monomers associated together to form tetravalent or hexavalent IgG molecules. Sheep-derived antibodies and engineered antibody constructs are reported in U.S. Pat. No. 6,350,860, which can be used to treat diseases wherein interferon gamma activity is pathogenic. In US 2005/0100543 are reported targetable constructs that are multivalent carriers of bi-specific antibodies, i.e., each molecule of a targetable construct can serve as a carrier of two or more bi-specific antibodies. Genetically engineered bispecific tetravalent antibodies are reported in WO 1995/009917. In WO 2007/109254 stabilized binding molecules that consist of or comprise a stabilized scFv are reported.

Müller, D., et al., Handbook of Therapeutic antibodies, Part III, Chapter 2, (2008) 345-378 refers to bispecific antibodies, e.g. to a full length antibody to which two scFv fragments are fused via a peptide linker at the C-terminus of the heavy chain (see also WO 1995/009917). Hust, M., et al., BMC Biotechnology (2007) 7 refers to single chain Fab (sc-Fab) fragments.

However in view of different problems and aspects of multispecific antibodies (like e.g. pharmacokinetic and biological properties, stability, aggregation, expression yield) there is a need of further alternative multispecific antibody formats. Especially genetically engineered bispecific tetravalent antibodies reported in WO 1995/009917 and Müller D., et al., Handbook of Therapeutic antibodies, Part III, Chapter 2, (2008) 345-378 showed only very low expression yields.

SUMMARY OF THE INVENTION

A first aspect of the current invention is a multispecific antibody comprising
a) a full length antibody consisting of two antibody heavy chains and two antibody light chains wherein the antibody specifically binds to a first antigen; and
b) one or more single chain Fab fragments that specifically bind to one or more antigens different from the first antigen, wherein each of the one or more single chain Fab fragments is fused to the full length antibody via a peptide connector at the C- or N-terminus of the heavy or light chain of the full length antibody.

A preferred aspect of the current invention is a multispecific antibody as described above comprising one to four single chain Fab fragments that specifically bind to one to four antigens different from the first antigen, wherein each of the one to four single chain Fab fragments is fused to the full length antibody via a peptide connector at the C- or N-terminus of the heavy or light chain of the full length antibody.

Preferably the multispecific antibody comprises one or two single chain Fab fragments that specifically bind to a second antigen (bispecific antibody).

Preferably the multispecific antibody comprises two single chain Fab fragments that specifically bind to a second antigen (bispecific antibody).

Preferably the multispecific antibody comprises two single chain Fab fragments that specifically bind to a second antigen and a third antigen (trispecific antibody).

A further aspect of the invention is a nucleic acid molecule encoding a chain of the multispecific antibody wherein a single chain Fab fragment is fused to the C- or N-terminus of the heavy or light chain of the full length antibody.

Still further aspects of the invention are a pharmaceutical composition comprising the multispecific antibody.

The multispecific antibodies according to the invention showed valuable properties such as a high stability, low aggregation tendency (see e.g. Example 2 (e.g. compared to a full length antibody to which two scFv fragments are fused via a peptide linker at the C-terminus of the heavy chain (see WO 1995/009917 or Müller, D., et al., Handbook of Therapeutic antibodies, Part III, Chapter 2, (2008) 345-378). The multispecific antibodies according to the invention one the one hand show new properties due to their binding to different antigens, and on the other hand are suitable for production and pharmaceutical formulation due to their good stability, low aggregation and valuable pharmacokinetic and biological properties. Due to their Ig core and ability to be produced in mammalian expression systems they still retain the properties of natural antibodies like ADCC and CDC.

DETAILED DESCRIPTION OF THE INVENTION

A first aspect of the current invention is a multispecific antibody comprising
a) a full length antibody specifically binding to a first antigen and consisting of two antibody heavy chains and two antibody light chains; and
b) one or more single chain Fab fragments specifically binding to one to four further antigens (preferably specifically binding to one further antigen),
wherein the single chain Fab fragments under b) are fused to the full length antibody under a) via a peptide connector at the C- or N-terminus of the heavy or light chain of the full length antibody.

A preferred aspect of the current invention is a multispecific antibody comprising
a) a full length antibody specifically binding to a first antigen and consisting of two antibody heavy chains and two antibody light chains; and
b) one to four single chain Fab fragments specifically binding to one to four further antigens (preferably specifically binding to one further antigen),
wherein the single chain Fab fragments under b) are fused to the full length antibody under a) via a peptide connector at the C- or N-terminus of the heavy or light chain of the full length antibody.

In one embodiment one or two identical single chain Fab fragments binding to a second antigen are fused to the full length antibody via a peptide connector at the C-terminus of the heavy or light chains of the full length antibody.

In one embodiment one or two identical single chain Fab fragments binding to a second antigen are fused to the full length antibody via a peptide connector at the C-terminus of the heavy chains of the full length antibody.

In one embodiment one or two identical single chain Fab fragments binding to a second antigen are fused to the full length antibody via a peptide connector at the C-terminus of the light chains of the full length antibody.

In one embodiment two identical single chain Fab fragments binding to a second antigen are fused to the full length antibody via a peptide connector at the C-terminus of each heavy or light chain of the full length antibody.

In one embodiment two identical single chain Fab fragments binding to a second antigen are fused to the full length antibody via a peptide connector at the C-terminus of each heavy chain of the full length antibody.

In one embodiment two identical single chain Fab fragments binding to a second antigen are fused to the full length antibody via a peptide connector at the C-terminus of each light chain of the full length antibody.

The term "full length antibody" denotes an antibody consisting of two "full length antibody heavy chains" and two "full length antibody light chains" (see FIG. 1). A "full length antibody heavy chain" is a polypeptide consisting in N-terminal to C-terminal direction of an antibody heavy chain variable domain (VH), an antibody constant heavy chain domain 1 (CH1), an antibody hinge region (HR), an antibody heavy chain constant domain 2 (CH2), and an antibody heavy chain constant domain 3 (CH3), abbreviated as VH-CH1-HR-CH2-CH3; and optionally an antibody heavy chain constant domain 4 (CH4) in case of an antibody of the subclass IgE. Preferably the "full length antibody heavy chain" is a polypeptide consisting in N-terminal to C-terminal direction of VH, CH1, HR, CH2 and CH3. A "full length antibody light chain" is a polypeptide consisting in N-terminal to C-terminal direction of an antibody light chain variable domain (VL), and an antibody light chain constant domain (CL), abbreviated as VL-CL. The antibody light chain constant domain (CL) can be δ (kappa) or λ (lambda). The two full length antibody chains are linked together via inter-polypeptide disulfide bonds between the CL domain and the CH1 domain and between the hinge regions of the full length antibody heavy chains. Examples of typical full length antibodies are natural antibodies like IgG (e.g. IgG 1 and IgG2), IgM, IgA, IgD, and IgE. The full length antibodies according to the invention can be from a single species e.g. human, or they can be chimerized or humanized antibodies. The full length antibodies according to the invention comprise two antigen binding sites each formed by a pair of VH and VL, which both specifically bind to the same antigen. The C-terminus of the heavy or light chain of the full length antibody denotes the last amino acid at the C-terminus of the heavy or light chain. The N-terminus of the heavy or light chain of the full length antibody denotes the last amino acid at the N-terminus of the heavy or light chain.

A "single chain Fab fragment" (see FIG. 2) is a polypeptide consisting of an antibody heavy chain variable domain (VH), an antibody constant domain 1 (CH1), an antibody light chain variable domain (VL), an antibody light chain constant domain (CL) and a linker, wherein the antibody domains and the linker have one of the following orders in N-terminal to C-terminal direction:
a) VH-CH1-linker-VL-CL, b) VL-CL-linker-VH-CH1, c) VH-CL-linker-VL-CH1 or d) VL-CH1-linker-VH-CL; and wherein the linker is a polypeptide of at least 30 amino acids, preferably between 32 and 50 amino acids. The single chain Fab fragments a) VH-CH1-linker-VL-CL, b) VL-CL-linker-VH-CH1, c) VH-CL-linker-VL-CH1 and d) VL-CH1-linker-VH-CL, are stabilized via the natural disulfide bond between the CL domain and the CH1 domain. The term "N-terminus denotes the last amino acid of the N-terminus, The term "C-terminus denotes the last amino acid of the C-terminus.

In a preferred embodiment the antibody domains and the linker in the single chain Fab fragment have one of the following orders in N-terminal to C-terminal direction:

a) VH-CH1-linker-VL-CL, or b) VL-CL-linker-VH-CH1, more preferably VL-CL-linker-VH-CH1.

In another preferred embodiment the antibody domains and the linker in the single chain Fab fragment have one of the following orders in N-terminal to C-terminal direction:
a) VH-CL-linker-VL-CH1 or b) VL-CH1-linker-VH-CL.

Optionally in the single chain Fab fragment, additionally to the natural disulfide bond between the CL-domain and the CH1 domain, also the antibody heavy chain variable domain (VH) and the antibody light chain variable domain (VL) are disulfide stabilized by introduction of a disulfide bond between the following positions:
i) heavy chain variable domain position 44 to light chain variable domain position 100,
ii) heavy chain variable domain position 105 to light chain variable domain position 43, or
iii) heavy chain variable domain position 101 to light chain variable domain position 100 (numbering always according to EU index of Kabat).

Such further disulfide stabilization of single chain Fab fragments is achieved by the introduction of a disulfide bond between the variable domains VH and VL of the single chain Fab fragments. Techniques to introduce unnatural disulfide bridges for stabilization for a single chain Fv are described e.g. in WO 94/029350, Rajagopal, V., et al., Prot. Engin. 10 (1997) 1453-59; Kobayashi, H., et al., Nuclear Medicine & Biology, Vol. 25 (1998) 387-393; or Schmidt, M., et al., Oncogene 18 (1999) 1711-1721. In one embodiment the optional disulfide bond between the variable domains of the single chain Fab fragments comprised in the antibody according to the invention is between heavy chain variable domain position 44 and light chain variable domain position 100. In one embodiment the optional disulfide bond between the variable domains of the single chain Fab fragments comprised in the antibody according to the invention is between heavy chain variable domain position 105 and light chain variable domain position 43 (numbering always according to EU index of Kabat).

In an embodiment single chain Fab fragment without the optional disulfide stabilization between the variable domains VH and VL of the single chain Fab fragments are preferred.

The term "peptide connector" as used within the invention denotes a peptide with amino acid sequences, which is preferably of synthetic origin. These peptide connectors according to invention are used to fuse the single chain Fab fragments to the C- or N-terminus of the full length antibody to form a multispecific antibody according to the invention. Preferably the peptide connectors under b) are peptides with an amino acid sequence with a length of at least 5 amino acids, preferably with a length of 5 to 100, more preferably of 10 to 50 amino acids. In one embodiment the peptide connector is (GxS)n or (GxS)nGm with G=glycine, S=serine, and (x=3, n=3, 4, 5 or 6, and m=0, 1, 2 or 3) (SEQ ID NOs: 20 and 21, respectively) or (x=4, n=2, 3, 4 or 5 and m=0, 1, 2 or 3) (SEQ ID NOs: 22 and 23, respectively), preferably x=4 and n=2 or 3, more preferably with x=4, n=2. In one embodiment the peptide connector is $(G_4S)_2$ (SEQ ID NO:24).

The term "linker" as used within the invention denotes a peptide with amino acid sequences, which is preferably of synthetic origin. These peptides according to invention are used to link a) VH-CH1 to VL-CL, b) VL-CL to VH-CH1, c) VH-CL to VL-CH1 or d) VL-CH1 to VH-CL to form the following single chain Fab fragments according to the invention a) VH-CH1-linker-VL-CL, b) VL-CL-linker-VH-CH1, c) VH-CL-linker-VL-CH1 or d) VL-CH1-linker-VH-CL. The linker within the single chain Fab fragments is a peptide with an amino acid sequence with a length of at least 30 amino acids, preferably with a length of 32 to 50 amino acids. In one embodiment the linker is (GxS)n with G=glycine, S=serine, (x=3, n=8, 9 or 10 and m=0, 1, 2 or 3) (SEQ ID NO:25) or (x=4 and n=6, 7 or 8 and m=0, 1, 2 or 3) (SEQ ID NO:26), preferably with x=4, n=6 or 7 and m=0, 1, 2 or 3, more preferably with x=4, n=7 and m=2. In one embodiment the linker is $(G_4S)_6G_2$ (SEQ ID NO:27).

To each C- or N-terminus of the heavy or light chain of the full length antibody. only one from the single chain Fab fragments under b) can be fused at the same time. Thus up to eight single chain Fab fragments can be fused to the full length antibody. Preferably the multispecific antibody according to the invention comprises one to four single chain Fab fragments. More preferably the multispecific antibody according to the invention comprises two identical single chain Fab fragments (preferably VL-CL-linker-VH-CH1) which are both fused to the two C-termini of the two heavy chains or to the two C-termini of the two light chains of the full length antibody under a). Such fusion results in two identical fusion peptides (either i) heavy chain and single chain Fab fragment or ii) light chain and single chain Fab fragment) which are coexpressed with either i) the light chain or the heavy chain of the full length antibody to give the multispecific antibody according to the invention (see FIGS. 3, 4 and 5).

In another preferred embodiment the multispecific antibody according to the invention comprises two identical single chain Fab fragments (preferably VH-CH1-linker-VL-CL) which are both fused to the two N-termini of the two heavy chains or to the two N-termini of the two light chains of the full length antibody under a). Such fusion results in two identical fusion peptides (either i) heavy chain and single chain Fab fragment or ii) light chain and single chain Fab fragment) which are coexpressed with either i) the light chain or the heavy chain of the full length antibody to give the multispecific antibody according to the invention.

Both parts of the multispecific antibody according to the invention comprise antigen-binding sites (the full length antibody according the invention comprises two, and each single chain Fab fragment comprises one antigen binding site). The terms "binding site" or "antigen-binding site" as used herein denotes the region(s) of the multispecific antibody according to the invention to which the respective antigen actually specifically binds. The antigen binding sites either in the full length antibody or in the single chain Fab fragment are formed each by a pair consisting of an antibody light chain variable domain (VL) and an antibody heavy chain variable domain (VH).

The antigen-binding sites that specifically bind to the desired antigen (e.g. EGFR) can be derived a) from known antibodies to the antigen (e.g. anti-EGFR antibodies) or b) from new antibodies or antibody fragments obtained by de novo immunization methods using inter alia either the antigen protein or nucleic acid or fragments thereof or by phage display.

An antigen-binding site of an antibody of the invention contains six complementarity determining regions (CDRs) which contribute in varying degrees to the affinity of the binding site for antigen. There are three heavy chain variable domain CDRs (CDRH1, CDRH2 and CDRH3) and three light chain variable domain CDRs (CDRL1, CDRL2 and CDRL3). The extent of CDR and framework regions (FRs) is determined by comparison to a compiled database of amino acid sequences in which those regions have been defined according to variability among the sequences.

Antibody specificity refers to selective recognition of the antibody for a particular epitope of an antigen. Natural antibodies, for example, are monospecific. The term "multispecific" antibody as used herein denotes an antibody that has two or more antigen-binding sites of which at least two bind to a different antigen or a different epitope of the same antigen. "Bispecific antibodies" according to the invention are antibodies which have two different antigen-binding specificities. Antibodies of the present invention are e.g. multispecific for at least two different antigens, i.e. EGFR as first antigen and IGF-1R as second antigen. In one embodiment of the invention the multispecific antibody according to the invention is bispecific. In another embodiment of the invention the multispecific antibody according to the invention is trispecific.

The term "monospecific" antibody as used herein denotes an antibody that has one or more binding sites each of which bind to the same epitope of the same antigen.

The term "valent" as used within the current application denotes the presence of a specified number of binding sites in an antibody molecule. A natural antibody for example or a full length antibody according to the invention has two binding sites and is bivalent. As such, the terms "trivalent", "tetravalent", "pentavalent" and "hexavalent" denote the presence of two binding site, three binding sites, four binding sites, five binding sites, and six binding sites, respectively, in an antibody molecule. The multispecific antibodies according to the invention are at least "trivalent". Preferably they are "trivalent", "tetravalent", "pentavalent" or "hexavalent", more preferably they are "trivalent" or "tetravalent".

Antibodies of the present invention have three or more binding sites and are multispecific, preferably bispecific or trispecific. As the multispecific antibodies according to the invention may be bispecific even in cases where there are more than three binding sites (i.e. that the antibody is tetravalent, pentavalent or hexavalent or multivalent). For an antibody with more than two antigen binding sites, some binding sites may be identical, so long as the protein has binding sites for two different antigens.

Another embodiment of the current invention is a multispecific antibody comprising
a) a full length antibody specifically binding to a first antigen and consisting of:
aa) two identical antibody heavy chains consisting of N-terminal to C-terminal direction of an antibody heavy chain variable domain (VH), an antibody constant heavy chain domain 1 (CH1), an antibody hinge region (HR), an antibody heavy chain constant domain 2 (CH2), and an antibody heavy chain constant domain 3 (CH3); and
ab) two identical antibody light chains consisting in N-terminal to C-terminal direction of an antibody light chain variable domain (VL), and an antibody light chain constant domain (CL) (VL-CL); and
b) one to four single chain Fab fragments specifically binding to one to four further antigens (preferably specifically binding to one further antigen),
wherein the single chain Fab fragments consist of an antibody heavy chain variable domain (VH) and an antibody constant domain 1 (CH1), an antibody light chain variable domain (VL), an antibody light chain constant domain (CL) and a linker, and wherein the antibody domains and the linker have one of the following orders in N-terminal to C-terminal direction:
ba) VH-CH1-linker-VL-CL, bb) VL-CL-linker-VH-CH1, bc) VH-CL-linker-VL-CH1 or bd) VL-CH1-linker-VH-CL;
wherein the linker is a peptide of at least 30 amino acids, preferably between 32 and 50 amino acids;
and wherein the single chain Fab fragments under b) are fused to the full length antibody under
a) via a peptide connector at the C- or N-terminus of the heavy or light chain of the full length antibody;
wherein the peptide connector is a peptide of at least 5 amino acids, preferably between 10 and 50 amino acids.

Within this embodiment, preferably one or two, more preferably two, single chain Fab fragments ba) VH-CH1-linker-VL-CL or bb) VL-CL-linker-VH-CH1, preferably bb) VL-CL-linker-VH-CH1, specifically binding to a second antigen are fused to the full length antibody via a peptide connector at the C-terminus of the heavy chain of the full length antibody, and the single chain Fab fragments are not disulfide stabilized.

One embodiment of the invention is a multispecific antibody according to the invention, wherein one or two single chain Fab fragments binding to a second antigen are fused to the full length antibody via a peptide connector at the C-terminus of the heavy chains of the full length antibody (bispecific antibody).

Preferably the multispecific antibody according to the invention comprises two identical single chain Fab fragments binding to a second antigen, which are either both fused to the heavy chain or which are both fused the light chain C- or N-termini. (bispecific antibody).

One embodiment of the invention is a multispecific antibody according to the invention, wherein two identical single chain Fab fragments VL-CL-linker-VH-CH1 or VH-CH1-linker-VL-CL, preferably VL-CL-linker-VH-CH1, binding to a second antigen are fused with their N-termini to the full length antibody via a peptide connector at the two C-termini of the two heavy chains or at the two C-termini of the two light chains of the full length antibody (tetravalent, bispecific antibody). In a preferred embodiment the multispecific antibody (preferably the tetravalent, bispecific antibody) according to the invention is containing a full length IgG and two identical single chain Fab fragments according to the invention as described above and specifically binds human IGF-1R as well as to human EGFR. These molecules are preferably based on the antigen-binding sites of the human anti-IGF-1R antibodies <IGF-1R> HUMAB Clone 18 (DSM ACC 2587; WO 2005/005635, abbreviated as <IGF-1R>Clone18 or <IGF-1R> AK18) and humanized <EGFR>ICR62 (WO 2006/082515 abbreviated as <EGFR>ICR62). These molecules simultaneously target and interfere with the action of two receptor tyrosine kinases on tumor cells. This dual activity causes a markedly improved anti-tumor activity compared to antibodies which interfere only with one of these receptors. The design, composition, generation and characterization of such molecules is shown in Examples 1-6.

Thus in one embodiment such a multispecific antibody according to the invention is characterized in that
i) the full length antibody is specifically binding to IGF1R and comprises in the heavy chain variable domain a CDR3 region of SEQ ID NO: 1, a CDR2 region of SEQ ID NO: 2, and a CDR1 region of SEQ ID NO:3, and in the light chain variable domain a CDR3 region of SEQ ID NO: 4, a CDR2 region of SEQ ID NO:5, and a CDR1 region of SEQ ID NO:6; and
ii) the single chain Fab fragment is specifically binding to EGFR and comprises in the heavy chain variable domain a CDR3 region of SEQ ID NO: 9, a CDR2 region of, SEQ ID NO: 10, and a CDR1 region of SEQ ID NO: 11, and in the light chain variable domain a CDR3 region of SEQ ID NO: 12, a CDR2 region of SEQ ID NO: 13, and a CDR1 region of SEQ ID NO: 14.

In one embodiment such a multispecific antibody according to the invention is characterized in that i) the full length antibody is specifically binding to IGF-1R and comprises as heavy chain variable domain SEQ ID NO: 7, and as light chain variable domain SEQ ID NO: 8, and
ii) the single chain Fab fragment is specifically binding to EGFR and comprises as heavy chain variable domain SEQ ID NO: 15, and as light chain variable domain a SEQ ID NO: 16.

In one embodiment such a multispecific antibody according to the invention is characterized in that
i) the full length antibody is specifically binding to EGFR and comprises in the heavy chain variable domain a CDR3 region of SEQ ID NO: 9, a CDR2 region of, SEQ ID NO: 10, and a CDR1 region of SEQ ID NO: 11, and in the light chain variable domain a CDR3 region of SEQ ID NO: 12, a CDR2 region of SEQ ID NO: 13, and a CDR1 region of SEQ ID NO: 14; and
ii) the single chain Fab fragment is specifically binding to IGF-1R and comprises in the heavy chain variable domain a CDR3 region of SEQ ID NO: 1, a CDR2 region of SEQ ID NO: 2, and a CDR1 region of SEQ ID NO:3, and in the light chain variable domain a CDR3 region of SEQ ID NO: 4, a CDR2 region of SEQ ID NO:5, and a CDR1 region of SEQ ID NO:6.

In one embodiment such a multispecific antibody according to the invention is characterized in that
i) the full length antibody is specifically binding to EGFR and comprises as heavy chain variable domain SEQ ID NO: 15, and as light chain variable domain a SEQ ID NO: 16, and
ii) the single chain Fab fragment is specifically binding to IGF1R and comprises as heavy chain variable domain SEQ ID NO: 7, and as light chain variable domain SEQ ID NO: 8.

One embodiment of the invention is a multispecific antibody according to the invention, wherein two identical single chain Fab fragments VL-CL-linker-VH-CH1 or VH-CH1-linker-VL-CL, preferably VL-CL-linker-VH-CH1, binding to a second antigen are fused with their C-termini to the full length antibody via a peptide connector at the two N-termini of the two heavy chains or at the two N-termini of the two light chains of the full length antibody.

One embodiment of the invention is a multispecific antibody according to the invention, wherein one single chain Fab fragment binding to a second antigen is fused to the full length antibody via a peptide connector at the C or N-terminus of one heavy chain or one light chain of the full length antibody. One embodiment of the invention is a multispecific antibody according to the invention, wherein one single chain Fab fragment binding to a second antigen is fused to the full length antibody via a peptide connector at the N-terminus of one heavy chain or one light chain of the full length antibody. One embodiment of the invention is a multispecific antibody according to the invention, wherein one single chain Fab fragment binding to a second antigen is fused to the full length antibody via a peptide connector at the C-terminus of one heavy chain or one light chain of the full length antibody (see e.g. FIG. 6).

Preferably the multispecific antibody according to the invention comprise two single chain Fab fragments binding to a second antigen and a third antigen (trispecific antibody) (see e.g. FIG. 7).

In another aspect of the current invention the multispecific antibody according to the invention comprises
a) a full length antibody binding to a first antigen consisting of two identical antibody heavy chains VH-CH1-HR-CH2-CH3 and two identical antibody light chains VL-CL; and
b) one to four single chain Fab fragments ba) VH-CH1-linker-VL-CL or bb) VL-CL-linker-VH-CH1, binding to one to four further antigens, wherein the single chain Fab fragments are linked to the full length antibody via a peptide connector at the C- or N-terminus of heavy and light chain of the full length antibody.

The full length antibodies of the invention comprise immunoglobulin constant regions of one or more immunoglobulin classes. Immunoglobulin classes include IgG, IgM, IgA, IgD, and IgE isotypes and, in the case of IgG and IgA, their subtypes. In a preferred embodiment, an full length antibody of the invention has a constant domain structure of an IgG type antibody.

The terms "monoclonal antibody" or "monoclonal antibody composition" as used herein refer to a preparation of antibody molecules of a single amino acid composition.

The term "chimeric antibody" refers to an antibody comprising a variable region, i.e., binding region, from one source or species and at least a portion of a constant region derived from a different source or species, usually prepared by recombinant DNA techniques. Chimeric antibodies comprising a murine variable region and a human constant region are preferred. Other preferred forms of "chimeric antibodies" encompassed by the present invention are those in which the constant region has been modified or changed from that of the original antibody to generate the properties according to the invention, especially in regard to C1q binding and/or Fc receptor (FcR) binding. Such chimeric antibodies are also referred to as "class-switched antibodies.". Chimeric antibodies are the product of expressed immunoglobulin genes comprising DNA segments encoding immunoglobulin variable regions and DNA segments encoding immunoglobulin constant regions. Methods for producing chimeric antibodies involve conventional recombinant DNA and gene transfection techniques are well known in the art. See, e.g., Morrison, S. L., et al., Proc. Natl. Acad. Sci. USA 81 (1984) 6851-6855; U.S. Pat. No. 5,202,238 and U.S. Pat. No. 5,204,244.

The term "humanized antibody" refers to antibodies in which the framework or "complementarity determining regions" (CDR) have been modified to comprise the CDR of an immunoglobulin of different specificity as compared to that of the parent immunoglobulin. In a preferred embodiment, a murine CDR is grafted into the framework region of a human antibody to prepare the "humanized antibody." See, e.g., Riechmann, L., et al., Nature 332 (1988) 323-327; and Neuberger, M. S., et al., Nature 314 (1985) 268-270. Particularly preferred CDRs correspond to those representing sequences recognizing the antigens noted above for chimeric antibodies. Other forms of "humanized antibodies" encompassed by the present invention are those in which the constant region has been additionally modified or changed from that of the original antibody to generate the properties according to the invention, especially in regard to C1q binding and/or Fc receptor (FcR) binding.

The term "human antibody", as used herein, is intended to include antibodies having variable and constant regions derived from human germ line immunoglobulin sequences. Human antibodies are well-known in the state of the art (van Dijk, M. A., and van de Winkel, J., G., Curr. Opin. Chem. Biol. 5 (2001) 368-374). Human antibodies can also be produced in transgenic animals (e.g., mice) that are capable, upon immunization, of producing a full repertoire or a selection of human antibodies in the absence of endogenous immunoglobulin production. Transfer of the human germ-line immunoglobulin gene array in such germ-line mutant mice will result in the production of human antibodies upon antigen challenge (see, e.g., Jakobovits, A., et al., Proc. Natl. Acad. Sci. USA 90 (1993) 2551-2555; Jakobovits, A., et al., Nature 362 (1993) 255-258; Brueggemann, M., et al., Year Immunol. 7 (1993) 33-40). Human antibodies can also be produced in phage display libraries (Hoogenboom, H. R., and Winter, G. J. Mol. Biol. 227 (1992) 381-388; Marks, J. D., et al., J. Mol. Biol. 222 (1991) 581-597). The techniques of Cole, et al. and Boerner, et al. are also available for the preparation of human monoclonal antibodies (Cole, S. P. C., et al., Monoclonal Antibodies and Cancer Therapy, Alan R. Liss, (1985) 77; and Boerner, P., et al., J. Immunol. 147 (1991) 86-95). As already mentioned for chimeric and humanized antibodies according to the invention the term "human antibody" as used herein also comprises such antibodies which are modified in the constant region to generate the properties according to the invention, especially in regard to C1q binding and/or FcR binding, e.g. by "class switching" i.e. change or mutation of Fc parts (e.g. from IgG1 to IgG4 and/or IgG1/IgG4 mutation.)

In case, the multispecific antibody according to the invention comprises one or three single chain Fab fragments (or the in case of two not identical single chain fragments which are attached both at the C- or N-termini of the either the heavy chain or light chain) which results in heterodimeric fusion peptides, the CH3 domains of the full length antibody according to the invention can be altered by the "knob-into-holes" technology which is described in detail with several examples in e.g. WO 96/027011, Ridgway, J. B., et al., Protein Eng 9 (1996) 617-621; and Merchant, A. M., et al., Nat Biotechnol 16 (1998) 677-681. In this method the interaction surfaces of the two CH3 domains are altered to increase the heterodimerisation of both heavy chains containing these two CH3 domains. Each of the two CH3 domains (of the two heavy chains) can be the "knob", while the other is the "hole". The introduction of a disulfide bridge stabilizes the heterodimers (Merchant, A. M., et al., Nature Biotech 16 (1998) 677-681; Atwell, S., et al., J. Mol. Biol. 270 (1997) 26-35) and increases the yield.

Thus in one aspect of the invention the multispecific antibody according to the invention comprises only one single chain Fab fragment and is further is characterized in that the CH3 domain of one heavy chain and the CH3 domain of the other heavy chain each meet at an interface which comprises an original interface between the antibody CH3 domains; wherein the interface is altered to promote the formation of the bivalent, bispecific antibody,
wherein the alteration is characterized in that:
a) the CH3 domain of one heavy chain is altered,
so that within the original interface the CH3 domain of one heavy chain that meets the original interface of the CH3 domain of the other heavy chain within the bivalent, bispecific antibody, an amino acid residue is replaced with an amino acid residue having a larger side chain volume, thereby generating a protuberance within the interface of the CH3 domain of one heavy chain which is positionable in a cavity within the interface of the CH3 domain of the other heavy chain and
b) the CH3 domain of the other heavy chain is altered,
so that within the original interface of the second CH3 domain that meets the original interface of the first CH3 domain within the trivalent, bispecific antibody
an amino acid residue is replaced with an amino acid residue having a smaller side chain volume, thereby generating a cavity within the interface of the second CH3 domain within which a protuberance within the interface of the first CH3 domain is positionable.

Preferably the amino acid residue having a larger side chain volume is selected from the group consisting of arginine (R), phenylalanine (F), tyrosine (Y), tryptophan (W).

Preferably the amino acid residue having a smaller side chain volume is selected from the group consisting of alanine (A), serine (S), threonine (T), valine (V).

In one aspect of the invention both CH3 domains are further altered by the introduction of cysteine (C) as amino acid in the corresponding positions of each CH3 domain such that a disulfide bridge between both CH3 domains can be formed.

In a preferred embodiment, the multispecific antibody comprising only one single chain Fab fragment and is a trivalent, bispecific antibody. The trivalent, bispecific antibody comprises a T366W mutation in the CH3 domain of the "knobs chain" and T366S, L368A, Y407V mutations in the CH3 domain of the "hole chain". An additional interchain disulfide bridge between the CH3 domains can also be used (Merchant, A. M., et al., Nature Biotech 16 (1998) 677-681) e.g. by introducing a Y349C mutation into the CH3 domain of the "knobs chain" and a E356C mutation or a S354C mutation into the CH3 domain of the "hole chain". Thus in a another preferred embodiment, the trivalent, bispecific antibody comprises Y349C, T366W mutations in one of the two CH3 domains and E356C, T366S, L368A, Y407V mutations in the other of the two CH3 domains or the trivalent, bispecific antibody comprises Y349C, T366W mutations in one of the two CH3 domains and S354C, T366S, L368A, Y407V mutations in the other of the two CH3 domains (the additional Y349C mutation in one CH3 domain and the additional E356C or S354C mutation in the other CH3 domain forming a interchain disulfide bridge) (numbering always according to EU index of Kabat). But also other knobs-in-holes technologies as described by EP 1870459A1, can be used alternatively or additionally. A preferred example for the trivalent, bispecific antibody are R409D; K370E mutations in the CH3 domain of the "knobs chain" and D399K; E357K mutations in the CH3 domain of the "hole chain" (numbering always according to EU index of Kabat).

In another preferred embodiment the trivalent, bispecific antibody (multispecific antibody comprising only one single chain Fab fragment) comprises a T366W mutation in the CH3 domain of the "knobs chain" and T366S, L368A, Y407V mutations in the CH3 domain of the "hole chain" and additionally R409D; K370E mutations in the CH3 domain of the "knobs chain" and D399K; E357K mutations in the CH3 domain of the "hole chain".

In another preferred embodiment the trivalent, bispecific antibody (multispecific antibody comprising only one single chain Fab fragment) comprises Y349C, T366W mutations in one of the two CH3 domains and S354C, T366S, L368A, Y407V mutations in the other of the two CH3 domains or the trivalent, bispecific antibody comprises Y349C, T366W mutations in one of the two CH3 domains and S354C, T366S, L368A, Y407V mutations in the other of the two CH3 domains and additionally R409D; K370E mutations in the CH3 domain of the "knobs chain" and D399K; E357K mutations in the CH3 domain of the "hole chain".

Thus one embodiment of the invention is a multispecific antibody according to the invention, wherein one single chain Fab fragment binding to a second antigen is fused to the full length antibody via a peptide connector at the C- or N-terminus of one heavy chain or one light chain of the full length antibody (preferably the C-terminus of one heavy chain), wherein the full length antibody comprises a T366W mutation in one of the two CH3 domains and T366S, L368A, Y407V mutations in the other of the two CH3 domains. Another embodiment of the invention is a multispecific antibody according to the invention, wherein one single chain Fab fragment binding to a second antigen is fused to the full length antibody via a peptide connector at the C- or N-terminus of one heavy chain or one light chain of the full length antibody (preferably the C-terminus of one heavy chain), wherein the full length antibody comprises Y349C, T366W mutations in one of the two CH3 domains and S354C, T366S, L368A, Y407V mutations in the other of the two CH3 domains. (see e.g. FIG. 6). Another embodiment of the invention is a multispecific antibody according to the invention, wherein one single chain Fab fragment binding to a second antigen is fused to the full length antibody via a peptide connector at the C- or N-terminus of one heavy chain or one light chain of the full length antibody (preferably the C-terminus of one heavy chain), wherein the full length antibody comprises Y349C, T366W mutations in one of the two CH3 domains and S354C, T366S, L368A, Y407V mutations in the other of the two CH3 domains.

The term "recombinant human antibody", as used herein, is intended to include all human antibodies that are prepared, expressed, created or isolated by recombinant means, such as antibodies isolated from a host cell such as a NS0 or CHO cell or from an animal (e.g. a mouse) that is transgenic for human immunoglobulin genes or antibodies expressed using a recombinant expression vector transfected into a host cell. Such recombinant human antibodies have variable and constant regions in a rearranged form. The recombinant human antibodies according to the invention have been subjected to in vivo somatic hypermutation. Thus, the amino acid sequences of the VH and VL regions of the recombinant antibodies are sequences that, while derived from and related to human germ line VH and VL sequences, may not naturally exist within the human antibody germ line repertoire in vivo.

The "variable domain" (variable domain of a light chain (VL), variable region of a heavy chain (VH) as used herein denotes each of the pair of light and heavy chains which is involved directly in binding the antibody to the antigen. The domains of variable human light and heavy chains have the same general structure and each domain comprises four framework (FR) regions whose sequences are widely conserved, connected by three "hypervariable regions" (or complementarity determining regions, CDRs). The framework regions adopt a β-sheet conformation and the CDRs may form loops connecting the β-sheet structure. The CDRs in each chain are held in their three-dimensional structure by the framework regions and form together with the CDRs from the other chain the antigen binding site. The antibody heavy and light chain CDR3 regions play a particularly important role in the binding specificity/affinity of the antibodies according to the invention and therefore provide a further object of the invention.

The terms "hypervariable region" or "antigen-binding portion of an antibody" when used herein refer to the amino acid residues of an antibody which are responsible for antigen-binding. The hypervariable region comprises amino acid residues from the "complementarity determining regions" or "CDRs". "Framework" or "FR" regions are those variable domain regions other than the hypervariable region residues as herein defined. Therefore, the light and heavy chains of an antibody comprise from N- to C-terminus the domains FR1, CDR1, FR2, CDR2, FR3, CDR3, and FR4. CDRs on each chain are separated by such framework amino acids. Especially, CDR3 of the heavy chain is the region which contributes most to antigen binding. CDR and FR regions are determined according to the standard definition of Kabat, et al., Sequences of Proteins of Immunological Interest, 5th ed., Public Health Service, National Institutes of Health, Bethesda, Md. (1991).

As used herein, the term "binding" or "specifically binding" refers to the binding of the antibody to an epitope of the antigen in an in vitro assay, preferably in a plasmon resonance assay (BIAcore, GE-Healthcare Uppsala, Sweden) with purified wild-type antigen. The affinity of the binding is defined by the terms ka (rate constant for the association of the antibody from the antibody/antigen complex), $k_D$ (dissociation constant), and $K_D$ ($k_D$/ka). Binding or specifically binding means a binding affinity ($K_D$) of $10^{-8}$ mol/l or less, preferably $10^{-9}$ M to $10^{-13}$ mol/l. Thus, an multispecific antibody according to the invention is specifically binding to each antigen for which it is specific with a binding affinity ($K_D$) of $10^{-8}$ mol/l or less, preferably $10^{-9}$ M to $10^{-13}$ mol/l.

Binding of the antibody to the FcγRIII can be investigated by a BIAcore assay (GE-Healthcare Uppsala, Sweden). The affinity of the binding is defined by the terms ka (rate constant for the association of the antibody from the antibody/antigen complex), $k_D$ (dissociation constant), and $K_D$ ($k_D$/ka).

The term "epitope" includes any polypeptide determinant capable of specific binding to an antibody. In certain embodiments, epitope determinant include chemically active surface groupings of molecules such as amino acids, sugar side chains, phosphoryl, or sulfonyl, and, in certain embodiments, may have specific three dimensional structural characteristics, and or specific charge characteristics. An epitope is a region of an antigen that is bound by an antibody.

In certain embodiments, an antibody is the to specifically bind an antigen when it preferentially recognizes its target antigen in a complex mixture of proteins and/or macromolecules.

The term "constant region" as used within the current applications denotes the sum of the domains of an antibody other than the variable region. The constant region is not involved directly in binding of an antigen, but exhibit various effector functions. Depending on the amino acid sequence of the constant region of their heavy chains, antibodies are divided in the classes: IgA, IgD, IgE, IgG and IgM, and several of these may be further divided into subclasses, such as IgG1, IgG2, IgG3, and IgG4, IgA1 and IgA2. The heavy chain constant regions that correspond to the different classes of antibodies are called α, β, ε, γ, and μ, respectively. The light chain constant regions (CL) which can be found in all five antibody classes are called δ (kappa) and λ (lambda).

The term "constant region derived from human origin" as used in the current application denotes a constant heavy chain region of a human antibody of the subclass IgG1, IgG2, IgG3, or IgG4 and/or a constant light chain kappa or lambda region. Such constant regions are well known in the state of the art and e.g. described by Kabat, E. A., (see e.g. Johnson, G. and Wu, T. T., Nucleic Acids Res. 28 (2000) 214-218; Kabat, E. A., et al., Proc. Natl. Acad. Sci. USA 72 (1975) 2785-2788).

While antibodies of the IgG4 subclass show reduced Fc receptor (FcγRIIIa) binding, antibodies of other IgG subclasses show strong binding. However Pro238, Asp265, Asp270, Asn297 (loss of Fc carbohydrate), Pro329, Leu234, Leu235, Gly236, Gly237, Ile253, Ser254, Lys288, Thr307, Gln311, Asn434, and His435 are residues which, if altered, provide also reduced Fc receptor binding (Shields, R. L., et al., J. Biol. Chem. 276 (2001) 6591-6604; Lund, J., et al., FASEB J. 9 (1995) 115-119; Morgan, A., et al., Immunology 86 (1995) 319-324; EP 0 307 434).

In one embodiment an antibody according to the invention has a reduced FcR binding compared to an IgG1 antibody and the full length parent antibody is in regard to FcR binding of IgG4 subclass or of IgG1 or IgG2 subclass with a mutation in S228, L234, L235 and/or D265, and/or contains the PVA236 mutation. In one embodiment the mutations in the full length parent antibody are S228P, L234A, L235A, L235E and/or PVA236. In another embodiment the mutations in the full length parent antibody are in IgG4 S228P and in IgG1 L234A and L235A. Constant heavy chain regions shown in SEQ ID NO: 17 and 18. In one embodiment the constant heavy chain region of the full length parent antibody is of SEQ ID NO: 17 with mutations L234A and L235A. In another embodiment the constant heavy chain region of the full length parent antibody is of SEQ ID NO: 18 with mutation S228P. In another embodiment the constant light chain region of the full length parent antibody is a kappa light chain region of SEQ ID NO: 19 or lambda light chain region. Preferably the constant heavy chain region of the full length parent antibody is of SEQ ID NO: 17 or of SEQ ID NO: 18 with mutation S228P.

The constant region of an antibody is directly involved in ADCC (antibody-dependent cell-mediated cytotoxicity) and CDC (complement-dependent cytotoxicity). Complement activation (CDC) is initiated by binding of complement factor C1q to the constant region of most IgG antibody subclasses. Binding of C1q to an antibody is caused by defined protein-protein interactions at the so called binding site. Such constant region binding sites are known in the state of the art and described e.g. by Lukas, T. J., et al., J. Immunol. 127 (1981) 2555-2560; Brunhouse, R. and Cebra, J. J., Mol. Immunol. 16 (1979) 907-917; Burton, D. R., et al., Nature 288 (1980) 338-344; Thommesen, J. E., et al., Mol. Immunol. 37 (2000) 995-1004; Idusogie, E. E., et al., J. Immunol. 164 (2000) 4178-4184; Hezareh, M., et al., J. Virol. 75 (2001) 12161-12168; Morgan, A., et al., Immunology 86 (1995) 319-324; and EP 0 307 434. Such constant region binding sites are, e.g., characterized by the amino acids L234, L235, D270, N297, E318, K320, K322, P331, and P329 (numbering according to EU index of Kabat).

The term "antibody-dependent cellular cytotoxicity (ADCC)" refers to lysis of human target cells by an antibody according to the invention in the presence of effector cells. ADCC is measured preferably by the treatment of a preparation of antigen expressing cells with an antibody according to the invention in the presence of effector cells such as freshly isolated PBMC or purified effector cells from buffy coats, like monocytes or natural killer (NK) cells or a permanently growing NK cell line.

The term "complement-dependent cytotoxicity (CDC)" denotes a process initiated by binding of complement factor C1q to the Fc part of most IgG antibody subclasses. Binding of C1q to an antibody is caused by defined protein-protein interactions at the so called binding site. Such Fc part binding sites are known in the state of the art (see above). Such Fc part binding sites are, e.g., characterized by the amino acids L234, L235, D270, N297, E318, K320, K322, P331, and P329 (numbering according to EU index of Kabat). Antibodies of subclass IgG1, IgG2, and IgG3 usually show complement activation including C1q and C3 binding, whereas IgG4 does not activate the complement system and does not bind C1q and/or C3.

In a further embodiment the multispecific antibody according to the invention is characterized in that the full length antibody is of human IgG1 subclass, or of human IgG1 subclass with the mutations L234A and L235A.

In a further embodiment the multispecific antibody according to the invention is characterized in that the full length antibody is of human IgG2 subclass.

In a further embodiment the multispecific antibody according to the invention is characterized in that the full length antibody is of human IgG3 subclass.

In a further embodiment the multispecific antibody according to the invention is characterized in that the full length antibody is of human IgG4 subclass or, of human IgG4 subclass with the additional mutation S228P.

Preferably the multispecific antibody according to the invention is characterized in that the full length antibody is of human IgG1 subclass, of human IgG4 subclass with the additional mutation S228P.

In a further embodiment the multispecific antibody according to the invention is characterized in that the full length antibody is modified (either by mutations in Fc regions or by glycoengineering) in a manner that increases affinity towards human Fc-gamma receptor IIIa to increase their competency to mediate ADCC. Methods to enhance the ADCC of antibodies by reducing the amount of fucose are described e.g. in WO 2005/018572, WO 2006/116260, WO 2006/114700, WO 2004/065540, WO 2005/011735, WO 2005/027966, WO 1997/028267, US 2006/0134709, US 2005/0054048, US 2005/0152894, WO 2003/035835, WO 2000/061739 Niwa, R., et al., J. Immunol. Methods 306 (2005) 151-160; Shinkawa, T., et al, J. Biol. Chem. 278 (2003) 3466-3473; WO 03/055993 or US 2005/0249722. Therefore in one embodiment the of the invention the multispecific antibody according to the invention is characterized in that the full length antibody is an afucosylated of IgG1 or IgG3 isotype wherein the amount of fucose is 60% or less of the total amount of oligosaccharides (sugars) at Asn297 (which means that at least 40% or more of the oligosaccharides of the Fc region at Asn297 are afucosylated).

The antibody according to the invention is produced by recombinant means. Thus, one aspect of the current invention is a nucleic acid encoding the antibody according to the invention and a further aspect is a cell comprising the nucleic acid encoding an antibody according to the invention. Methods for recombinant production are widely known in the state of the art and comprise protein expression in prokaryotic and eukaryotic cells with subsequent isolation of the antibody and usually purification to a pharmaceutically acceptable purity. For the expression of the antibodies as aforementioned in a host cell, nucleic acids encoding the respective modified light and heavy chains are inserted into expression vectors by standard methods. Expression is performed in appropriate prokaryotic or eukaryotic host cells like CHO cells, NS0 cells, SP2/0 cells, HEK293 cells, COS cells, PER.C6 cells, yeast, or *E. coli* cells, and the antibody is recovered from the cells (supernatant or cells after lysis). General methods for recombinant production of antibodies are well-known in the state of the art and described, for example, in the review articles of Makrides, S. C., Protein Expr. Purif. 17 (1999) 183-202; Geisse, S., et al., Protein Expr. Purif. 8 (1996) 271-282; Kaufman, R. J., Mol. Biotechnol. 16 (2000) 151-160; Werner, R. G., Drug Res. 48 (1998) 870-880.

The multispecific antibodies according to the invention are suitably separated from the culture medium by conventional immunoglobulin purification procedures such as, for example, protein A-Sepharose, hydroxylapatite chromatography, gel electrophoresis, dialysis, or affinity chromatography. DNA and RNA encoding the monoclonal antibodies is readily isolated and sequenced using conventional procedures. The hybridoma cells can serve as a source of such DNA and RNA. Once isolated, the DNA may be inserted into expression vectors, which are then transfected into host cells such as HEK 293 cells, CHO cells, or myeloma cells that do not otherwise produce immunoglobulin protein, to obtain the synthesis of recombinant monoclonal antibodies in the host cells.

Amino acid sequence variants (or mutants) of the multispecific antibody are prepared by introducing appropriate nucleotide changes into the antibody DNA, or by nucleotide synthesis. Such modifications can be performed, however, only in a very limited range, e.g. as described above. For example, the modifications do not alter the above mentioned antibody characteristics such as the IgG isotype and antigen binding, but improve the yield of the recombinant production, protein stability or facilitate the purification.

The term "host cell" as used in the current application denotes any kind of cellular system which can be engineered to generate the antibodies according to the current invention. In one embodiment HEK293 cells and CHO cells are used as host cells.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included. Where distinct designations are intended, it will be clear from the context.

Expression in NS0 cells is described by, e.g., Barnes, L. M., et al., Cytotechnology 32 (2000) 109-123; Barnes, L. M., et al., Biotech. Bioeng. 73 (2001) 261-270. Transient expression is described by, e.g., Durocher, Y., et al., Nucl. Acids. Res. 30 (2002) E9. Cloning of variable domains is described by Orlandi, R., et al., Proc. Natl. Acad. Sci. USA 86 (1989) 3833-3837; Carter, P., et al., Proc. Natl. Acad. Sci. USA 89 (1992) 4285-4289; and Norderhaug, L., et al., J. Immunol. Methods 204 (1997) 77-87. A preferred transient expression system (HEK 293) is described by Schlaeger, E.-J., and Christensen, K., in Cytotechnology 30 (1999) 71-83 and by Schlaeger, E.-J., in J. Immunol. Methods 194 (1996) 191-199.

The control sequences that are suitable for prokaryotes, for example, include a promoter, optionally an operator sequence, and a ribosome binding site. Eukaryotic cells are known to utilize promoters, enhancers and polyadenylation signals.

A nucleic acid is "operably linked" when it is placed in a functional relationship with another nucleic acid sequence. For example, DNA for a pre-sequence or secretory leader is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

Purification of antibodies is performed in order to eliminate cellular components or other contaminants, e.g. other cellular nucleic acids or proteins, by standard techniques, including alkaline/SDS treatment, CsCl banding, column chromatography, agarose gel electrophoresis, and others well known in the art. See Ausubel, F., et al., ed. Current Protocols in Molecular Biology, Greene Publishing and Wiley Interscience, New York (1987). Different methods are well established and widespread used for protein purification, such as affinity chromatography with microbial proteins (e.g. protein A or protein G affinity chromatography), ion exchange chromatography (e.g. cation exchange (carboxymethyl resins), anion exchange (amino ethyl resins) and mixed-mode exchange), thiophilic adsorption (e.g. with beta-mercaptoethanol and other SH ligands), hydrophobic interaction or aromatic adsorption chromatography (e.g. with phenyl-sepharose, aza-arenophilic resins, or m-aminophenylboronic acid), metal chelate affinity chromatography (e.g. with Ni(II)- and Cu(II)-affinity material), size exclusion chromatography, and electrophoretical methods (such as gel electrophoresis, capillary electrophoresis) (Vijayalakshmi, M. A., Appl. Biochem. Biotech. 75 (1998) 93-102).

The term "transformation" as used herein refers to process of transfer of a vectors/nucleic acid into a host cell. If cells without formidable cell wall barriers are used as host cells, transfection is carried out e.g. by the calcium phosphate precipitation method as described by Graham, F. L., and van der Eb, A. J., Virology 52 (1973) 456-467. However, other methods for introducing DNA into cells such as by nuclear injection or by protoplast fusion may also be used. If prokaryotic cells or cells which contain substantial cell wall constructions are used, e.g. one method of transfection is calcium treatment using calcium chloride as described by Cohen, S, N., et al., PNAS. 69 (1972) 2110-2114.

As used herein, "expression" refers to the process by which a nucleic acid is transcribed into mRNA and/or to the process by which the transcribed mRNA (also referred to as transcript) is subsequently being translated into peptides, polypeptides, or proteins. The transcripts and the encoded polypeptides are collectively referred to as gene product. If the polynucleotide is derived from genomic DNA, expression in a eukaryotic cell may include splicing of the mRNA.

A "vector" is a nucleic acid molecule, in particular self-replicating, which transfers an inserted nucleic acid molecule into and/or between host cells. The term includes vectors that function primarily for insertion of DNA or RNA into a cell (e.g., chromosomal integration), replication of vectors that function primarily for the replication of DNA or RNA, and expression vectors that function for transcription and/or translation of the DNA or RNA. Also included are vectors that provide more than one of the functions as described.

An "expression vector" is a polynucleotide which, when introduced into an appropriate host cell, can be transcribed and translated into a polypeptide. An "expression system" usually refers to a suitable host cell comprised of an expression vector that can function to yield a desired expression product.

It has now been found that the multispecific antibodies according to the invention have improved characteristics such as biological or pharmacological activity, pharmacokinetic properties or toxicity. They can be used e.g. for the treatment of diseases such as cancer.

One aspect of the invention is a pharmaceutical composition comprising an antibody according to the invention. Another aspect of the invention is the use of an antibody according to the invention for the manufacture of a pharmaceutical composition. A further aspect of the invention is a method for the manufacture of a pharmaceutical composition comprising an antibody according to the invention. In another aspect, the present invention provides a composition, e.g. a pharmaceutical composition, containing an antibody according to the present invention, formulated together with a pharmaceutical carrier.

One embodiment of the invention is the multispecific, preferably bispecific antibody according to the invention for the treatment of cancer.

Another aspect of the invention is the pharmaceutical composition for the treatment of cancer.

Another aspect of the invention is the use of an antibody according to the invention for the manufacture of a medicament for the treatment of cancer.

Another aspect of the invention is method of treatment of patient suffering from cancer by administering an antibody according to the invention to a patient in the need of such treatment.

As used herein, "pharmaceutical carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g. by injection or infusion).

A composition of the present invention can be administered by a variety of methods known in the art. As will be appreciated by the skilled artisan, the route and/or mode of administration will vary depending upon the desired results. To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Pharmaceutical carriers include sterile aqueous solutions or dispersions and sterile powders for the extemporaneous preparation of sterile injectable solutions or dispersion. The use of such media and agents for pharmaceutically active substances is known in the art.

The phrases "parenteral administration" and "administered parenterally" as used herein means modes of administration other than enteral and topical administration, usually by injection, and includes, without limitation, intravenous, intramuscular, intra-arterial, intrathecal, intracapsular, intraorbital, intracardiac, intradermal, intraperitoneal, transtracheal, subcutaneous, subcuticular, intra-articular, subcapsular, subarachnoid, intraspinal, epidural and intrasternal injection and infusion.

The term cancer as used herein refers to proliferative diseases, such as lymphomas, lymphocytic leukemias, lung cancer, non small cell lung (NSCL) cancer, bronchioloalveolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma and Ewings sarcoma, including refractory versions of any of the above cancers, or a combination of one or more of the above cancers.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol, sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The composition must be sterile and fluid to the extent that the composition is deliverable by syringe. In addition to water, the carrier preferably is an isotonic buffered saline solution.

Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition.

| | Description of the Amino acid Sequences |
|---|---|
| SEQ ID NO: 1 | heavy chain CDR3, <IGF-1R> HUMAB-Clone 18 |
| SEQ ID NO: 2 | heavy chain CDR2, <IGF-1R> HUMAB-Clone 18 |
| SEQ ID NO: 3 | heavy chain CDR1, <IGF-1R> HUMAB-Clone 18 |
| SEQ ID NO: 4 | light chain CDR3, <IGF-1R> HUMAB-Clone 18 |
| SEQ ID NO: 5 | light chain CDR2, <IGF-1R> HUMAB-Clone 18 |
| SEQ ID NO: 6 | light chain CDR1, <IGF-1R> HUMAB-Clone 18 |
| SEQ ID NO: 7 | heavy chain variable domain, <IGF-1R> HUMAB-Clone 18 |
| SEQ ID NO: 8 | light chain variable domain, <IGF-1R> HUMAB-Clone 18 |
| SEQ ID NO: 9 | heavy chain CDR3, humanized <EGFR>ICR62 |
| SEQ ID NO: 10 | heavy chain CDR2, humanized <EGFR>ICR62 |
| SEQ ID NO: 11 | heavy chain CDR1, humanized <EGFR>ICR62 |
| SEQ ID NO: 12 | light chain CDR3, humanized <EGFR>ICR62 |
| SEQ ID NO: 13 | light chain CDR2, humanized <EGFR>ICR62 |
| SEQ ID NO: 14 | light chain CDR1, humanized <EGFR>ICR62 |
| SEQ ID NO: 15 | heavy chain variable domain, humanized <EGFR>ICR62-I-HHD |
| SEQ ID NO: 16 | light chain variable domain, humanized <EGFR>ICR62-I-KC |
| SEQ ID NO: 17 | human heavy chain constant region derived from IgG1 |
| SEQ ID NO: 18 | human heavy chain constant region derived from IgG4 |
| SEQ ID NO: 19 | kappa light chain constant region |

The following examples, sequence listing and figures are provided to aid the understanding of the present invention, the true scope of which is set forth in the appended claims. It is understood that modifications can be made in the procedures set forth without departing from the spirit of the invention.

DESCRIPTION OF THE FIGURES

FIG. 1 Schematic structure of a full length antibody without CH4 domain specifically binding to a first antigen 1 with two pairs of heavy and light chain which comprise variable and constant domains in a typical order.

FIG. 9 HP-SEC analyses of scFab containing bispecific antibody derivatives scFab-XGFR1

FIG. 10 Binding of scFab-XGFR1 and scFab-XGFR2 to EGFR and IGF1R

EXPERIMENTAL PROCEDURE

Examples

Materials & General Methods

Figure 2:
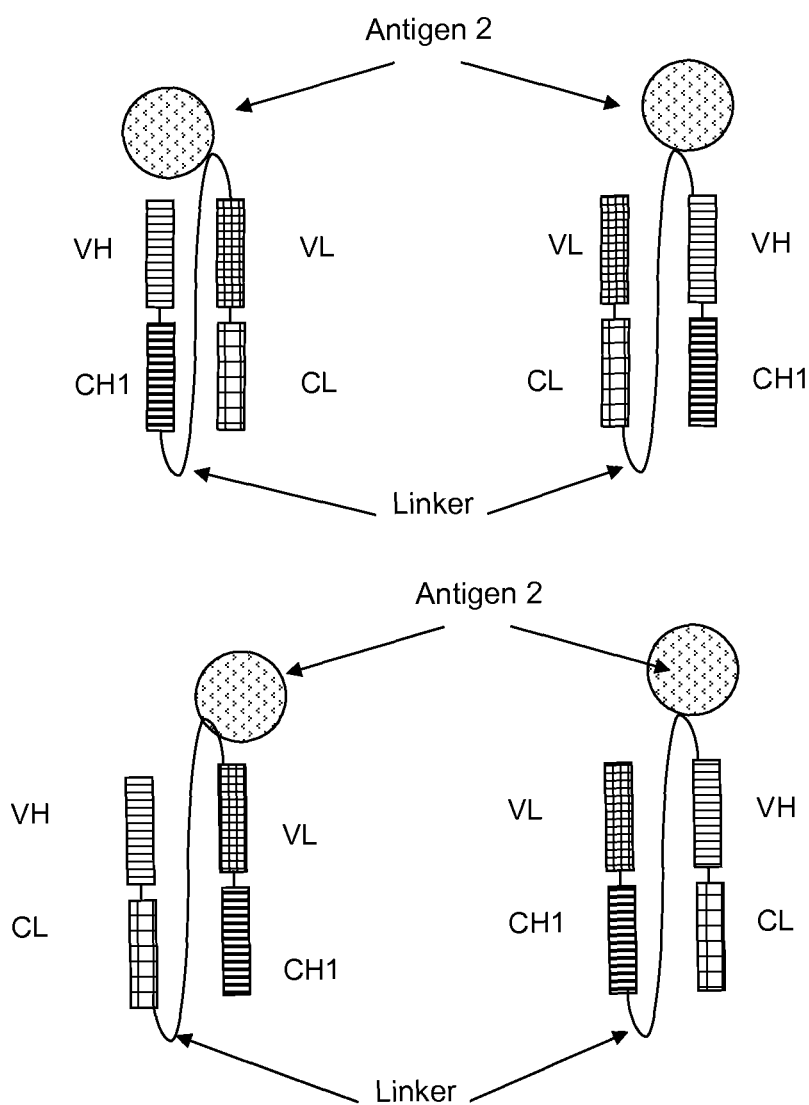
FIG. 2 Schematic structure of the four possible single chain Fab fragments specifically binding e.g. to second antigen 2
Figure 3:
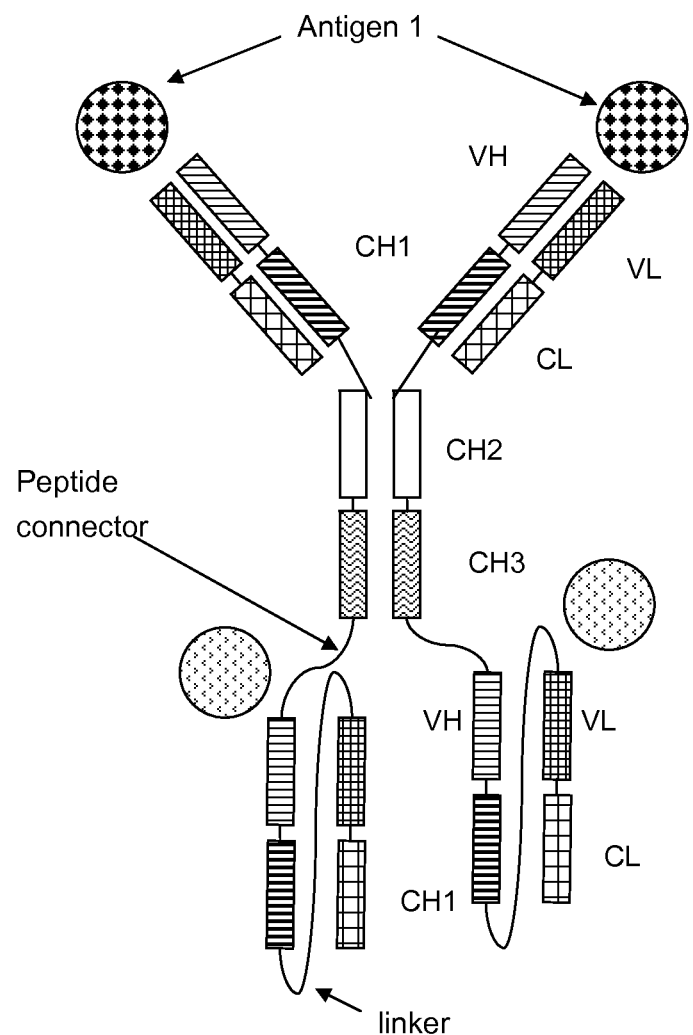
FIG. 3 Schematic structure of a multispecific antibodies according to the invention comprising a full length antibody specifically binding to a first antigen 1 and two single chain Fabs specifically binding to second antigen 2-bispecific tetravalent example FIG. 4 Bispecific antibodies according to the invention comprising a full length antibody specifically binding to IGF-1R and two identical single chain Fabs specifically binding to EGFR-ScFab-XGFR1 molecules A, B, C, and D and expression levels after purification
A: scFab (VH-CH1-linker-VL-CL) fused to C-Terminus of heavy chain
B: scFab (VH-CH1-linker-VL-CL with additional VH44-VL100 disulfide bridge fused) to C-Terminus of heavy chain
C: scFab (VH-CH1-linker-VL-CL) fused to C-Terminus of light chain
D: scFab (VH-CH1-linker-VL-CL with additional VH44-VL100 disulfide bridge fused) to C-Terminus of light chain FIG. 5 Bispecific antibodies according to the invention comprising a full length antibody specifically binding to EGFR and two identical single chain Fabs specifically binding to IGF-1R-ScFab-XGFR2 molecules A, B, C, and D
A: scFab (VH-CH1-linker-VL-CL) fused to C-Terminus of heavy chain
B: scFab (VH-CH1-linker-VL-CL with additional VH44-VL100 disulfide bridge fused) to C-Terminus of heavy chain
C: scFab (VH-CH1-linker-VL-CL) fused to C-Terminus of light chain
D: scFab (VH-CH1-linker-VL-CL with additional VH44-VL100 disulfide bridge fused) to C-Terminus of light chain FIG. 6 Schematic structure of a multispecific antibodies according to the invention comprising a full length antibody specifically binding to a first antigen 1 and one single chain Fab specifically binding to a second antigen 2—bispecific trivalent example with knobs and holes FIG. 7 Schematic structure of a multispecific antibodies according to the invention comprising a full length antibody specifically binding to a first antigen 1 one single chain Fab specifically binding to a second antigen 2 and one single chain Fab specifically binding to a third antigen 3—trispecific tetravalent example with knobs and holes FIG. 8 SDS-PAGE analyses of single chain Fab containing bispecific antibody derivatives scFab-XGFR1
1: scFab-XGFR1_4720 (Not reduced)
2: scFab-XGFR1_4721 (Not reduced)
3: scFab-XGFR1_4720 (reduced)
4: scFab-XGFR1_4721 (reduced)

General information regarding the nucleotide sequences of human immunoglobulins light and heavy chains is given in: Kabat, E. A., et al., Sequences of Proteins of Immunological Interest, 5th ed., Public Health Service, National Institutes of Health, Bethesda, Md. (1991). Amino acids of antibody chains are numbered and referred to according to EU numbering (Edelman, G. M., et al., Proc. Natl. Acad. Sci. USA 63 (1969) 78-85; Kabat, E. A., et al., Sequences of Proteins of Immunological Interest, 5th ed., Public Health Service, National Institutes of Health, Bethesda, Md., (1991).

Recombinant DNA Techniques

Standard methods were used to manipulate DNA as described in Sambrook, J., et al., Molecular cloning: A laboratory manual; Cold Spring Harbor Laboratory Press, Cold Spring Harbor, N.Y., 1989. The molecular biological reagents were used according to the manufacturer's instructions.

Gene Synthesis

Desired gene segments were prepared from oligonucleotides made by chemical synthesis. The 600-1800 bp long gene segments, which are flanked by singular restriction endonuclease cleavage sites, were assembled by annealing and ligation of oligonucleotides including PCR amplification and subsequently cloned via the indicated restriction sites e.g. BamHI/BstEII, BamHI/BsiWI, BstEII/NotI or BsiWI/NotI into a pcDNA 3.1/Zeo(+) (Invitrogen) based on a pUC cloning vector. The DNA sequences of the subcloned gene fragments were confirmed by DNA sequencing. Gene synthesis fragments were ordered according to given specifications at Geneart (Regensburg, Germany).

DNA Sequence Determination

DNA sequences were determined by double strand sequencing performed at Sequiserve GmbH (Vaterstetten, Germany).

DNA and Protein Sequence Analysis and Sequence Data Management

The GCG's (Genetics Computer Group, Madison, Wis.) software package version 10.2 and Invitrogens Vector NT1 Advance suite version 9.1 was used for sequence creation, mapping, analysis, annotation and illustration.

Cell Culture Techniques

Standard cell culture techniques were used as described in Current Protocols in Cell Biology (2000), Bonifacino, J. S., Dasso, M., Harford, J. B., Lippincott-Schwartz, J., and Yamada, K. M., (eds.), John Wiley & Sons, Inc.

Transient Expression of Immunoglobulin Variants in HEK293F Cells

The multispecific antibodies were expressed by transient transfection of human embryonic kidney 293-F cells using the FreeStyle™ 293 Expression System according to the manufacturer's instruction (Invitrogen, USA). Briefly, suspension FreeStyle™ 293-F cells were cultivated in FreeStyle™ 293 Expression medium at 37° C./8% $CO_2$ and the cells were seeded in fresh medium at a density of $1-2\times10^6$ viable cells/ml on the day of transfection. The DNA-293Fectin™ complexes were prepared in Opti-MEM® I medium (Invitrogen, USA) using 333 µl of 293Fectin™ (Invitrogen, Germany) and 250 µg of heavy and light chain plasmid DNA in a 1:1 molar ratio for a 250 ml final transfection volume. Bispecific antibody containing cell culture supernatants were clarified 7 days after transfection by centrifugation at 14000 g for 30 minutes and filtration through a sterile filter (0.22 µm). Supernatants were stored at −20° C. until purification.

Protein Determination

The protein concentration of purified antibodies and derivatives was determined by determining the optical density (OD) at 280 nm with the OD at 320 nm as the background correction, using the molar extinction coefficient calculated on the basis of the amino acid sequence according to Pace, C. N., et. al., Protein Science, 4 (1995) 2411-2423.

Antibody Concentration Determination in Supernatants

The concentration of antibodies and derivatives in cell culture supernatants was measured by affinity HPLC chromatography. Briefly, cell culture supernatants containing antibodies and derivatives that bind to Protein A were applied to an Applied Biosystems Poros A/20 column in 200 mM KH2PO4, 100 mM sodium citrate, pH 7.4 and eluted from the matrix with 200 mM NaCl, 100 mM citric acid, pH 2.5 on an UltiMate 3000 HPLC system (Dionex). The eluted protein was quantified by UV absorbance and integration of peak areas. A purified standard IgG1 antibody served as a standard.

Protein Purification

The secreted antibodies were purified from the supernatant in two steps by affinity chromatography using Protein A-Sepharose™ (GE Healthcare, Sweden) and Superdex200 size exclusion chromatography. Briefly, the bispecific and trispecific antibody containing clarified culture supernatants were applied on a HiTrap ProteinA HP (5 ml) column equilibrated with PBS buffer (10 mM $Na_2HPO_4$, 1 mM $KH_2PO_4$, 137 mM NaCl and 2.7 mM KCl, pH 7.4). Unbound proteins were washed out with equilibration buffer. The bispecific antibodies were eluted with 0.1 M citrate buffer, pH 2.8, and the protein containing fractions were neutralized with 0.1 ml 1 M Tris, pH 8.5. Then, the eluted protein fractions were pooled, concentrated with an Amicon Ultra centrifugal filter device (MWCO: 30 K, Millipore) to a volume of 3 ml and loaded on a Superdex200 HiLoad 120 ml 16/60 gel filtration column (GE Healthcare, Sweden) equilibrated with 20 mM Histidin, 140 mM NaCl, pH 6.0. Monomeric antibody fractions were pooled, snap-frozen and stored at −80° C. Parts of the samples were provided for subsequent protein analytics and characterization.

Analysis of Purified Proteins

The protein concentration of purified protein samples was determined by measuring the optical density (OD) at 280 nm, using the molar extinction coefficient calculated on the basis of the amino acid sequence. The purity of the bispecific antibodies were analyzed by SDS-PAGE in the presence and absence of a reducing agent (5 mM 1,4-dithiotreitol) and staining with Coomassie brilliant blue. The NuPAGE® Pre-Cast gel system (Invitrogen, USA) was used according to the manufacturer's instruction (4-20% Tris-Glycine gels). The aggregate content of bispecific antibody samples was analyzed by high-performance SEC on an UltiMate 3000 HPLC system (Dionex) using a Superdex 200 analytical size-exclusion column (GE Healthcare, Sweden) in 200 mM $KH_2PO_4$, 250 mM KCl, pH 7.0 running buffer at 25° C. 25 µg protein were injected on the column at a flow rate of 0.5 ml/min and eluted isocratic over 50 minutes. For stability analysis, concentrations of 0.1 mg/ml, 1 mg/ml and 3 mg/ml of purified proteins were prepared and incubated at 4° C., 37° C. for 7 days and then evaluated by high-performance SEC. The integrity of the amino acid backbone of reduced bispecific antibody light and heavy chains was verified by NanoElectrospray Q-TOF mass spectrometry after removal of N-glycans by enzymatic treatment with Peptide-N-Glycosidase F (Roche Molecular Biochemicals).

Example 1

Design of Multispecific Antibodies According to the Invention Molecules which Recognize Human IGF1-Receptor as Well as Human EGF-Receptor In the following as one embodiment of the invention tetravalent bispecific antibodies comprising a full length antibody binding to a first antigen (IGF-1R or EGFR) with two single chain Fab fragments binding to a second different antigen (the other of IGF-1R or EGFR) connected via peptide connector to the full length antibody (either both single chain Fab fragments at the two C-termini of the heavy chain or at the two C-termini of the light chain) are exemplified. The antibody domains and the linker in the single chain Fab fragment have the following order in N-terminal to C-terminal direction: VL-CL-linker-VH-CH1.

As heavy chain variable domain VH for the <IGF-1R> antigen binding site SEQ ID NO: 15 was used. As light chain variable domain VL for the <IGF-1R> antigen binding site SEQ ID NO: 16 was used.

As heavy chain variable domain VH for the <EGFR> antigen binding site SEQ ID NO: 7 was used. As light chain variable domain VL for the <EGFR> antigen binding site SEQ ID NO: 8 was used.

By gene synthesis and recombinant molecular biology techniques, VL-CL and VH-CH1, comprising the VH and VL of the respective antigen binding site were linked by a glycine serine (G4S)n single-chain-linker to give a single chain Fab fragment VL-CL-linker-VH-CH1, which was attached to the C-terminus of the antibody heavy or light chain using (G4S)n linker $G_4S$ is SEQ ID NO:28.

Optionally, cystine residues were introduced in the VH (including Kabat position 44) and VL (including Kabat position 100) domain of the single chain Fab fragment according to techniques as described earlier (e.g. WO 94/029350; Reiter, Y., et al., Nature biotechnology 14 (1996) 1239-1245; Young, N. M., et al., FEBS Letters 377 (1995) 135-139; or Rajagopal, V., et al., Protein Engineering 10 (1997) 1453-59).

All these molecules were recombinantly produced, purified and characterized and protein expression, stability and biological activity was evaluated.

Figure 4:
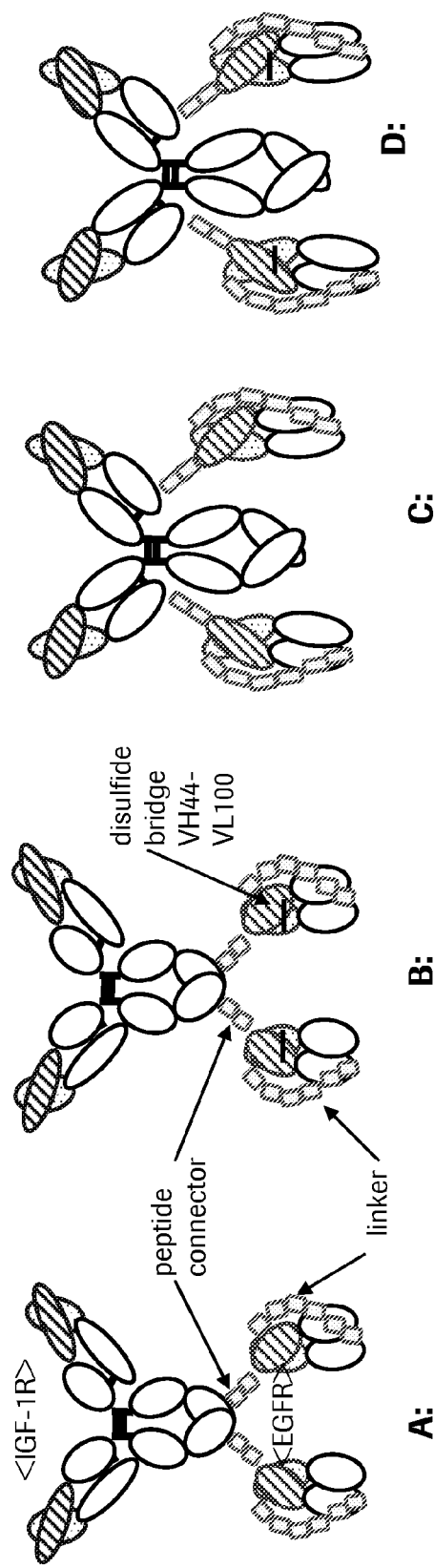
Figure 5:
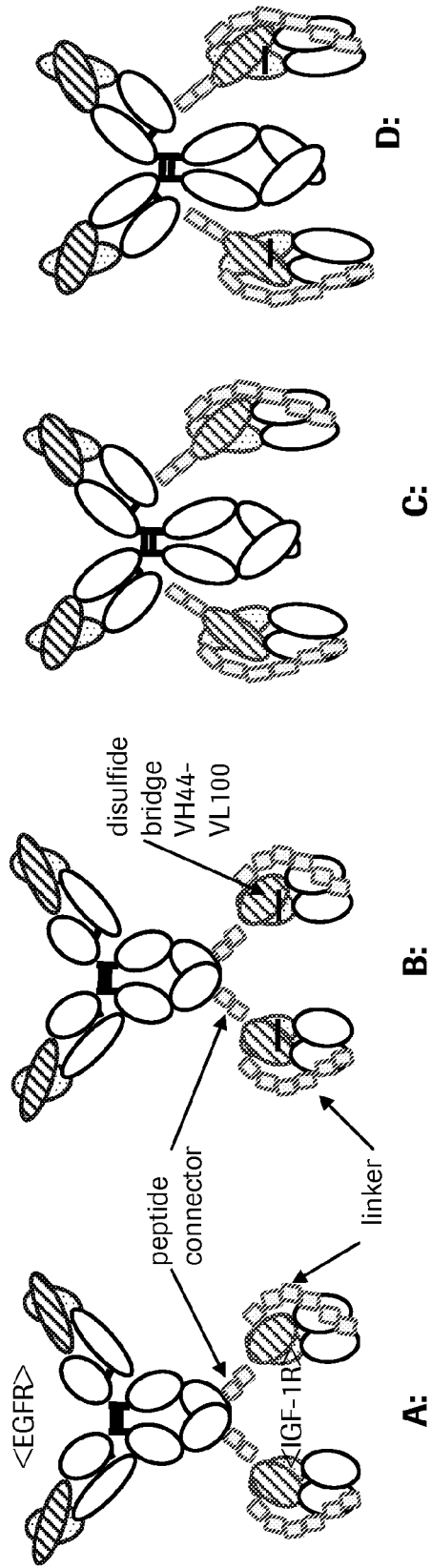
Figure 6:
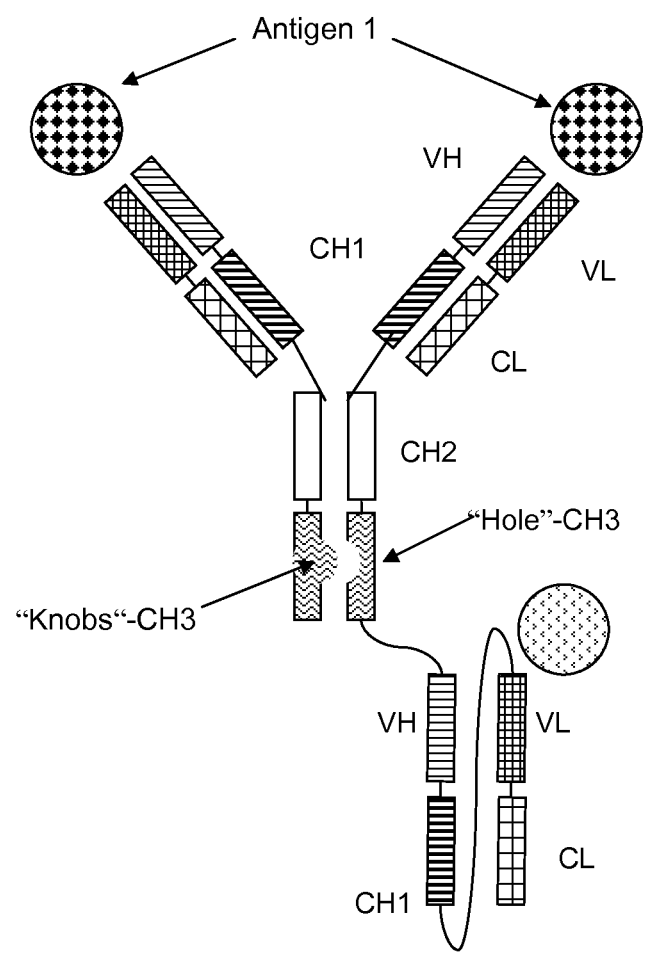

A summary of the multispecific antibody designs that were applied to generate tetravalent, bispecific <EGFR-IGF-1R>, <IGF-1R-EGFR> antibodies is given in Table 1. For this study, we use the term 'scFab-Ab' to describe the various tetravalent protein entities. A representation of the designed formats is shown in FIGS. 4 and 5 and listed in Table 1. $(G_4S)_6GG$ is SEQ ID NO:27; $(G_4S)_2$ is SEQ ID NO:24.

VL of the additional binding moieties was applied. For that we introduced single cysteine replacements within VH and VL of the scFab at defined positions (positions VH44NL100 according to the Kabat numbering scheme). These mutations enable the formation of stable interchain disulfides between VH and VL, which in turn stabilize the resulting disulfide-stabilized scFab module. Introduction of the VH44/VL100 disulfides in scFabs did not significantly interfere with protein expression levels and in some instance even improved expression yields (see FIGS. 4 and 5).

The bispecific antibodies were expressed by transient transfection of human embryonic kidney 293-F cells using the FreeStyle™ 293 Expression System according to the manufacturer's instruction (Invitrogen, USA). Briefly, suspension FreeStyle™ 293-F cells were cultivated in Fre-

TABLE 1

The different bispecific anti IGF1R and antiEGFR tetravalent antibody formats with C- terminal single chain Fab fragment attachments and the corresponding scFab-Ab-nomenclature.

| Molecule Name (ScFab-Ab-nomenclature for bispecific antibodies) | Full length Antibody backbone derived from | Single chain Fab fragment derived from | Variable Domains VH and VL: SEQ ID NO: | Position of single chain Fab attached to antibody | linker | Peptide connector | scFab disulfide VH44/VL100 stabilized |
|---|---|---|---|---|---|---|---|
| scFab-XGFR1__2720 | <IGF1R> | <EGFR> | 7, 8, 15, 16 | C-terminus H chain | $(G_4S)_6GG$ | $(G_4S)_2$ | NO |
| scFab-XGFR1__2721 | <IGF1R> | <EGFR> | 7, 8, 15, 16 | C-terminus H chain | $(G_4S)_6GG$ | $(G_4S)_2$ | YES |
| scFab-XGFR1__4720 | <IGF1R> | <EGFR> | 7, 8, 15, 16 | C-terminus L chain | $(G_4S)_6GG$ | $(G_4S)_2$ | NO |
| scFab-XGFR1__4721 | <IGF1R> | <EGFR> | 7, 8, 15, 16 | C-terminus L chain | $(G_4S)_6GG$ | $(G_4S)_2$ | YES |
| scFab-XGFR2__2720 | <EGFR> | <IGF1R> | 7, 8, 15, 16 | C-terminus H chain | $(G_4S)_6GG$ | $(G_4S)_2$ | NO |
| scFab-XGFR2__2721 | <EGFR> | <IGF1R> | 7, 8, 15, 16 | C-terminus H chain | $(G_4S)_6GG$ | $(G_4S)_2$ | YES |
| scFab-XGFR2__4720 | <EGFR> | <IGF1R> | 7, 8, 15, 16 | C-terminus L chain | $(G_4S)_6GG$ | $(G_4S)_2$ | NO |
| scFab-XGFR2__4721 | <EGFR> | <IGF1R> | 7, 8, 15, 16 | C-terminus L chain | $(G_4S)_6GG$ | $(G_4S)_2$ | YES |

Example 2

Expression & Purification of Bispecific <EGFR-IGF1R> Antibody scFabXGFR1 Molecules Light and heavy chains of the corresponding bispecific antibodies were constructed in expression vectors carrying pro- and eukaryotic selection markers. These plasmids were amplified in *E. coli*, purified, and subsequently transfected for transient expression of recombinant proteins in HEK293F cells (utilizing Invitrogen's freestyle system). After 7 days, HEK 293 cell supernatants were harvested and purified by protein A and size exclusion chromatography. Homogeneity of all bispecific antibody constructs was confirmed by SDS-PAGE under non reducing and reducing conditions. Under reducing conditions (FIG. 8), polypeptide chains carrying C- and N-terminal scFab fusions showed upon SDS-PAGE apparent molecular sizes analogous to the calculated molecular weights. Expression levels of all constructs were analyzed by Protein A HPLC and were similar to expression yields of 'standard' IgGs, or in some cases somewhat lower. Average protein yields were between 1.5 and 10 mg of protein per liter of cell-culture supernatant in such non-optimized transient expression experiments (FIGS. 4 and 5).

HP-Size exclusion chromatography analysis of the purified proteins showed some tendency to aggregate for recombinant molecules. To address the problems with aggregation of such bispecific antibodies, disulfide-stabilization between VH and eStyle™ 293 Expression medium at 37° C./8% $CO_2$ and the cells were seeded in fresh medium at a density of $1-2 \times 10^6$ viable cells/ml on the day of transfection. The DNA-293Fectin™ complexes were prepared in Opti-MEM® I medium (Invitrogen, USA) using 333 µl of 293Fectin™ (Invitrogen, Germany) and 250 µg of heavy and light chain plasmid DNA in a 1:1 molar ratio for a 250 ml final transfection volume. Recombinant antibody derivative containing cell culture supernatants were clarified 7 days after transfection by centrifugation at 14000 g for 30 minutes and filtration through a sterile filter (0.22 µm). Supernatants were stored at −20° C. until purification.

Figure 8:
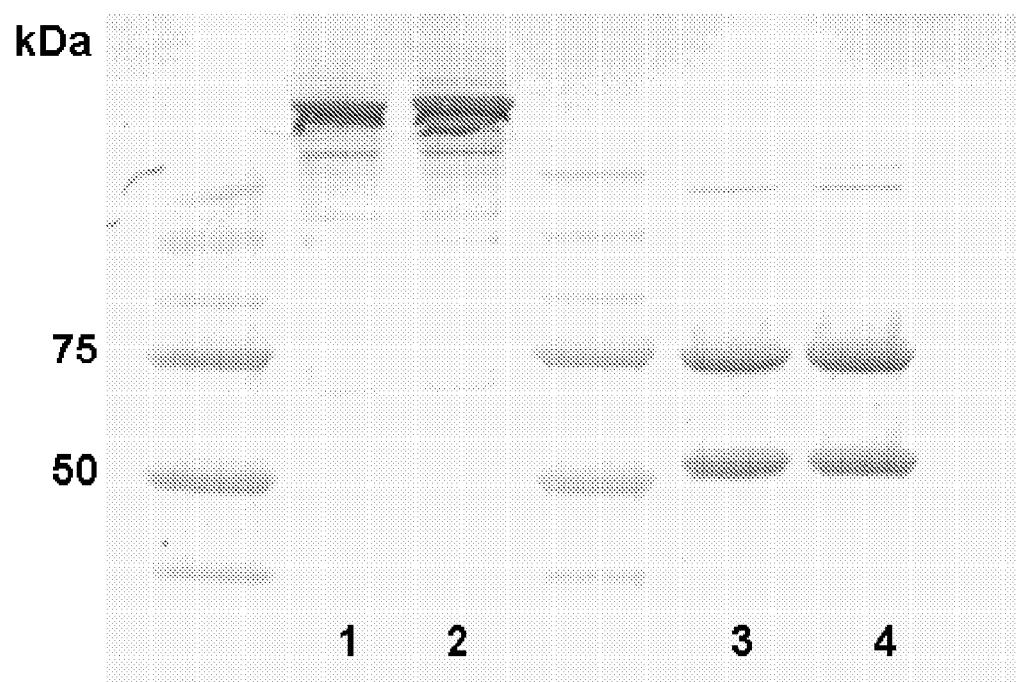
Figure 9A:
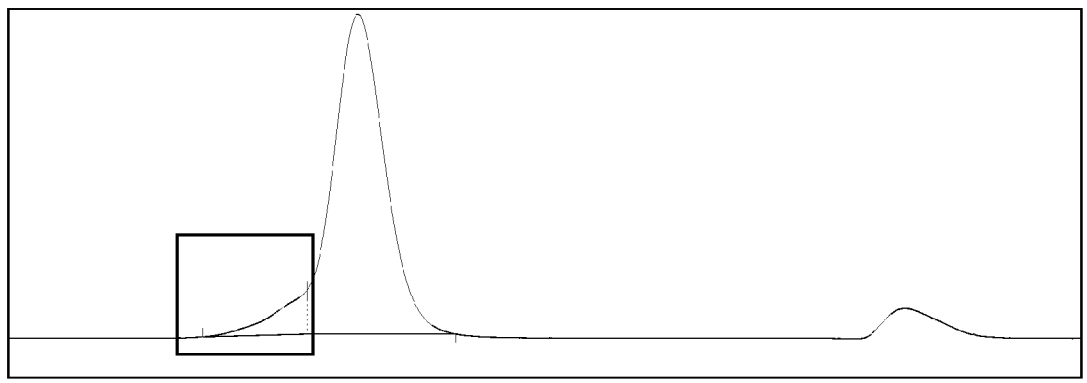
FIG. 9a: scFab-XGFR1-4720; 7.7%, Aggregates (marked within box)
Figure 9B:
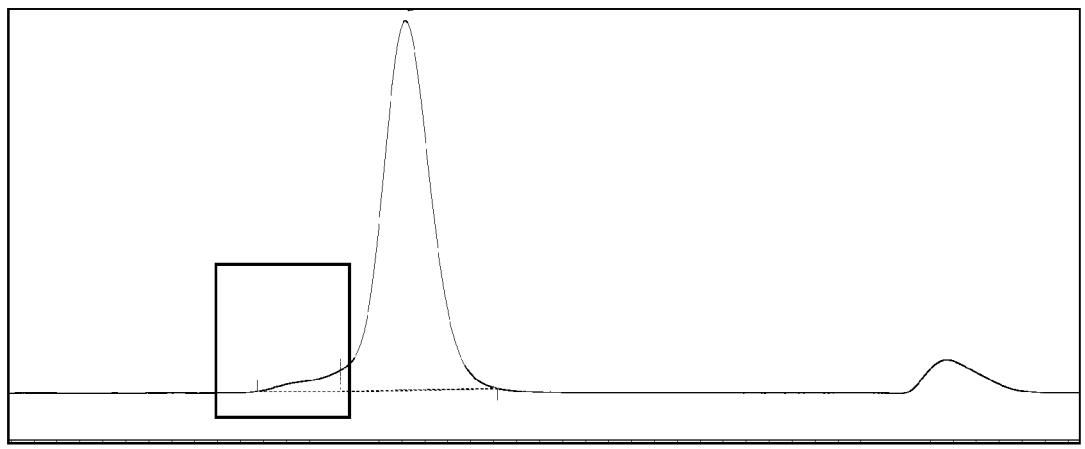
FIG. 9b: scFab-XGFR1-4721; 3.5%, Aggregates (marked within box)
Figure 10A:
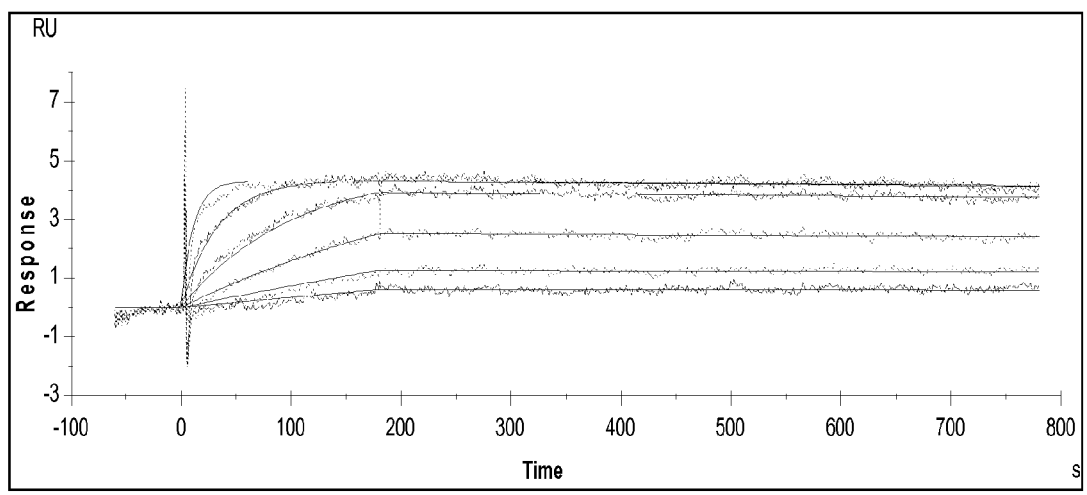
FIG. 10a: Biacore diagram-Binding of scFab-XGFR1_2720 to EGFR, KD=2 nM
Figure 10B:
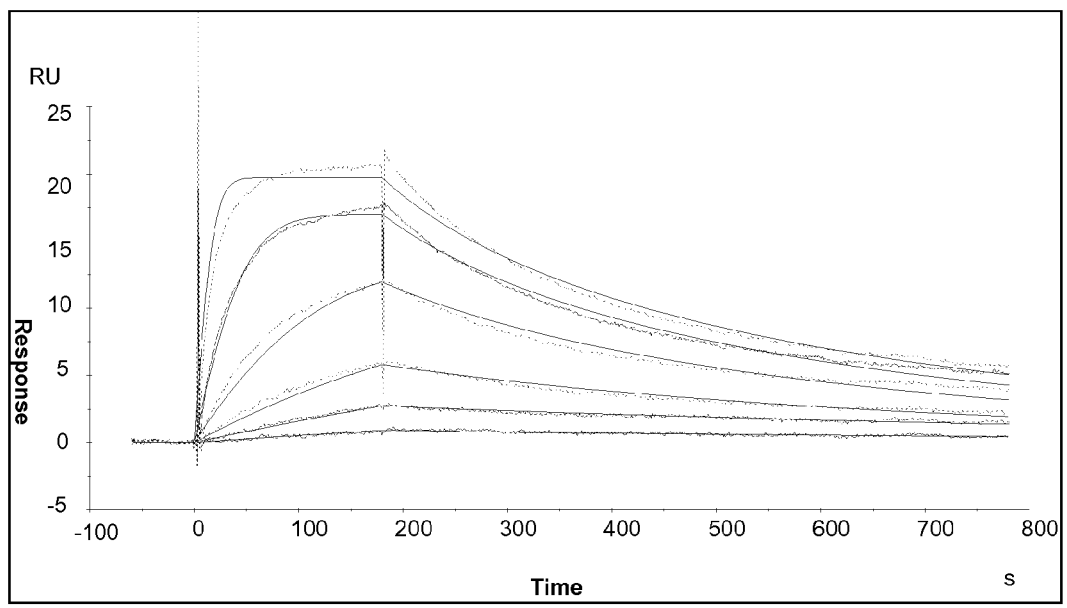
FIG. 10b: Biacore diagram-Binding of scFab-XGFR1_2720 to IGF-1R, KD=2 nM
Figure 10C:
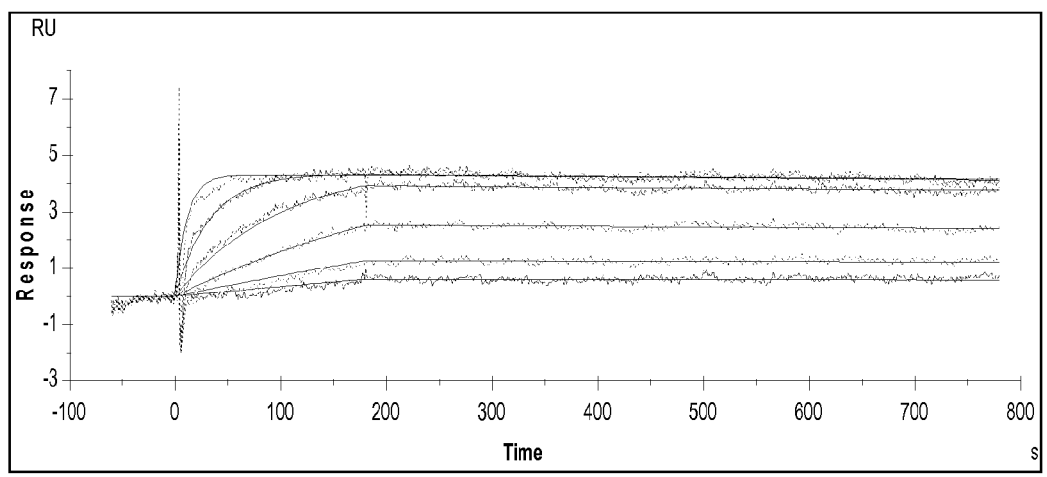
FIG. 10c: Biacore diagram-Binding of scFab-XGFR2_2720 to EGFR, KD=0.5 nM
Figure 10D:
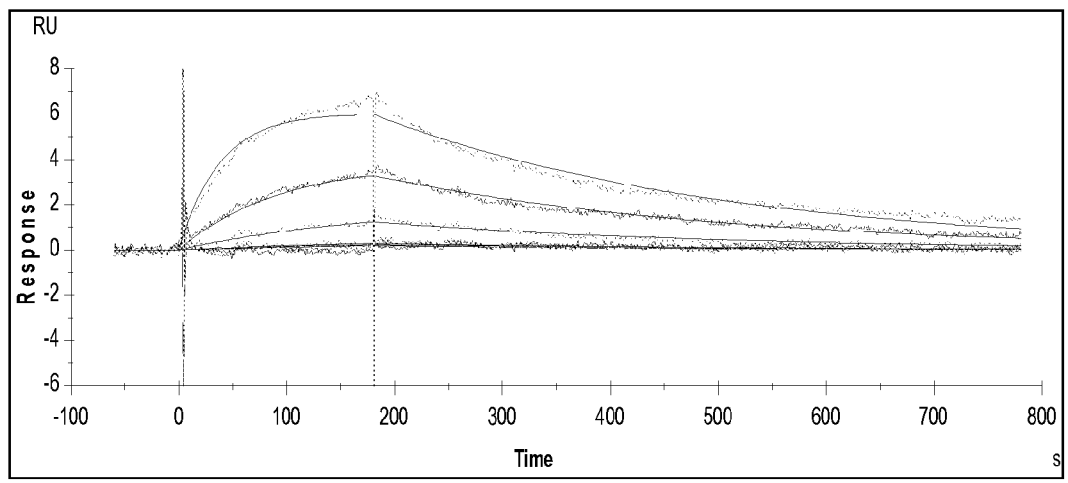
FIG. 10d: Biacore diagram-Binding of scFab-XGFR2_2720 to IGF-1R, KD=11 nM

The secreted antibody derivatives were purified from the supernatant in two steps by affinity chromatography using Protein A-Sepharose™ (GE Healthcare, Sweden) and Superdex200 size exclusion chromatography. Briefly, the bispecific and trispecific antibody containing clarified culture supernatants were applied on a HiTrap ProteinA HP (5 ml) column equilibrated with PBS buffer (10 mM $Na_2HPO_4$, 1 mM $KH_2PO_4$, 137 mM NaCl and 2.7 mM KCl, pH 7.4). Unbound proteins were washed out with equilibration buffer. The antibody derivatives were eluted with 0.1 M citrate buffer, pH 2.8, and the protein containing fractions were neutralized with 0.1 ml 1 M Tris, pH 8.5. Then, the eluted protein fractions were pooled, concentrated with an Amicon Ultra centrifugal filter device (MWCO: 30 K, Millipore) to a volume of 3 ml and loaded on a Superdex200 HiLoad 120 ml 16/60 gel filtration column (GE Healthcare, Sweden) equilibrated with 20 mM Histidin, 140 mM NaCl, pH 6.0. Monomeric antibody fractions were pooled, snap-frozen and stored at −80° C. Part of the samples were provided for subsequent protein analytics and characterization. Exemplary SDS-PAGE analyses of purified proteins and profiles of HP-Size Exclusion Chromatography (SEC) of bispecific antibody derivatives are shown in FIGS. 8 and 9.

FIG. 5 lists the expression yields that were observed in transient expression systems: All designed antibody derivatives could be expressed and purified in sufficient amounts for further analyses.

For comparison reasons a tetravalent bispecific antibody based on a full length antibody to which two scFv fragments are fused via a peptide linker at the C-terminus of the heavy chain as described in WO 1995/009917 and Muller D., et al, Handbook of Therapeutic antibodies, Part III, Chapter 2, (2008) 345-378 was prepared and named. As heavy chain variable domain VH for the <IGF-1R> antigen binding site SEQ ID NO: 15 was used. As light chain variable domain VL for the <IGF-1R> antigen binding site SEQ ID NO: 16 was used. As heavy chain variable domain VH for the <EGFR> antigen binding site SEQ ID NO: 7 was used. As light chain variable domain VL for the <EGFR> antigen binding site SEQ ID NO: 8 was used. This comparison molecule is named XGFR1.sub.--2320 (and is also described in PCT PCT/EP2009/006782). $(G_4S)_3$ is SEQ ID NO:29; $(G_4S)_2$ is SEQ ID NO:24.

and time) showed that compared to normal IgGs—a light tendency to aggregate for molecules that contained scFabs (This light aggregation tendency that we observed for some molecules could be ameliorated by introduction of the VH44NL100 interchain disulfide bond in scFab modules.

Example 4

Binding of Bispecific <EGFR-IGF1R> Antibody scFab-Molecules to the RTKs EGFR and IGF1R The binding of the scFab modules and of the antigen-binding sites of the retained in the full length IgG-module of the different bispecific antibody formats scFab-XGFR were compared to the binding of the 'wildtype' IgGs from which the binding modules and bispecific antibodies were derived. These analyses were carried out by applying Surface Plasmon Resonance (Biacore), as well as a cell-ELISA.

The binding properties bispecific <IGF-1R-EGFR> antibodies were analyzed by surface plasmon resonance (SPR) technology using a Biacore T100 instrument (GE Healthcare Bio-Sciences AB, Uppsala). This system is well established for the study of molecule interactions. It allows a continuous real-time monitoring of ligand/analyte bindings and thus the determination of association rate constants (ka), dissociation rate constants (kd), and equilibrium constants (KD) in various assay settings. SPR-technology is based on the measurement

| Comparison example | Full length Antibody backbone derived from | Single chain Fab fragment derived from | Variable Domains VH and VL: SEQ ID NO: | Position of scFv attached to antibody | Single-chainFv-linker | Peptide linker/ connector between scFv and C-terminus of heavy chain |
|---|---|---|---|---|---|---|
| scFv-XGFR1__2320 | <IGF1R> | <EGFR> | 7, 8, 15, 16 | C-terminus H chain | $(G_4S)_3$ | $(G_4S)_2$ |

The bispecific single chain Fv molecule XGFR1-2320 had a final yield after purification of 0.27 mg whereas the corresponding single chain Fab molecule XGFR1-2720 had a final yield of 6.8 mg (see FIG. 4, compound A), which represents a more than 200 fold increase in yield.

Example 3

Stability and Aggregation Tendency of Bispecific <EGFR-IGF1R> Antibody scFab-XGFR Molecules HP-Size exclusion chromatography analysis was performed to determine the amounts of aggregates that are present in preparation of recombinant antibody derivatives. For that, bispecific antibody samples were analyzed by high-performance SEC on an UltiMate 3000 HPLC system (Dionex) using a Superdex 200 analytical size-exclusion column (GE Healthcare, Sweden). FIG. 9 shows an example of these analyses. Aggregates appear as a separate peak or shoulder before the fractions that contain the monomeric antibody derivative. For this work, we define desired 'monomeric' molecules to be composed of 2 heterodimers of heavy and light chains—with scFabs connected to either of both. The integrity of the amino acid backbone of reduced bispecific antibody light and heavy chains and—fusion proteins was verified by NanoElectrospray Q-TOF mass spectrometry after removal of N-glycans by enzymatic treatment with Peptide-N-Glycosidase F (Roche Molecular Biochemicals).

HP-Size exclusion chromatography analysis of the purified proteins under different conditions (varying concentration of the refractive index close to the surface of a gold coated biosensor chip. Changes in the refractive index indicate mass changes on the surface caused by the interaction of immobilized ligand with analyte injected in solution. If molecules bind to immobilized ligand on the surface the mass increases, in case of dissociation the mass decreases.

Capturing anti-human IgG antibody was immobilized on the surface of a C1 biosensor chip using amine-coupling chemistry. Flow cells were activated with a 1:1 mixture of 0.1 M N-hydroxysuccinimide and 0.1 M 3-(N,N-dimethylamino)propyl-N-ethylcarbodiimide at a flow rate of 5 µl/min. Anti-human IgG antibody was injected in sodium acetate, pH 5.0 at 5 µg/ml, which resulted in a surface density of approximately 200 RU. A reference control flow cell was treated in the same way but with vehicle buffers only instead of the capturing antibody. Surfaces were blocked with an injection of 1 M ethanolamine/HCl pH 8.5. The bispecific antibodies were diluted in HBS-P and injected at a flow rate of 5 µl/min. The contact time (association phase) was 1 min for the antibodies at a concentration between 1 and 5 nM. EGFR-ECD was injected at increasing concentrations of 1.2, 3.7, 11.1, 33.3, 100 and 300 nM, IGF-1R at concentrations of 0.37, 1.11, 3.33, 10, 30 and 90 nM. The contact time (association phase) was 3 min, the dissociation time (washing with running buffer) 5 min for both molecules at a flowrate of 30 µl/min. All interactions were performed at 25° C. (standard temperature). The regeneration solutions of 0.85% phosphoric acid and 5 mM sodium hydroxide were injected each for 60 s at 5 µl/min flow to remove any non-covalently bound protein after each binding cycle. Signals were detected at a rate of one signal per second. Samples were injected at increasing concentrations.

Exemplary simultaneous binding of an bispecific antibody <IGF-1R-EGFR> antibodies to EGFR and IGF1R is shown in FIG. 10a-d.

TABLE 2

Affinities (KD) of bispecific antibodies (scFab-XGFR1__2720 and scFab-XGFR2__2720) to EGFR and IGF-1R

| Molecule | KD value (Affinity to EGFR) | KD value (Affinity to IGF-1R) |
|---|---|---|
| scFab-XGFR1__2720 | 2 nM | 2 nM |
| scFab-XGFR2__2720 | 0.5 nM | 11 nM |
| <IGF-1R> Clone18 | n.a. | 2 nM |
| <EGFR> ICR62 | 0.5 nM | n.a. |

Figure 11:
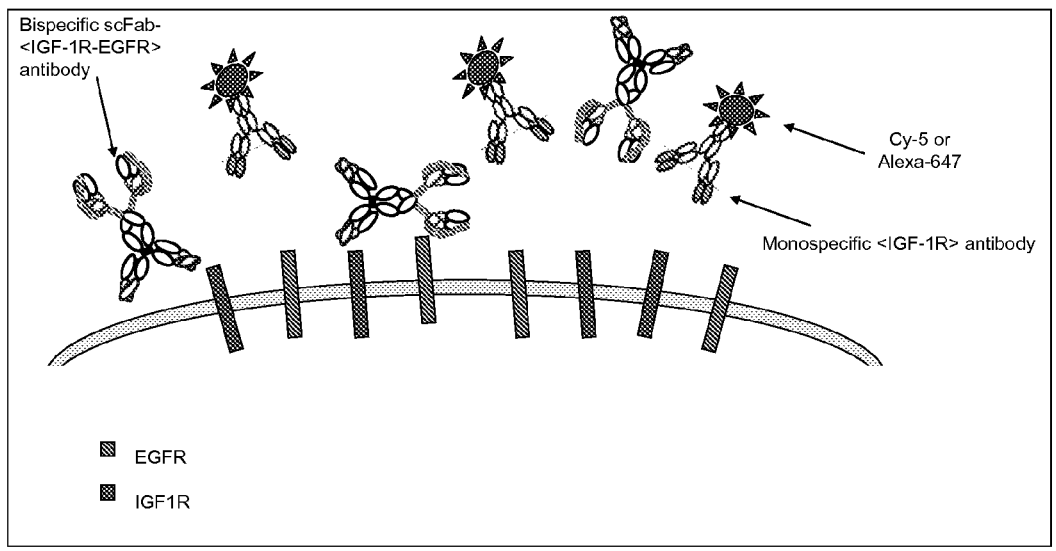
FIG. 11 Scheme—Binding of scFab-XGFR to cells analyzed by FACS competition assays with following general procedure:
add <IGF1R> Mab labeled with—Alexa647 (1 µg/mL)+ unlabeled scFab-XGFR (100 µg/mL–0.001 µg/mL) in parallel
45 min incubation on ice, wash & remove unbound antibodies
fix with 1% HCHO, then FACS FIG. 12 Binding of scFab-XGFR_2721 and parent <IGF1R> Clone18 to cells analyzed by FACS competition assays

FACS-based binding—and competition—analyses on cultured cells can also be applied to assess the binding capability of bispecific antibody derivatives to RTKs that are exposed on cell surfaces. FIG. 11 shows the experimental set-up that we used to test binding capabilities of scFab containing bispecific XGFR derivatives on A549 cancer cells. For these cellular competition assays, A549 cells which express the antigens EGFR as well IGF1R were detached and counted. $1.5 \times 10e5$ cells were seeded per well of a conical 96-well plate. Cells were spun down (1500 rpm, 4° C., 5 min) and incubated for 45 min on ice in 50 μL of a dilution series of the respective bispecific antibody in PBS with 2% FCS (fetal calf serum) containing 1 μg/mL of Alexa647-labeled IGF1R-specific antibody. Cells were again spun down and washed twice with 200 μL PBS containing 2% FCS. Finally, cells were resuspended in BD CellFix solution (BD Biosciences) and incubated for at least 10 min on ice. Mean fluorescence intensity (mfi) of the cells was determined by flow cytometry (FACS Canto). Mfi was determined at least in duplicates of two independent stainings Flow cytometry spectra were further processed using the FlowJo software (TreeStar). Half-maximal binding was determined using XLFit 4.0 (IDBS) and the dose response one site model 205.

Figure 12A:
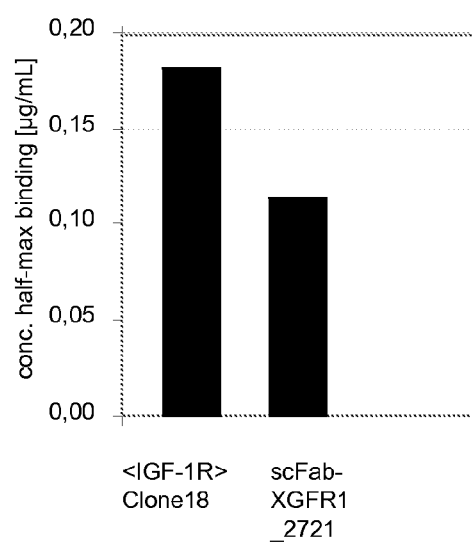
FIG. 12a: Comparison of IC50 values of <IGF-1R>Clone18 (0.18 µg/ml) and scFab-XGFR_2721 (0.15 µg/ml)
Figure 12B:
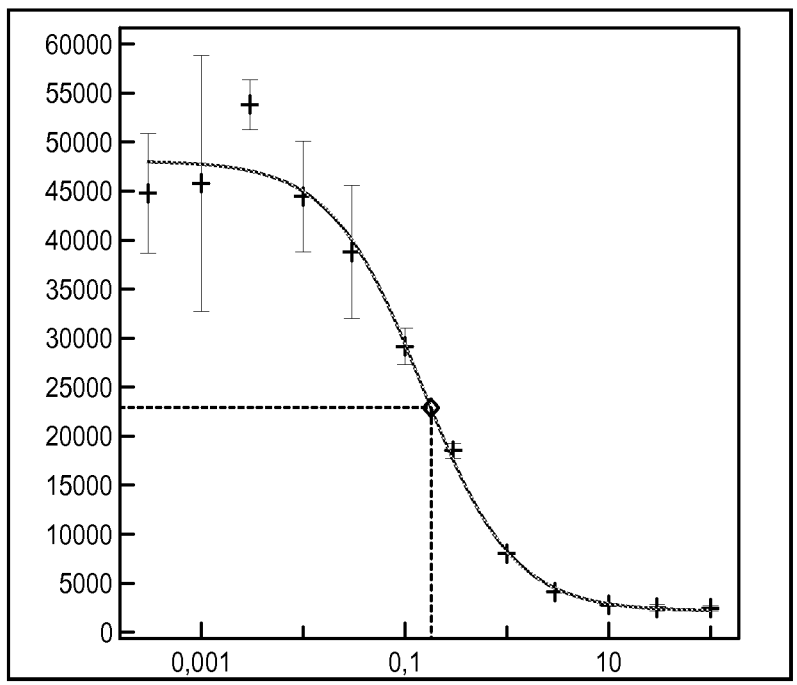
FIG. 12b: Binding curve of <IGF-1R>Clone18 (turning point 0.11 µg/ml)–y-axis=RLU; x-axis antibody concentration (µg/ml)
Figure 12C:
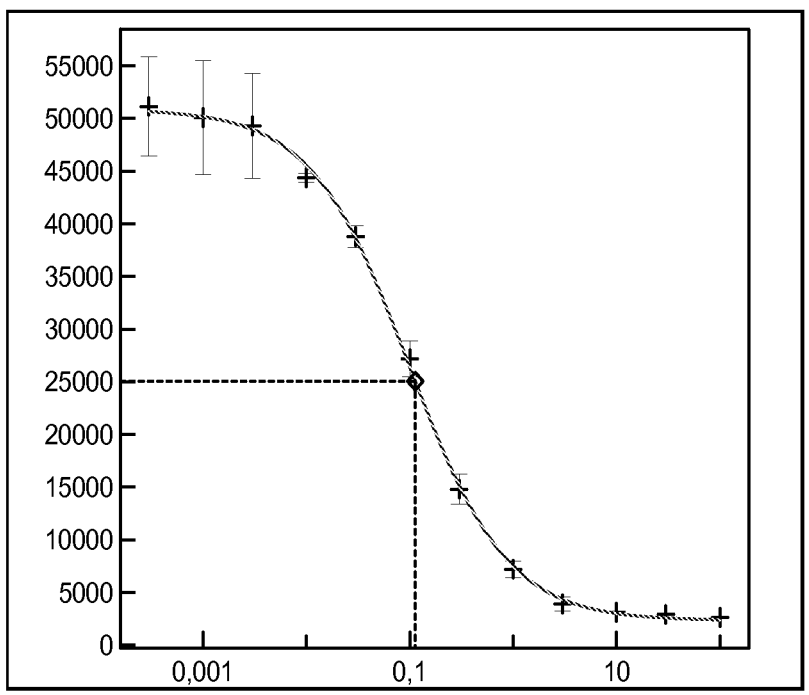
FIG. 12c: Binding curve of scFab-XGFR_2721 (turning point 0.10 µg/ml)–y-axis=RLU; x-axis antibody concentration (µg/ml)

The results of these assays which are shown in FIG. 12a-c demonstrate binding functionality of the bispecific scFab containing antibody derivatives on surfaces of tumor cells. For example, the IC50 in competition experiments of the bispecific antibody derivative scFab-XGFR1_2721 was 0.11 ug/ml whereas the IC50 of the monospecific antibody was >50% higher (0.18 ug/ml). This increased activity in competition assays of the bispecific scFab-XGFR_2721 derivative compared to the parent antibody suggests that the bispecific molecule binds better to cell surfaces than the monospecific antibody.

Example 5

Downregulation of EGFR- as Well as IGF-1R- by Bispecific <EGFR-IGF-1R> Antibody scFab-XGFR Molecules The human anti-IGF-1R antibodies <IGF-1R> HUMAB Clone 18 (DSM ACC 2587) inhibits IGFR1-signaling and the humanized rat anti-EGFR antibody <EGFR>ICR62 inhibits the signaling by EGFR. To evaluate the potential inhibitory activity of the different scFab-XGFR1 variants, the degree of downregulation of the receptor from both was analyzed.

In order to detect effects of the antibody of the invention on the amount of IGF-I receptor (IGF-IR) in tumor cells, time-course experiments and subsequent ELISA analysis with IGF-IR and EGFR specific antibodies were performed.

A 6 well plate was inoculated with 1 ml per well human tumor cells (H322M, $5 \times 10^5$ cells/ml) in RPMI 1640 supplemented with 10% FCS (PAA, Cat. No. E15-039) and 1% PenStrep. 3 ml medium were added to each well and the cells were cultivated for 24 hours at 37° C. and 5% $CO_2$.

The medium was carefully removed and replaced by 2 ml 100 nM XGFR antibodies diluted in RPMI-VM medium. In control wells, medium was replaced by either medium and buffer without antibody and medium with control antibodies (<IGF-1R> HUMAB Clone 18 and <EGFR>ICR62 final concentration 100 nM). Cells were incubated at 37° C. and 5% $CO_2$ and individual plates were taken out for further processing after 24 hours.

The medium was carefully removed by aspiration and the cell were washed with 1 ml PBS. 300 μl/well of cold MES-lysis buffer was added (MES, 10 mM $Na_3VO_4$, and Complete® protease inhibitor). After one hour the cells were detached on ice using a cell scraper (Corning, Cat. No. 3010) and the well contents transferred to Eppendorf reaction tubes. Cell fragments were removed by centrifugation for 10 minutes at 13000 rpm and 4° C.

For EGFR Detection

The 96 well microtitreplates (MTP) were prepared according to the protocol (DuoSet ELISA for Human EGFR, RnD systems Cat. No. DY231). The Human EGFR goat antibody 144 μg/ml in PBS was diluted 1:180 in PBS and 100 μl/well was added to the MTP. The MTP was incubated overnight at room temperature with agitation. The plates were washed 3 times with PBS supplemented with 0.1% Tween® 20 and blocked with 300 μl/well of PBS, 3% BSA and 0.1% Tween® 20 solution for 1 hour (h) at room temperature (RT) with agitation. The plates were washed 3 times with PBS supplemented with 0.1° A Tween® 20.

The amount of protein in the cell lysates was determined using the BCA Protein Assay kit (Pierce), the cell lysates were then adjusted to a protein concentration of 0.04 mg/ml with MES-lysis buffer supplemented with 100 mM $Na_3VO_4$ 1:100 and Complete® protease inhibitor 1:20 and 100 μl per well of the lysate was added to the pre-prepared MTP. For background measurement 100 μl lysis buffer was added to the well in the MTP.

A second cell lysate concentration was used at 0.025 mg/ml the lysate was dilute 1:2 and 100 μl was added per well to the pre-prepared MTP. The MTP were incubated for a further 2 hour at RT with agitation and then washed 3 times with PBS with 0.1% Tween® 20 solution.

The detection antibody for EGFR was human EGFR goat biotinylated antibody at a concentration of 36 μg/ml diluted 1:180 in PBS, 3% BSA and 0.2% Tween® 20. 100 μl per well was added and incubated at RT for 2 hours with agitation. The MTP was then washed three times with 200 μl per well of PBS with 0.1% Tween® 20 solution. Then Streptavidin-HRP 1:200 in PBS, 3% BSA and 0.2% Tween® 20 100 μl per well was added and incubated with agitation for 20 minutes at RT. The plate was then washed six times with PBS with 0.1% Tween® 20 solution. 100 μl per well of 3,3'-5,5'-Tetramethylbenzidine (Roche, BM-Blue ID-No.: 11484581) was added and incubated for 20 minutes at RT with agitation. The color reaction was stopped by adding 25 μl per well of 1M $H_2SO_4$ and incubating for a further 5 minutes at RT. The absorbance was measured at 450 nm.

For IGF-1R Detection

The streptavidin-MTP (Roche ID. No.: 11965891001) was prepared by adding 100 μl per well of the antibody AK1a-Biotinylated (Genmab, Denmark) which was diluted 1:200 in PBS, 3% BSA and 0.2% Tween® 20. The streptavidin-MTP was incubated for 1 hour at RT with agitation and then washed three times with 200 μl per well of PBS with 0.1% Tween® 20 solution.

The amount of protein in the cell lysates was determined using the BCA Protein Assay kit (Pierce), the cell lysates were then adjusted to a protein concentration of 0.3 mg/ml with 50 mM Tris pH 7.4, 100 mM $Na_3VO_4$ 1:100 and Complete® protease inhibitor 1:20 and 100 μl per well of the lysate was added to the pre-prepared streptavidin-MTP.

A second cell lysate concentration was used at 0.15 mg/ml the lysate was dilute and 100 μl was added per well to the pre-prepared streptavidin-MTP. For background measurement 100 μl lysis buffer was added to the well in the streptavidin-MTP.

The MTP were incubated for a further 1 hour at RT with agitation and then washed 3 times with PBS with 0.1% Tween® 20 solution.

The detection antibody for IGF-1R was human IGF-1Rβ rabbit antibody (Santa Cruz Biotechnology, Cat. No. sc-713) diluted 1:750 in PBS, 3% BSA and 0.2% Tween® 20. 100 μl per well was added and incubated at RT for 1 hour with agitation. The MTP was then washed three times with 200 μl per well of PBS with 0.1% Tween® 20 solution. The secondary antibody was then added rabbit IgG-POD (Cell signaling Cat. No. 7074) 1:4000 in PBS, 3% BSA and 0.2% Tween® 20, 100 μl was added per well and incubated with agitation for 1 hour at RT. The plate was then washed six times with PBS with 0.1% Tween® 20 solution. 100 μl per well of 3,3'-5,5'-Tetramethylbenzidin (Roche, BM-Blue ID-No.: 11484581) was added and incubated for 20 minutes at RT with agitation. The color reaction was stopped by adding 25 μl per well of 1M $H_2SO_4$ and incubating for a further 5 minutes at RT. The absorbance was measured at 450 nm.

Figure 13:
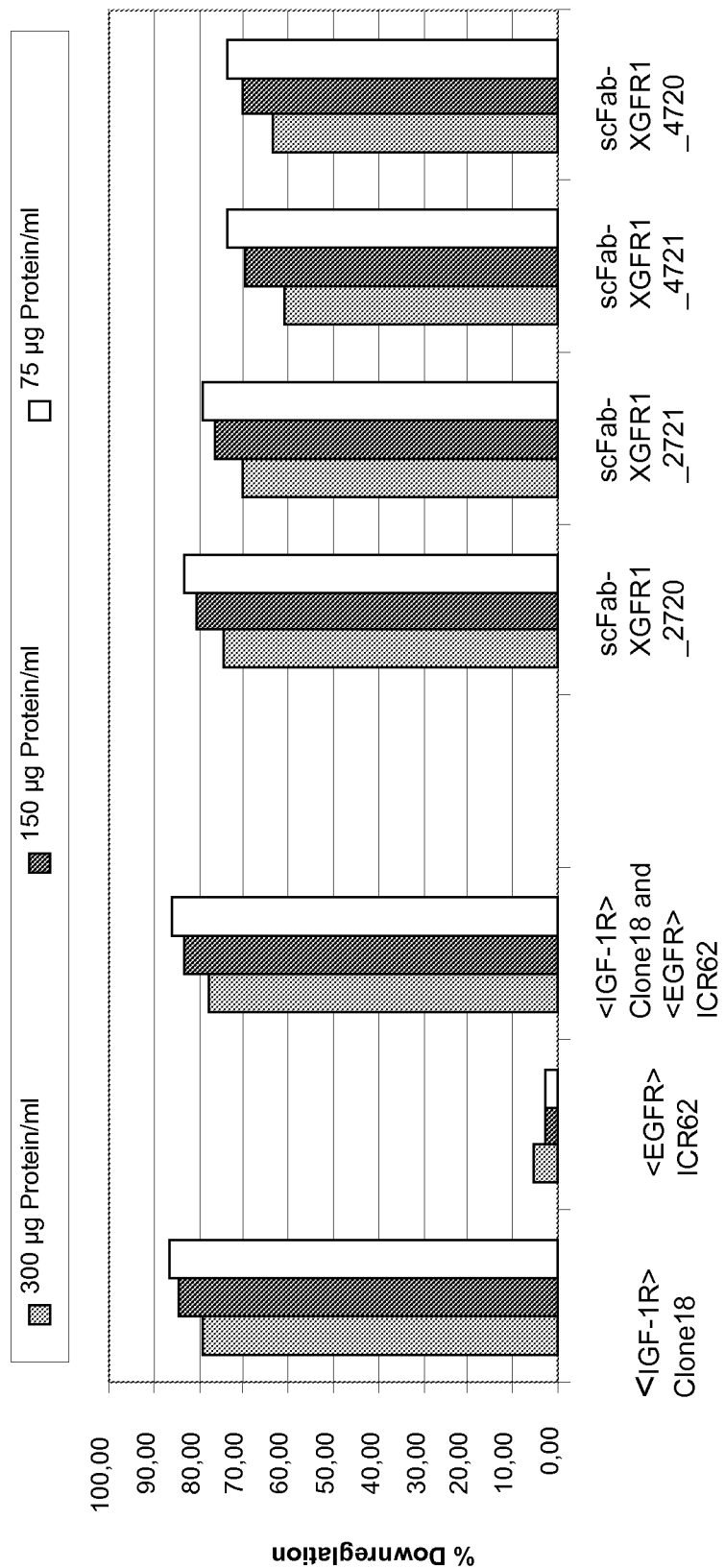
FIG. 13 Downregulation of IGF1-R on H322M-Cells after 24 h incubation with different scFab-XGFR variants (100 nM)
Figure 14:
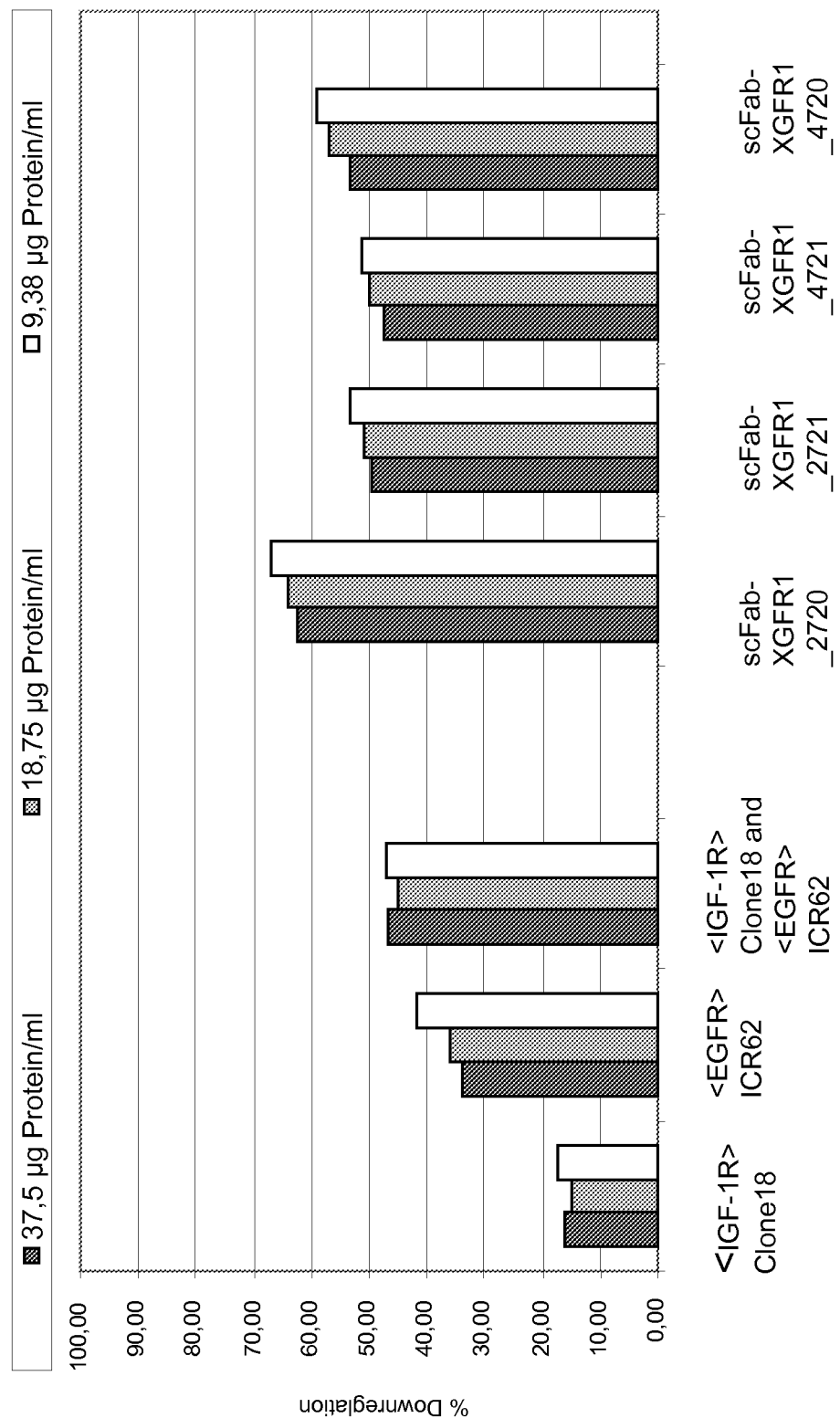
FIG. 14 Downregulation of EGFR on H322M-Cells after 24 h incubation with different scFab-XGFR variants (100 nM)

The results of the receptor downregulation detection by the bispecific scFab containing XGFR molecules compared to the parent monospecific antibodies <EGFR>ICR62 and <IGF-1R> HUMAB-Clone 18 in A549 cells is shown in FIGS. 13 and 14. The bispecific antibodies scFab-XGFR downregulate both EGFR- as well as the IGF1R. This shows that full functionality (biological functionality) and phenotype mediation of the binding modules is retained. FIG. 14 also indicates that, surprisingly, the bispecific antibodies scFab-XGFR_2720 showed an improved downregulation of EGFR compared to the parent <EGFR>ICR62 antibody alone.

The fact that scFab containing XGFR1 variants when applied to the same assays at identical molarities, showed the same or better activities than the wildtype antibodies indicates that scFab-XGFR1 molecules are capable of interfering with both signaling pathways.

Example 6 scFab-XGFR1 and scFab-XGFR2-Mediated Growth Inhibition of Tumor Cell Lines In Vitro The human anti-IGF-1R antibody <IGF-1R> HUMAB Clone 18 (DSM ACC 2587) inhibits the growth of tumor cell lines that express the IGF1R (WO 2005/005635). In a similar manner, the humanized rat anti-EGFR antibody <EGFR>ICR62 has been shown to inhibit the growth of tumor cell lines that express EGFR (WO 2006/082515). To evaluate the potential inhibitory activity of the different scFab-XGFR1 variants in growth assays of tumor cell lines, the degree of inhibition in H322M cells which express EGFR as well as IGF1R was analyzed.

H322M cells (5000 cells/well) were cultured in RPMI 1640 media supplemented with 10% FCS on poly-HEMA (poly(2-hydroxyethylmethacrylate)) coated dishes to prevent adherence to the plastic surface. Under these conditions H322M cells form dense spheroids that grow three dimensionally (a property that is called anchorage independence). These spheroids resemble closely the three dimensional histoarchitecture and organization of solid tumors in-situ. Spheroid cultures were incubated for 7 days in the presence of 100 nM antibodies. The Celltiter Glow luminescence assay was used to measure growth inhibition. When H322M spheroid cultures were treated with <IGF-1R> HUMAB-Clone18 an inhibition in growth could be observed.

Figure 15:
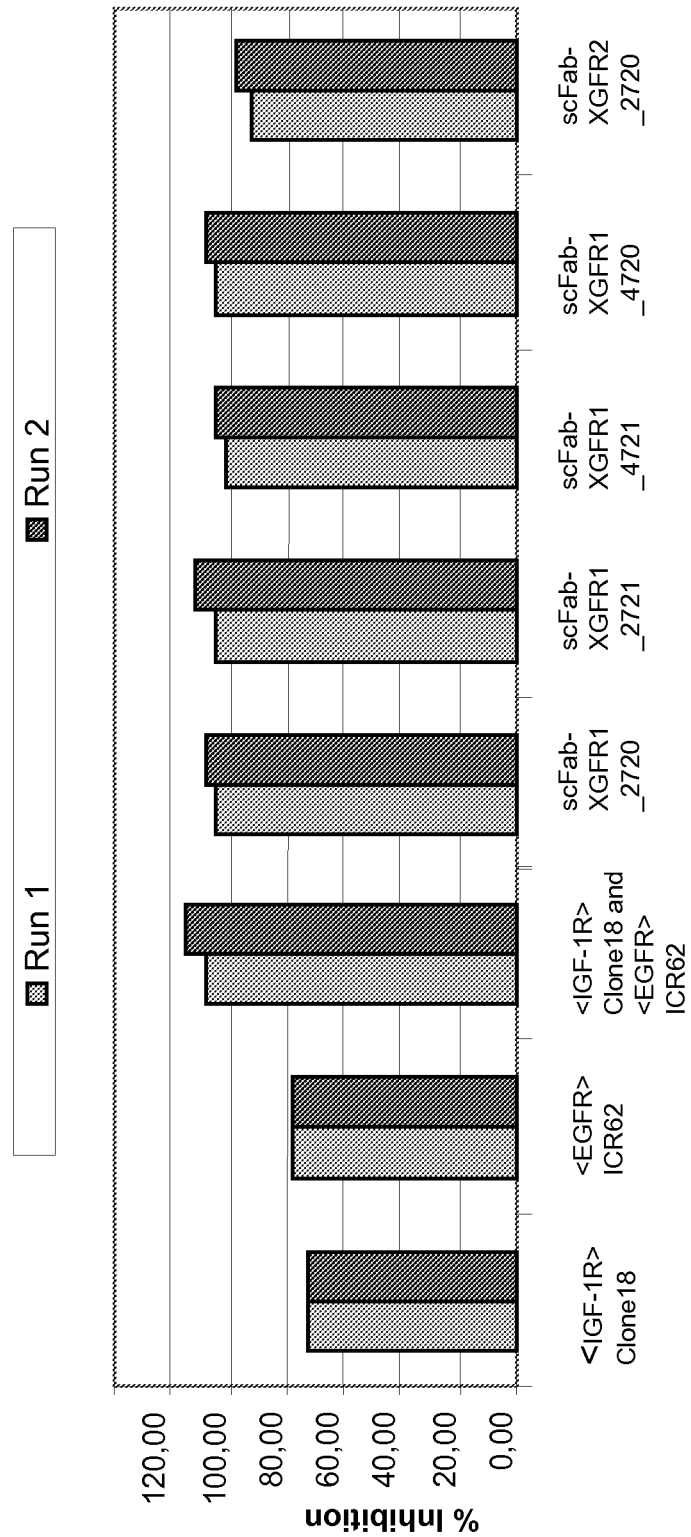
FIG. 15 Inhibition of the proliferation from H322M-cells with different scFab-XGFR variants (100 nM)

FIG. 15 shows that the application of 100 nM <IGF-1R> HUMAB-Clone18 reduced the cell growth by 72%, and that the application of 100 nM <EGFR>ICR62 reduced the cell growth by 77% in the same assay. The simultaneous application of both antibodies (both at the same concentrations of 100 nM) resulted in a complete decrease of cell viability (100% inhibition). This indicates that simultaneous interference with both RTK pathways has a more profound effect on tumor cell lines than the interference with just one pathway alone. Application of various scFab-XGFR1-variants at molar concentration of 100 nM resulted in a higher growth inhibition that was more pronounced that that observed with single molecules alone. In fact, at an antibody concentration of 100 nM, various scFab-XGFR1-variants showed complete (100%) inhibition of cell growth, while application of single modules caused only partial inhibition.

We conclude that scFab-XGFR1 molecules have a profoundly increased growth inhibitory activity compared to IgGs that solely interfere with either EGFR signaling or IGF1R signaling.

What is claimed is:

1. A multispecific antibody comprising
   a) a full length antibody consisting of two antibody heavy chains and two antibody light chains wherein the antibody specifically binds to a first antigen; and
   b) one or two single chain Fab fragments that specifically bind to one or two antigens different from the first antigen, wherein each of the single Fab fragments comprises an antibody light chain variable domain (VL) and an antibody heavy chain variable domain (VH) that binds to the antigen that is different from the first antigen,
   wherein each of the one or two single chain Fab fragments is fused to the full length antibody via a peptide connector at the C- or N-terminus of the heavy chain of the full length antibody.

2. The multispecific antibody according to claim 1, wherein one or two single chain Fab fragments that specifically bind to a second antigen are each fused to the full length antibody via a peptide connector at the C-terminus of the heavy chains of the full length antibody.

3. The multispecific antibody according to claim 2, wherein one single chain Fab fragment that specifically binds to a second antigen is fused to the full length antibody via a peptide connector at the C-terminus of one heavy chain of the full length antibody.

4. The multispecific antibody according to claim 1, wherein two identical single chain Fab fragments VL-CL-linker-VH-CH1 or VH-CH1-linker-VL-CL that specifically bind to a second antigen are fused at their N-termini to the full length antibody via a peptide connector at the two C-termini of the two heavy chains of the full length antibody.

5. The multispecific antibody according to claim 1, wherein two identical single chain Fab fragments VL-CLlinker-VH-CH1 or VH-CH1-linker-VL-CL that specifically bind to a second antigen are fused at their C-termini to the full length antibody via a peptide connector at the two N-termini of the two heavy chains of the full length antibody.

6. The multispecific antibody according to claim 1, wherein one or two single chain Fab fragments that specifically bind to a second antigen are each fused to the full length antibody via a peptide connector at the N-terminus of the heavy chains of the full length antibody.

7. The multispecific antibody according to claim 6, wherein one single chain Fab fragment that specifically binds to a second antigen is fused to the full length antibody via a peptide connector at the N-terminus of one heavy chain of the full length antibody.

8. The multispecific antibody according to claim 1, wherein each of the one or two single chain Fab fragments comprises a disulfide bond between heavy chain variable domain and light chain variable domain of the single chain Fab fragment, wherein the disulfide bond is between:
   i) heavy chain variable domain position 44 to light chain variable domain 100;
   ii) heavy chain variable domain position 105 to light chain variable domain 43; or
   iii) heavy chain variable domain position 101 to light chain variable domain position 100, wherein the numbering is based on the EU index of Kabat.

9. A pharmaceutical composition comprising an antibody according to claim 1.

10. A pharmaceutical composition comprising an antibody according to claim 2.

11. A pharmaceutical composition comprising an antibody according to claim 3.

12. A pharmaceutical composition comprising an antibody according to claim 4.

13. A pharmaceutical composition comprising an antibody according to claim 5.

14. A multispecific antibody comprising
   a) a full length antibody consisting of two antibody heavy chains and two antibody light chains wherein the antibody specifically binds to a first antigen; and
   b) one to four single chain Fab fragments that specifically bind to one to four antigens different from the first antigen, wherein each of the single chain Fab fragments comprises an antibody light chain variable domain (VL) and an antibody heavy chain variable domain (VH) that binds to the antigen that is different from the first antigen,
   wherein each of the one to four single chain Fab fragments is fused to the full length antibody via a peptide connector at the C- or N- terminus of the heavy chain of the full length antibody, and wherein each of the one to four single chain Fab fragments comprises a disulfide bond between heavy chain variable domain and light chain variable domain of the single chain Fab fragment.

15. The multispecific antibody according to claim 14, comprising one or two single chain Fab fragments that specifically bind to one or two antigens different from the first antigen, wherein each of the one or two single chain Fab fragments is fused to the full length antibody via a peptide connector at the C- or N- terminus of the heavy chain of the full length antibody.

16. The multispecific antibody according to claim 14, wherein one or two single chain Fab fragments that specifically bind to a second antigen are each fused to the full length antibody via a peptide connector at the C-terminus of the heavy chains of the full length antibody.

17. The multispecific antibody according to claim 16, wherein one single chain Fab fragment that specifically binds to a second antigen is fused to the full length antibody via a peptide connector at the C-terminus of one heavy chain of the full length antibody.

18. The multispecific antibody according to claim 14, wherein two identical single chain Fab fragments VL-CL-linker-VH-CH1 or VH-CH1-linker-VL-CL that specifically bind to a second antigen are fused at their N-termini to the full length antibody via a peptide connector at the two C-termini of the two heavy chains of the full length antibody.

19. The multispecific antibody according to claim 14, wherein two identical single chain Fab fragments VL-CL-linker-VH-CH1 or VH-CH1-linker-VL-CL that specifically bind to a second antigen are fused at their C-termini to the full length antibody via a peptide connector at the two N-termini of the two heavy chains of the full length antibody.

20. The multispecific antibody according to claim 14, wherein the disulfide bond is between: i) heavy chain variable domain position 44 to light chain variable domain 100; ii) heavy chain variable domain position 105 to light chain variable domain 43; or iii) heavy chain variable domain position 101 to light chain variable domain position 100, wherein the numbering is based on the EU index of Kabat.

21. A pharmaceutical composition comprising an antibody according to claim 14.

22. A pharmaceutical composition comprising an antibody according to claim 15.

* * * * *

SEQUENCE LISTING

```
<160> NUMBER OF SEQ ID NOS: 29

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1
```

-continued

```
Glu Leu Gly Arg Arg Tyr Phe Asp Leu
1               5

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ile Ile Trp Phe Asp Gly Ser Ser Thr Tyr Tyr Ala Asp Ser Val Arg
1               5                   10                  15

Gly

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ser Tyr Gly Met His
1               5

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gln Gln Arg Ser Lys Trp Pro Pro Trp Thr
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asp Ala Ser Lys Arg Ala Thr
1               5

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Ala Ser Gln Ser Val Ser Ser Tyr Leu Ala
1               5                   10

<210> SEQ ID NO 7
<211> LENGTH: 118
<212> TYPE: PRT
```

```
<213> ORGANISM: Homo sapiens

<400> SEQUENCE: 7

Gln Val Glu Leu Val Glu Ser Gly Gly Gly Val Val Gln Pro Gly Arg
 1               5                  10                  15

Ser Gln Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Phe Asp Gly Ser Ser Thr Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Glu Leu Gly Arg Arg Tyr Phe Asp Leu Trp Gly Arg Gly Thr
            100                 105                 110

Leu Val Ser Val Ser Ser
            115

<210> SEQ ID NO 8
<211> LENGTH: 108
<212> TYPE: PRT
<213> ORGANISM: Homo sapiens

<400> SEQUENCE: 8

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Lys Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Lys Trp Pro Pro
                85                  90                  95

Trp Thr Phe Gly Gln Gly Thr Lys Val Glu Ser Lys
            100                 105

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Leu Ser Pro Gly Gly Tyr Tyr Val Met Asp Ala
 1               5                  10

<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 10

Tyr Phe Asn Pro Asn Ser Gly Tyr Ser Thr Tyr Ala Gln Lys Phe Gln
1               5                   10                  15

Gly

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asp Tyr Lys Ile His
1               5

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Leu Gln His Asn Ser Phe Pro Thr
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Asn Thr Asn Asn Leu Gln Thr
1               5

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Arg Ala Ser Gln Gly Ile Asn Asn Tyr Leu Asn
1               5                   10

<210> SEQ ID NO 15
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Thr Asp Tyr

```
                    20                  25                  30

Lys Ile His Trp Val Arg Gln Ala Pro Gly Gln Gly Leu Glu Trp Met
            35                  40                  45

Gly Tyr Phe Asn Pro Asn Ser Gly Tyr Ser Thr Tyr Ala Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Ser Pro Gly Gly Tyr Tyr Val Met Asp Ala Trp Gly Gln
            100                 105                 110

Gly Thr Thr Val Thr Val Ser Ser
            115                 120

<210> SEQ ID NO 16
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Asn Tyr
            20                  25                  30

Leu Asn Trp Tyr Gln Gln Lys Pro Gly Lys Ala Pro Lys Arg Leu Ile
        35                  40                  45

Tyr Asn Thr Asn Asn Leu Gln Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Phe Pro Thr
                85                  90                  95

Phe Gly Gln Gly Thr Lys Leu Glu Ile Lys Arg Thr
            100                 105

<210> SEQ ID NO 17
<211> LENGTH: 330
<212> TYPE: PRT
<213> ORGANISM: Homo sapiens

<400> SEQUENCE: 17

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
```

```
                   100                 105                 110
Pro Ala Pro Glu Leu Leu Gly Gly Pro Ser Val Phe Leu Phe Pro
            115                 120                 125
Pro Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 18
<211> LENGTH: 327
<212> TYPE: PRT
<213> ORGANISM: Homo sapiens

<400> SEQUENCE: 18

Ala Ser Thr Lys Gly Pro Ser Val Phe Pro Leu Ala Pro Cys Ser Arg
1               5                  10                  15
Ser Thr Ser Glu Ser Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Lys Thr
65                  70                  75                  80
Tyr Thr Cys Asn Val Asp His Lys Pro Ser Asn Thr Lys Val Asp Lys
                85                  90                  95
Arg Val Glu Ser Lys Tyr Gly Pro Pro Cys Pro Ser Cys Pro Ala Pro
            100                 105                 110
Glu Phe Leu Gly Gly Pro Ser Val Phe Leu Phe Pro Pro Lys Pro Lys
        115                 120                 125
Asp Thr Leu Met Ile Ser Arg Thr Pro Glu Val Thr Cys Val Val Val
    130                 135                 140
```

```
Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
            165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 19
<211> LENGTH: 107
<212> TYPE: PRT
<213> ORGANISM: Homo sapiens

<400> SEQUENCE: 19

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
            85                  90                  95

Pro Val Thr Lys Ser Phe Asn Arg Gly Glu Cys
        100                 105

<210> SEQ ID NO 20
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(24)
<223> OTHER INFORMATION: This region may encompass 3, 4, 5 or 6
      repeating "GGGS" units
<220> FEATURE:
```

<223> OTHER INFORMATION: see specification as filed for detailed
      description of substitutions and preferred embodiments

<400> SEQUENCE: 20

Gly Gly Gly Ser Gly Gly Gly Ser Gly Gly Gly Ser Gly Gly Gly Ser
1               5                   10                  15

Gly Gly Gly Ser Gly Gly Gly Ser
            20

<210> SEQ ID NO 21
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(24)
<223> OTHER INFORMATION: This region may encompass 3, 4, 5 or 6
      repeating "GGGS" units
<220> FEATURE:
<221> NAME/KEY: MOD_RES
<222> LOCATION: (25)..(27)
<223> OTHER INFORMATION: May or may not be present
<220> FEATURE:
<223> OTHER INFORMATION: see specification as filed for detailed
      description of substitutions and preferred embodiments

<400> SEQUENCE: 21

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly
            20                  25

<210> SEQ ID NO 22
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(25)
<223> OTHER INFORMATION: This region may encompass 2, 3, 4 or 5
      repeating "GGGGS" units
<220> FEATURE:
<223> OTHER INFORMATION: see specification as filed for detailed
      description of substitutions and preferred embodiments

<400> SEQUENCE: 22

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 23
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(25)
<223> OTHER INFORMATION: This region may encompass 2, 3, 4 or 5
      repeating "GGGGS" units
<220> FEATURE:

```
<221> NAME/KEY: MOD_RES
<222> LOCATION: (26)..(28)
<223> OTHER INFORMATION: May or may not be present
<220> FEATURE:
<223> OTHER INFORMATION: see specification as filed for detailed
      description of substitutions and preferred embodiments

<400> SEQUENCE: 23

Gly Gly Gly Gly Ser Gly Gly Gly Ser Gly Gly Gly Gly Ser Gly
1               5                   10                  15

Gly Gly Gly Ser Gly Gly Gly Gly Ser Gly Gly Gly
            20                  25

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Gly Gly Gly Ser Gly Gly Gly Gly Ser
1               5                   10

<210> SEQ ID NO 25
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(40)
<223> OTHER INFORMATION: This region may encompass 8, 9 or 10 repeating
      "GGGS" units
<220> FEATURE:
<221> NAME/KEY: MOD_RES
<222> LOCATION: (41)..(43)
<223> OTHER INFORMATION: May or may not be present
<220> FEATURE:
<223> OTHER INFORMATION: see specification as filed for detailed
      description of substitutions and preferred embodiments

<400> SEQUENCE: 25

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser Gly Gly Gly
            35                  40

<210> SEQ ID NO 26
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(40)
<223> OTHER INFORMATION: This region may encompass 6, 7 or 8 repeating
      "GGGGS" units
<220> FEATURE:
<221> NAME/KEY: MOD_RES
<222> LOCATION: (41)..(43)
<223> OTHER INFORMATION: May or may not be present
<220> FEATURE:
```

```
<223> OTHER INFORMATION: see specification as filed for detailed
      description of substitutions and preferred embodiments

<400> SEQUENCE: 26

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
                20                  25                  30

Gly Gly Ser Gly Gly Gly Gly Ser Gly Gly Gly
            35                  40

<210> SEQ ID NO 27
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
                20                  25                  30

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Gly Gly Gly Ser
1               5

<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Gly Gly Gly Ser Gly Gly Gly Gly Ser Gly Gly Gly Gly Ser
1               5                   10                  15
```